US011426459B2

(12) United States Patent
Chen et al.

(10) Patent No.: US 11,426,459 B2
(45) Date of Patent: Aug. 30, 2022

(54) MUTANT OF HEMAGGLUTININ PROTEIN OF H3N2 SUBTYPE INFLUENZA VIRUS AND USE THEREOF

(71) Applicant: Xiamen University, Xiamen (CN)

(72) Inventors: Yixin Chen, Xiamen (CN); Chenguang Shen, Xiamen (CN); Junyu Chen, Xiamen (CN); Mengya Zhang, Xiamen (CN); Limin Zhang, Xiamen (CN); Ningshao Xia, Xiamen (CN)

(73) Assignee: Xiamen University, Xiamen (CN)

( * ) Notice: Subject to any disclaimer, the term of this patent is extended or adjusted under 35 U.S.C. 154(b) by 0 days.

(21) Appl. No.: 16/756,973

(22) PCT Filed: Oct. 10, 2018

(86) PCT No.: PCT/CN2018/109589
§ 371 (c)(1),
(2) Date: Apr. 17, 2020

(87) PCT Pub. No.: WO2019/076218
PCT Pub. Date: Apr. 25, 2019

(65) Prior Publication Data
US 2021/0023198 A1    Jan. 28, 2021

(30) Foreign Application Priority Data
Oct. 18, 2017    (CN) .......................... 201710969146.0

(51) Int. Cl.
*A61K 39/145*    (2006.01)
*A61K 39/00*    (2006.01)
(52) U.S. Cl.
CPC .. *A61K 39/145* (2013.01); *A61K 2039/55505* (2013.01); *A61K 2039/55566* (2013.01)
(58) Field of Classification Search
None
See application file for complete search history.

(56) References Cited

U.S. PATENT DOCUMENTS

2012/0207760 A1    8/2012    Grandea, III et al.

FOREIGN PATENT DOCUMENTS

| CN | 103384531 A | 11/2013 |
|---|---|---|
| CN | 104195113 A | 12/2014 |
| JP | 2011-528223 A | 11/2011 |
| JP | 2013-540701 A | 11/2013 |
| WO | WO 2010/006452 A1 | 1/2010 |
| WO | WO 2010/060430 A2 | 6/2010 |
| WO | WO 2012/021786 A2 | 2/2012 |
| WO | WO 2012088428 A1 | 6/2012 |

OTHER PUBLICATIONS

GenBank accession ABO37609, hemagglutinin, partial [Influenza A virus (A/Wisconsin/67/X-161/2005(H3))], 2016.*
Zost et al., Contemporary H3N2 influenza viruses have a glycosylation site that alters binding of antibodies elicited by egg-adapted vaccine strains, PNAS, 2017, vol. 114, No. 47, pp. 12578-12583.*
PCT/CN2018/109589, Jan. 15, 2019, International Search Report and Written Opinion.
International Preliminary Report on Patentability for Application No. PCT/CN2018/109589, dated Apr. 30, 2020.
International Search Report and Written Opinion dated Jan. 15, 2019 in connection with International Application No. PCT/CN2018/109589.
Tate et al., Glycosylation of the hemagglutinin modulates the sensitivity of H3N2 influenza viruses to innate proteins in airway secretions and virulence in mice. Virology. Apr. 25, 2011;413(1):84-92. doi: 10.1016/j.virol.2011.01.036. Epub Feb. 24, 2011.
PCT/CN2018/109589, Apr. 30, 2020, International Preliminary Report on Patentability.
Hervé et al., Addition of N-glycosylation sites on the globular head of the H5 hemagglutinin induces the escape of highly pathogenic avian influenza A H5N1 viruses from vaccine-induced immunity. Virology. Dec. 2015;486:134-45. doi: 10.1016/j.virol.2015.08.033. Epub Oct. 1, 2015.
Li et al., Selection of antigenically advanced variants of seasonal influenza viruses. Nat Microbiol. May 23, 2016;1(6):16058. doi: 10.1038/nmicrobiol.2016.58.

* cited by examiner

*Primary Examiner* — Benjamin P Blumel
(74) *Attorney, Agent, or Firm* — Wolf, Greenfield & Sacks, P.C.

(57) ABSTRACT

The disclosure relates to a mutant of hemagglutinin protein of H3N2 subtype influenza virus and use thereof. In addition, the disclosure also relates to a pharmaceutical composition (e.g., a vaccine) comprising the mutant, a method for preparing the mutant, and a method of using the mutant for prevention and/or treatment of an infection of influenza virus and/or a disease (e.g., an influenza) caused by the infection.

13 Claims, 12 Drawing Sheets
Specification includes a Sequence Listing.

Virus for Challenging
A/Beijing/32/1992 (H3N2 subtype)

Virus for Challenging
A/Aichi/02/1968 (H3N2 subtype)

SEQUENCE LISTING

```
<160> NUMBER OF SEQ ID NOS: 13

<210> SEQ ID NO 1
<211> LENGTH: 550
<212> TYPE: PRT
<213> ORGANISM: Influenza A virus

<400> SEQUENCE: 1

Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
                20                  25                  30

Gln Ile Glu Val Thr Asn Ala Thr Glu Leu Val Gln Ser Ser Ser Thr
            35                  40                  45

Gly Gly Ile Cys Asp Ser Pro His Gln Ile Leu Asp Gly Glu Asn Cys
        50                  55                  60

Thr Leu Ile Asp Ala Leu Leu Gly Asp Pro Gln Cys Asp Gly Phe Gln
65                  70                  75                  80

Asn Lys Lys Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
                100                 105                 110

Ala Ser Ser Gly Thr Leu Glu Phe Asn Asp Glu Ser Phe Asn Trp Thr
            115                 120                 125

Gly Val Thr Gln Asn Gly Thr Ser Ser Ser Cys Lys Arg Arg Ser Asn
        130                 135                 140

Asn Ser Phe Phe Ser Arg Leu Asn Trp Leu Thr Gln Leu Lys Phe Lys
145                 150                 155                 160

Tyr Pro Ala Leu Asn Val Thr Met Pro Asn Asn Glu Lys Phe Asp Lys
                165                 170                 175

Leu Tyr Ile Trp Gly Val His His Pro Val Thr Asp Asn Asp Gln Ile
                180                 185                 190

Phe Leu Tyr Ala Gln Ala Ser Gly Arg Ile Thr Val Ser Thr Lys Arg
            195                 200                 205

Ser Gln Gln Thr Val Ile Pro Asn Ile Gly Ser Arg Pro Arg Ile Arg
        210                 215                 220

Asn Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
```

```
                    245                 250                 255
Tyr Phe Lys Ile Arg Ser Gly Lys Ser Ser Ile Met Arg Ser Asp Ala
                260                 265                 270

Pro Ile Gly Lys Cys Asn Ser Glu Cys Ile Thr Pro Asn Gly Ser Ile
            275                 280                 285

Pro Asn Asp Lys Pro Phe Gln Asn Val Asn Arg Ile Thr Tyr Gly Ala
        290                 295                 300

Cys Pro Arg Tyr Val Lys Gln Asn Thr Leu Lys Leu Ala Thr Gly Met
305                 310                 315                 320

Arg Asn Val Pro Glu Lys Gln Thr Arg Gly Ile Phe Gly Ala Ile Ala
                325                 330                 335

Gly Phe Ile Glu Asn Gly Trp Glu Gly Met Val Asp Gly Trp Tyr Gly
            340                 345                 350

Phe Arg His Gln Asn Ser Glu Gly Ile Gly Gln Ala Ala Asp Leu Lys
        355                 360                 365

Ser Thr Gln Ala Ala Ile Asn Gln Ile Asn Gly Lys Leu Asn Arg Leu
370                 375                 380

Ile Gly Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
        435                 440                 445

Glu Arg Thr Lys Lys Gln Leu Arg Glu Asn Ala Glu Asp Met Gly Asn
450                 455                 460

Gly Cys Phe Lys Ile Tyr His Lys Cys Asp Asn Ala Cys Ile Gly Ser
465                 470                 475                 480

Ile Arg Asn Gly Thr Tyr Asp His Asp Val Tyr Arg Asp Glu Ala Leu
                485                 490                 495

Asn Asn Arg Phe Gln Ile Lys Gly Val Glu Leu Lys Ser Gly Tyr Lys
            500                 505                 510

Asp Trp Ile Leu Trp Ile Ser Phe Ala Ile Ser Cys Phe Leu Leu Cys
        515                 520                 525

Val Ala Leu Leu Gly Phe Ile Met Trp Ala Cys Gln Lys Gly Asn Ile
    530                 535                 540

Arg Cys Asn Ile Cys Ile
545                 550

<210> SEQ ID NO 2
<211> LENGTH: 540
<212> TYPE: PRT
<213> ORGANISM: Artificial Sequence
<220> FEATURE:
<223> OTHER INFORMATION: WI2005-WT-HA

<400> SEQUENCE: 2

Met Ala Thr Leu Cys Leu Gly His His Ala Val Pro Asn Gly Thr Ile
1               5                   10                  15

Val Lys Thr Ile Thr Asn Asp Gln Ile Glu Val Thr Asn Ala Thr Glu
                20                  25                  30

Leu Val Gln Ser Ser Ser Thr Gly Gly Ile Cys Asp Ser Pro His Gln
            35                  40                  45

Ile Leu Asp Gly Glu Asn Cys Thr Leu Ile Asp Ala Leu Leu Gly Asp
```

```
            50                  55                  60
Pro Gln Cys Asp Gly Phe Gln Asn Lys Trp Asp Leu Phe Val Glu
 65                  70                  75                  80

Arg Ser Lys Ala Tyr Ser Asn Cys Tyr Pro Tyr Asp Val Pro Asp Tyr
                     85                  90                  95

Ala Ser Leu Arg Ser Leu Val Ala Ser Ser Gly Thr Leu Glu Phe Asn
                100                 105                 110

Asp Glu Ser Phe Asn Trp Thr Gly Val Thr Gln Asn Gly Thr Ser Ser
                115                 120                 125

Ser Cys Lys Arg Arg Ser Asn Asn Ser Phe Phe Ser Arg Leu Asn Trp
            130                 135                 140

Leu Thr Gln Leu Lys Phe Lys Tyr Pro Ala Leu Asn Val Thr Met Pro
145                 150                 155                 160

Asn Asn Glu Lys Phe Asp Lys Leu Tyr Ile Trp Gly Val His His Pro
                165                 170                 175

Val Thr Asp Asn Asp Gln Ile Phe Leu Tyr Ala Gln Ala Ser Gly Arg
                180                 185                 190

Ile Thr Val Ser Thr Lys Arg Ser Gln Gln Thr Val Ile Pro Asn Ile
                195                 200                 205

Gly Ser Arg Pro Arg Ile Arg Asn Ile Pro Ser Arg Ile Ser Ile Tyr
210                 215                 220

Trp Thr Ile Val Lys Pro Gly Asp Ile Leu Leu Ile Asn Ser Thr Gly
225                 230                 235                 240

Asn Leu Ile Ala Pro Arg Gly Tyr Phe Lys Ile Arg Ser Gly Lys Ser
                245                 250                 255

Ser Ile Met Arg Ser Asp Ala Pro Ile Gly Lys Cys Asn Ser Glu Cys
                260                 265                 270

Ile Thr Pro Asn Gly Ser Ile Pro Asn Asp Lys Pro Phe Gln Asn Val
                275                 280                 285

Asn Arg Ile Thr Tyr Gly Ala Cys Pro Arg Tyr Val Lys Gln Asn Thr
            290                 295                 300

Leu Lys Leu Ala Thr Gly Met Arg Asn Val Pro Glu Lys Gln Thr Arg
305                 310                 315                 320

Gly Ile Phe Gly Ala Ile Ala Gly Phe Ile Glu Asn Gly Trp Glu Gly
                325                 330                 335

Met Val Asp Gly Trp Tyr Gly Phe Arg His Gln Asn Ser Glu Gly Ile
                340                 345                 350

Gly Gln Ala Ala Asp Leu Lys Ser Thr Gln Ala Ala Ile Asn Gln Ile
            355                 360                 365

Asn Gly Lys Leu Asn Arg Leu Ile Gly Lys Thr Asn Glu Lys Phe His
    370                 375                 380

Gln Ile Glu Lys Glu Phe Ser Glu Val Glu Gly Arg Ile Gln Asp Leu
385                 390                 395                 400

Glu Lys Tyr Val Glu Asp Thr Lys Ile Asp Leu Trp Ser Tyr Asn Ala
                405                 410                 415

Glu Leu Leu Val Ala Leu Glu Asn Gln His Thr Ile Asp Leu Thr Asp
                420                 425                 430

Ser Glu Met Asn Lys Leu Phe Glu Arg Thr Lys Lys Gln Leu Arg Glu
            435                 440                 445

Asn Ala Glu Asp Met Gly Asn Gly Cys Phe Lys Ile Tyr His Lys Cys
    450                 455                 460

Asp Asn Ala Cys Ile Gly Ser Ile Arg Asn Gly Thr Tyr Asp His Asp
465                 470                 475                 480
```

Val Tyr Arg Asp Glu Ala Leu Asn Asn Arg Phe Gln Ile Lys Ser Gly
            485                 490                 495

Arg Leu Val Pro Arg Gly Ser Pro Gly Ser Gly Tyr Ile Pro Glu Ala
            500                 505                 510

Pro Arg Asp Gly Gln Ala Tyr Val Arg Lys Asp Gly Glu Trp Val Leu
            515                 520                 525

Leu Ser Thr Phe Leu Gly His His His His His
            530                 535                 540

<210> SEQ ID NO 3
<211> LENGTH: 540
<212> TYPE: PRT
<213> ORGANISM: Artificial Sequence
<220> FEATURE:
<223> OTHER INFORMATION: HA-mut1

<400> SEQUENCE: 3

Met Ala Thr Leu Cys Leu Gly His His Ala Val Pro Ala Gly Thr Ile
1               5                   10                  15

Val Lys Thr Ile Thr Asn Asp Gln Ile Glu Val Thr Ala Ala Thr Glu
            20                  25                  30

Leu Val Gln Ser Ser Ser Thr Gly Gly Ile Cys Asp Ser Pro His Gln
        35                  40                  45

Ile Leu Asp Gly Glu Ala Cys Thr Leu Ile Asp Ala Leu Leu Gly Asp
    50                  55                  60

Pro Gln Cys Asp Gly Phe Gln Asn Lys Lys Trp Asp Leu Phe Val Glu
65                  70                  75                  80

Arg Ser Lys Ala Tyr Ser Asn Cys Tyr Pro Tyr Asp Val Pro Asp Tyr
                85                  90                  95

Ala Ser Leu Arg Ser Leu Val Ala Ser Ser Gly Thr Leu Glu Phe Asn
            100                 105                 110

Asp Glu Ser Phe Ala Trp Thr Gly Val Thr Gln Ala Gly Thr Ser Ser
        115                 120                 125

Ser Cys Lys Arg Arg Ser Ala Asn Ser Phe Phe Ser Arg Leu Asn Trp
    130                 135                 140

Leu Thr Gln Leu Lys Phe Lys Tyr Pro Ala Leu Ala Val Thr Met Pro
145                 150                 155                 160

Asn Asn Glu Lys Phe Asp Lys Leu Tyr Ile Trp Gly Val His His Pro
                165                 170                 175

Val Thr Asp Asn Asp Gln Ile Phe Leu Tyr Ala Gln Ala Ser Gly Arg
            180                 185                 190

Ile Thr Val Ser Thr Lys Arg Ser Gln Gln Thr Val Ile Pro Asn Ile
        195                 200                 205

Gly Ser Arg Pro Arg Ile Arg Asn Ile Pro Ser Arg Ile Ser Ile Tyr
    210                 215                 220

Trp Thr Ile Val Lys Pro Gly Asp Ile Leu Leu Ile Ala Ser Thr Gly
225                 230                 235                 240

Asn Leu Ile Ala Pro Arg Gly Tyr Phe Lys Ile Arg Ser Gly Lys Ser
                245                 250                 255

Ser Ile Met Arg Ser Asp Ala Pro Ile Gly Lys Cys Asn Ser Glu Cys
            260                 265                 270

Ile Thr Pro Ala Gly Ser Ile Pro Asn Asp Lys Pro Phe Gln Asn Val
        275                 280                 285

Asn Arg Ile Thr Tyr Gly Ala Cys Pro Arg Tyr Val Lys Gln Asn Thr
    290                 295                 300

```
Leu Lys Leu Ala Thr Gly Met Arg Asn Val Pro Glu Lys Gln Thr Arg
305                 310                 315                 320

Gly Ile Phe Gly Ala Ile Ala Gly Phe Ile Glu Asn Gly Trp Glu Gly
            325                 330                 335

Met Val Asp Gly Trp Tyr Gly Phe Arg His Gln Asn Ser Glu Gly Ile
        340                 345                 350

Gly Gln Ala Ala Asp Leu Lys Ser Thr Gln Ala Ala Ile Asn Gln Ile
    355                 360                 365

Asn Gly Lys Leu Asn Arg Leu Ile Gly Lys Thr Asn Glu Lys Phe His
370                 375                 380

Gln Ile Glu Lys Glu Phe Ser Glu Val Glu Gly Arg Ile Gln Asp Leu
385                 390                 395                 400

Glu Lys Tyr Val Glu Asp Thr Lys Ile Asp Leu Trp Ser Tyr Asn Ala
            405                 410                 415

Glu Leu Leu Val Ala Leu Glu Asn Gln His Thr Ile Asp Leu Thr Asp
        420                 425                 430

Ser Glu Met Asn Lys Leu Phe Glu Arg Thr Lys Lys Gln Leu Arg Glu
    435                 440                 445

Asn Ala Glu Asp Met Gly Asn Gly Cys Phe Lys Ile Tyr His Lys Cys
450                 455                 460

Asp Asn Ala Cys Ile Gly Ser Ile Arg Ala Gly Thr Tyr Asp His Asp
465                 470                 475                 480

Val Tyr Arg Asp Glu Ala Leu Asn Asn Arg Phe Gln Ile Lys Ser Gly
            485                 490                 495

Arg Leu Val Pro Arg Gly Ser Pro Gly Ser Gly Tyr Ile Pro Glu Ala
        500                 505                 510

Pro Arg Asp Gly Gln Ala Tyr Val Arg Lys Asp Gly Glu Trp Val Leu
    515                 520                 525

Leu Ser Thr Phe Leu Gly His His His His His
530                 535                 540

<210> SEQ ID NO 4
<211> LENGTH: 540
<212> TYPE: PRT
<213> ORGANISM: Artificial Sequence
<220> FEATURE:
<223> OTHER INFORMATION: HA-mut2

<400> SEQUENCE: 4

Met Ala Thr Leu Cys Leu Gly His His Ala Val Pro Asn Gly Thr Ile
1               5                   10                  15

Val Lys Thr Ile Thr Asn Asp Gln Ile Glu Val Thr Asn Ala Thr Glu
            20                  25                  30

Leu Val Gln Ser Ser Thr Gly Gly Ile Cys Asp Ser Pro His Gln
        35                  40                  45

Ile Leu Asp Gly Glu Ala Cys Thr Leu Ile Asp Ala Leu Leu Gly Asp
    50                  55                  60

Pro Gln Cys Asp Gly Phe Gln Asn Lys Lys Trp Asp Leu Phe Val Glu
65                  70                  75                  80

Arg Ser Lys Ala Tyr Ser Asn Cys Tyr Pro Tyr Asp Val Pro Asp Tyr
            85                  90                  95

Ala Ser Leu Arg Ser Leu Val Ala Ser Ser Gly Thr Leu Glu Phe Asn
        100                 105                 110

Asp Glu Ser Phe Ala Trp Thr Gly Val Thr Gln Ala Gly Thr Ser Ser
    115                 120                 125
```

```
Ser Cys Lys Arg Arg Ser Ala Asn Ser Phe Phe Ser Arg Leu Asn Trp
130                 135                 140

Leu Thr Gln Leu Lys Phe Lys Tyr Pro Ala Leu Ala Val Thr Met Pro
145                 150                 155                 160

Asn Asn Glu Lys Phe Asp Lys Leu Tyr Ile Trp Gly Val His His Pro
                165                 170                 175

Val Thr Asp Asn Asp Gln Ile Phe Leu Tyr Ala Gln Ala Ser Gly Arg
            180                 185                 190

Ile Thr Val Ser Thr Lys Arg Ser Gln Gln Thr Val Ile Pro Asn Ile
        195                 200                 205

Gly Ser Arg Pro Arg Ile Arg Asn Ile Pro Ser Arg Ile Ser Ile Tyr
    210                 215                 220

Trp Thr Ile Val Lys Pro Gly Asp Ile Leu Leu Ile Ala Ser Thr Gly
225                 230                 235                 240

Asn Leu Ile Ala Pro Arg Gly Tyr Phe Lys Ile Arg Ser Gly Lys Ser
                245                 250                 255

Ser Ile Met Arg Ser Asp Ala Pro Ile Gly Lys Cys Asn Ser Glu Cys
            260                 265                 270

Ile Thr Pro Asn Gly Ser Ile Pro Asn Asp Lys Pro Phe Gln Asn Val
        275                 280                 285

Asn Arg Ile Thr Tyr Gly Ala Cys Pro Arg Tyr Val Lys Gln Asn Thr
    290                 295                 300

Leu Lys Leu Ala Thr Gly Met Arg Asn Val Pro Glu Lys Gln Thr Arg
305                 310                 315                 320

Gly Ile Phe Gly Ala Ile Ala Gly Phe Ile Glu Asn Gly Trp Glu Gly
                325                 330                 335

Met Val Asp Gly Trp Tyr Gly Phe Arg His Gln Asn Ser Glu Gly Ile
            340                 345                 350

Gly Gln Ala Ala Asp Leu Lys Ser Thr Gln Ala Ala Ile Asn Gln Ile
        355                 360                 365

Asn Gly Lys Leu Asn Arg Leu Ile Gly Lys Thr Asn Glu Lys Phe His
    370                 375                 380

Gln Ile Glu Lys Glu Phe Ser Glu Val Glu Gly Arg Ile Gln Asp Leu
385                 390                 395                 400

Glu Lys Tyr Val Glu Asp Thr Lys Ile Asp Leu Trp Ser Tyr Asn Ala
                405                 410                 415

Glu Leu Leu Val Ala Leu Glu Asn Gln His Thr Ile Asp Leu Thr Asp
            420                 425                 430

Ser Glu Met Asn Lys Leu Phe Glu Arg Thr Lys Lys Gln Leu Arg Glu
        435                 440                 445

Asn Ala Glu Asp Met Gly Asn Gly Cys Phe Lys Ile Tyr His Lys Cys
    450                 455                 460

Asp Asn Ala Cys Ile Gly Ser Ile Arg Asn Gly Thr Tyr Asp His Asp
465                 470                 475                 480

Val Tyr Arg Asp Glu Ala Leu Asn Asn Arg Phe Gln Ile Lys Ser Gly
                485                 490                 495

Arg Leu Val Pro Arg Gly Ser Pro Gly Ser Gly Tyr Ile Pro Glu Ala
            500                 505                 510

Pro Arg Asp Gly Gln Ala Tyr Val Arg Lys Asp Gly Glu Trp Val Leu
        515                 520                 525

Leu Ser Thr Phe Leu Gly His His His His His
        530                 535                 540
```

```
<210> SEQ ID NO 5
<211> LENGTH: 540
<212> TYPE: PRT
<213> ORGANISM: Artificial Sequence
<220> FEATURE:
<223> OTHER INFORMATION: HA-mut3

<400> SEQUENCE: 5

Met Ala Thr Leu Cys Leu Gly His His Ala Val Pro Ala Gly Thr Ile
1               5                   10                  15

Val Lys Thr Ile Thr Asn Asp Gln Ile Glu Val Thr Ala Ala Thr Glu
            20                  25                  30

Leu Val Gln Ser Ser Thr Gly Gly Ile Cys Asp Ser Pro His Gln
        35                  40                  45

Ile Leu Asp Gly Glu Asn Cys Thr Leu Ile Asp Ala Leu Leu Gly Asp
    50                  55                  60

Pro Gln Cys Asp Gly Phe Gln Asn Lys Lys Trp Asp Leu Phe Val Glu
65                  70                  75                  80

Arg Ser Lys Ala Tyr Ser Asn Cys Tyr Pro Tyr Asp Val Pro Asp Tyr
                85                  90                  95

Ala Ser Leu Arg Ser Leu Val Ala Ser Ser Gly Thr Leu Glu Phe Asn
            100                 105                 110

Asp Glu Ser Phe Asn Trp Thr Gly Val Thr Gln Asn Gly Thr Ser Ser
        115                 120                 125

Ser Cys Lys Arg Arg Ser Asn Asn Ser Phe Phe Ser Arg Leu Asn Trp
    130                 135                 140

Leu Thr Gln Leu Lys Phe Lys Tyr Pro Ala Leu Asn Val Thr Met Pro
145                 150                 155                 160

Asn Asn Glu Lys Phe Asp Lys Leu Tyr Ile Trp Gly Val His His Pro
                165                 170                 175

Val Thr Asp Asn Asp Gln Ile Phe Leu Tyr Ala Gln Ala Ser Gly Arg
            180                 185                 190

Ile Thr Val Ser Thr Lys Arg Ser Gln Gln Thr Val Ile Pro Asn Ile
        195                 200                 205

Gly Ser Arg Pro Arg Ile Arg Asn Ile Pro Ser Arg Ile Ser Ile Tyr
    210                 215                 220

Trp Thr Ile Val Lys Pro Gly Asp Ile Leu Leu Ile Asn Ser Thr Gly
225                 230                 235                 240

Asn Leu Ile Ala Pro Arg Gly Tyr Phe Lys Ile Arg Ser Gly Lys Ser
                245                 250                 255

Ser Ile Met Arg Ser Asp Ala Pro Ile Gly Lys Cys Asn Ser Glu Cys
            260                 265                 270

Ile Thr Pro Ala Gly Ser Ile Pro Asn Asp Lys Pro Phe Gln Asn Val
        275                 280                 285

Asn Arg Ile Thr Tyr Gly Ala Cys Pro Arg Tyr Val Lys Gln Asn Thr
    290                 295                 300

Leu Lys Leu Ala Thr Gly Met Arg Asn Val Pro Glu Lys Gln Thr Arg
305                 310                 315                 320

Gly Ile Phe Gly Ala Ile Ala Gly Phe Ile Glu Asn Gly Trp Glu Gly
                325                 330                 335

Met Val Asp Gly Trp Tyr Gly Phe Arg His Gln Asn Ser Glu Gly Ile
            340                 345                 350

Gly Gln Ala Ala Asp Leu Lys Ser Thr Gln Ala Ala Ile Asn Gln Ile
        355                 360                 365
```

```
Asn Gly Lys Leu Asn Arg Leu Ile Gly Lys Thr Asn Glu Lys Phe His
    370                 375                 380
Gln Ile Glu Lys Glu Phe Ser Glu Val Glu Gly Arg Ile Gln Asp Leu
385                 390                 395                 400
Glu Lys Tyr Val Glu Asp Thr Lys Ile Asp Leu Trp Ser Tyr Asn Ala
                405                 410                 415
Glu Leu Leu Val Ala Leu Glu Asn Gln His Thr Ile Asp Leu Thr Asp
                420                 425                 430
Ser Glu Met Asn Lys Leu Phe Glu Arg Thr Lys Lys Gln Leu Arg Glu
            435                 440                 445
Asn Ala Glu Asp Met Gly Asn Gly Cys Phe Lys Ile Tyr His Lys Cys
450                 455                 460
Asp Asn Ala Cys Ile Gly Ser Ile Arg Ala Gly Thr Tyr Asp His Asp
465                 470                 475                 480
Val Tyr Arg Asp Glu Ala Leu Asn Asn Arg Phe Gln Ile Lys Ser Gly
                485                 490                 495
Arg Leu Val Pro Arg Gly Ser Pro Gly Ser Tyr Ile Pro Glu Ala
                500                 505                 510
Pro Arg Asp Gly Gln Ala Tyr Val Arg Lys Asp Gly Glu Trp Val Leu
            515                 520                 525
Leu Ser Thr Phe Leu Gly His His His His His His
530                 535                 540

<210> SEQ ID NO 6
<211> LENGTH: 565
<212> TYPE: PRT
<213> ORGANISM: Influenza A virus

<400> SEQUENCE: 6

Lys Thr Ile Ile Ala Leu Ser Tyr Ile Leu Cys Leu Val Phe Ala Gln
1               5                   10                  15
Lys Ile Pro Gly Asn Asp Asn Ser Thr Ala Thr Leu Cys Leu Gly His
            20                  25                  30
His Ala Val Pro Asn Gly Thr Ile Val Lys Thr Ile Thr Asn Asp Arg
        35                  40                  45
Ile Glu Val Thr Asn Ala Thr Glu Leu Val Gln Asn Ser Ser Ile Gly
    50                  55                  60
Glu Ile Cys Asp Ser Pro His Gln Ile Leu Asp Gly Glu Asn Cys Thr
65                  70                  75                  80
Leu Ile Asp Ala Leu Leu Gly Asp Pro Gln Cys Asp Gly Phe Gln Asn
                85                  90                  95
Lys Lys Trp Asp Leu Phe Val Glu Arg Ser Lys Ala Tyr Ser Asn Cys
            100                 105                 110
Tyr Pro Tyr Asp Val Pro Asp Tyr Ala Ser Leu Arg Ser Leu Val Ala
        115                 120                 125
Ser Ser Gly Thr Leu Glu Phe Asn Asn Glu Ser Phe Asn Trp Thr Gly
    130                 135                 140
Val Thr Gln Asn Gly Thr Ser Ser Ala Cys Ile Arg Arg Ser Ser Ser
145                 150                 155                 160
Ser Phe Phe Ser Arg Leu Asn Trp Leu Thr His Leu Asn Tyr Lys Tyr
                165                 170                 175
Pro Ala Leu Asn Val Thr Met Pro Asn Asn Glu Gln Phe Asp Lys Leu
            180                 185                 190
Tyr Ile Trp Gly Val His His Pro Gly Thr Asp Lys Asp Gln Ile Phe
        195                 200                 205
```

Pro Tyr Ala Gln Ser Ser Gly Arg Ile Ile Val Ser Thr Lys Arg Ser
    210                 215                 220
Gln Gln Ala Val Ile Pro Asn Ile Gly Ser Arg Pro Arg Ile Arg Asp
225                 230                 235                 240
Ile Pro Ser Arg Ile Ser Ile Tyr Trp Thr Ile Val Lys Pro Gly Asp
                245                 250                 255
Ile Leu Leu Ile Asn Ser Thr Gly Asn Leu Ile Ala Pro Arg Gly Tyr
            260                 265                 270
Phe Lys Leu Arg Ser Gly Lys Ser Ser Ile Met Arg Ser Asp Ala Pro
        275                 280                 285
Ile Gly Lys Cys Lys Ser Glu Cys Ile Thr Pro Asn Gly Ser Ile Pro
    290                 295                 300
Asn Asp Lys Pro Phe Gln Asn Val Asn Arg Ile Thr Tyr Gly Ala Cys
305                 310                 315                 320
Pro Arg Tyr Val Lys His Ser Thr Leu Lys Leu Ala Thr Gly Met Arg
                325                 330                 335
Asn Val Pro Glu Lys Gln Thr Arg Gly Ile Phe Gly Ala Ile Ala Gly
            340                 345                 350
Phe Ile Glu Asn Gly Trp Glu Gly Met Val Asp Gly Trp Tyr Gly Phe
        355                 360                 365
Arg His Gln Asn Ser Glu Gly Arg Gly Gln Ala Ala Asp Leu Lys Ser
    370                 375                 380
Thr Gln Ala Ala Ile Asp Gln Ile Asn Gly Lys Leu Asn Arg Leu Ile
385                 390                 395                 400
Gly Lys Thr Asn Glu Lys Phe His Gln Ile Glu Lys Glu Phe Ser Glu
                405                 410                 415
Val Glu Gly Arg Ile Gln Asp Leu Glu Lys Tyr Val Glu Asp Thr Lys
            420                 425                 430
Ile Asp Leu Trp Ser Tyr Asn Ala Glu Leu Leu Val Ala Leu Glu Asn
        435                 440                 445
Gln His Thr Ile Asp Leu Thr Asp Ser Glu Met Asn Lys Leu Phe Glu
    450                 455                 460
Lys Thr Lys Lys Gln Leu Arg Glu Asn Ala Glu Asp Met Gly Asn Gly
465                 470                 475                 480
Cys Phe Lys Ile Tyr His Lys Cys Asp Asn Ala Cys Ile Gly Ser Ile
                485                 490                 495
Arg Asn Gly Thr Tyr Asp His Asn Val Tyr Arg Asp Glu Ala Leu Asn
            500                 505                 510
Asn Arg Phe Gln Ile Lys Gly Val Glu Leu Lys Ser Gly Tyr Lys Asp
        515                 520                 525
Trp Ile Leu Trp Ile Ser Phe Ala Ile Ser Cys Phe Leu Leu Cys Val
    530                 535                 540
Ala Leu Leu Gly Phe Ile Met Trp Ala Cys Gln Lys Gly Asn Ile Arg
545                 550                 555                 560
Cys Asn Ile Cys Ile
                565

<210> SEQ ID NO 7
<211> LENGTH: 540
<212> TYPE: PRT
<213> ORGANISM: Artificial Sequence
<220> FEATURE:
<223> OTHER INFORMATION: HK2014-WT-HA

<400> SEQUENCE: 7

```
Met Ala Thr Leu Cys Leu Gly His His Ala Val Pro Asn Gly Thr Ile
1               5                   10                  15

Val Lys Thr Ile Thr Asn Asp Arg Ile Glu Val Thr Asn Ala Thr Glu
                20                  25                  30

Leu Val Gln Asn Ser Ser Ile Gly Glu Ile Cys Asp Ser Pro His Gln
            35                  40                  45

Ile Leu Asp Gly Glu Asn Cys Thr Leu Ile Asp Ala Leu Leu Gly Asp
50                  55                  60

Pro Gln Cys Asp Gly Phe Gln Asn Lys Lys Trp Asp Leu Phe Val Glu
65                  70                  75                  80

Arg Ser Lys Ala Tyr Ser Asn Cys Tyr Pro Tyr Asp Val Pro Asp Tyr
                85                  90                  95

Ala Ser Leu Arg Ser Leu Val Ala Ser Ser Gly Thr Leu Glu Phe Asn
                100                 105                 110

Asn Glu Ser Phe Asn Trp Thr Gly Val Thr Gln Asn Gly Thr Ser Ser
            115                 120                 125

Ala Cys Ile Arg Arg Ser Ser Ser Phe Phe Ser Arg Leu Asn Trp
130                 135                 140

Leu Thr His Leu Asn Tyr Lys Tyr Pro Ala Leu Asn Val Thr Met Pro
145                 150                 155                 160

Asn Asn Glu Gln Phe Asp Lys Leu Tyr Ile Trp Gly Val His His Pro
                165                 170                 175

Gly Thr Asp Lys Asp Gln Ile Phe Pro Tyr Ala Gln Ser Ser Gly Arg
                180                 185                 190

Ile Ile Val Ser Thr Lys Arg Ser Gln Gln Ala Val Ile Pro Asn Ile
                195                 200                 205

Gly Ser Arg Pro Arg Ile Arg Asp Ile Pro Ser Arg Ile Ser Ile Tyr
                210                 215                 220

Trp Thr Ile Val Lys Pro Gly Asp Ile Leu Leu Ile Asn Ser Thr Gly
225                 230                 235                 240

Asn Leu Ile Ala Pro Arg Gly Tyr Phe Lys Leu Arg Ser Gly Lys Ser
                245                 250                 255

Ser Ile Met Arg Ser Asp Ala Pro Ile Gly Lys Cys Lys Ser Glu Cys
                260                 265                 270

Ile Thr Pro Asn Gly Ser Ile Pro Asn Asp Lys Pro Phe Gln Asn Val
                275                 280                 285

Asn Arg Ile Thr Tyr Gly Ala Cys Pro Arg Tyr Val Lys His Ser Thr
                290                 295                 300

Leu Lys Leu Ala Thr Gly Met Arg Asn Val Pro Glu Lys Gln Thr Arg
305                 310                 315                 320

Gly Ile Phe Gly Ala Ile Ala Gly Phe Ile Glu Asn Gly Trp Glu Gly
                325                 330                 335

Met Val Asp Gly Trp Tyr Gly Phe Arg His Gln Asn Ser Glu Gly Arg
                340                 345                 350

Gly Gln Ala Ala Asp Leu Lys Ser Thr Gln Ala Ala Ile Asp Gln Ile
                355                 360                 365

Asn Gly Lys Leu Asn Arg Leu Ile Gly Lys Thr Asn Glu Lys Phe His
                370                 375                 380

Gln Ile Glu Lys Glu Phe Ser Glu Val Glu Gly Arg Ile Gln Asp Leu
385                 390                 395                 400

Glu Lys Tyr Val Glu Asp Thr Lys Ile Asp Leu Trp Ser Tyr Asn Ala
                405                 410                 415
```

```
Glu Leu Leu Val Ala Leu Glu Asn Gln His Thr Ile Asp Leu Thr Asp
            420                 425                 430

Ser Glu Met Asn Lys Leu Phe Glu Lys Thr Lys Lys Gln Leu Arg Glu
    435                 440                 445

Asn Ala Glu Asp Met Gly Asn Gly Cys Phe Lys Ile Tyr His Lys Cys
450                 455                 460

Asp Asn Ala Cys Ile Gly Ser Ile Arg Asn Gly Thr Tyr Asp His Asn
465                 470                 475                 480

Val Tyr Arg Asp Glu Ala Leu Asn Asn Arg Phe Gln Ile Lys Ser Gly
                485                 490                 495

Arg Leu Val Pro Arg Gly Ser Pro Gly Ser Gly Tyr Ile Pro Glu Ala
            500                 505                 510

Pro Arg Asp Gly Gln Ala Tyr Val Arg Lys Asp Gly Glu Trp Val Leu
        515                 520                 525

Leu Ser Thr Phe Leu Gly His His His His His His
    530                 535                 540

<210> SEQ ID NO 8
<211> LENGTH: 540
<212> TYPE: PRT
<213> ORGANISM: Artificial Sequence
<220> FEATURE:
<223> OTHER INFORMATION: HK2014-DG-HA

<400> SEQUENCE: 8

Met Ala Thr Leu Cys Leu Gly His His Ala Val Pro Gln Gly Thr Ile
1               5                   10                  15

Val Lys Thr Ile Thr Asn Asp Arg Ile Glu Val Thr Gln Ala Thr Glu
            20                  25                  30

Leu Val Gln Gln Ser Ser Ile Gly Glu Ile Cys Asp Ser Pro His Gln
        35                  40                  45

Ile Leu Asp Gly Glu Gln Cys Thr Leu Ile Asp Ala Leu Leu Gly Asp
    50                  55                  60

Pro Gln Cys Asp Gly Phe Gln Asn Lys Lys Trp Asp Leu Phe Val Glu
65                  70                  75                  80

Arg Ser Lys Ala Tyr Ser Asn Cys Tyr Pro Tyr Asp Val Pro Asp Tyr
                85                  90                  95

Ala Ser Leu Arg Ser Leu Val Ala Ser Ser Gly Thr Leu Glu Phe Asn
            100                 105                 110

Gln Glu Ser Phe Gln Trp Thr Gly Val Thr Gln Gln Gly Thr Ser Ser
        115                 120                 125

Ala Cys Ile Arg Arg Ser Ser Ser Phe Phe Ser Arg Leu Asn Trp
    130                 135                 140

Leu Thr His Leu Asn Tyr Lys Tyr Pro Ala Leu Gln Val Thr Met Pro
145                 150                 155                 160

Asn Asn Glu Gln Phe Asp Lys Leu Tyr Ile Trp Gly Val His Pro
                165                 170                 175

Gly Thr Asp Lys Asp Gln Ile Phe Pro Tyr Ala Gln Ser Ser Gly Arg
            180                 185                 190

Ile Ile Val Ser Thr Lys Arg Ser Gln Gln Ala Val Ile Pro Asn Ile
        195                 200                 205

Gly Ser Arg Pro Arg Ile Arg Asp Ile Pro Ser Arg Ile Ser Ile Tyr
    210                 215                 220

Trp Thr Ile Val Lys Pro Gly Asp Ile Leu Leu Ile Gln Ser Thr Gly
225                 230                 235                 240
```

```
Asn Leu Ile Ala Pro Arg Gly Tyr Phe Lys Leu Arg Ser Gly Lys Ser
                245                 250                 255

Ser Ile Met Arg Ser Asp Ala Pro Ile Gly Lys Cys Lys Ser Glu Cys
        260                 265                 270

Ile Thr Pro Gln Gly Ser Ile Pro Asn Asp Lys Pro Phe Gln Asn Val
        275                 280                 285

Asn Arg Ile Thr Tyr Gly Ala Cys Pro Arg Tyr Val Lys His Ser Thr
        290                 295                 300

Leu Lys Leu Ala Thr Gly Met Arg Asn Val Pro Glu Lys Gln Thr Arg
305                 310                 315                 320

Gly Ile Phe Gly Ala Ile Ala Gly Phe Ile Glu Asn Gly Trp Glu Gly
                325                 330                 335

Met Val Asp Gly Trp Tyr Gly Phe Arg His Gln Asn Ser Glu Gly Arg
            340                 345                 350

Gly Gln Ala Ala Asp Leu Lys Ser Thr Gln Ala Ala Ile Asp Gln Ile
            355                 360                 365

Asn Gly Lys Leu Asn Arg Leu Ile Gly Lys Thr Asn Glu Lys Phe His
        370                 375                 380

Gln Ile Glu Lys Glu Phe Ser Glu Val Glu Gly Arg Ile Gln Asp Leu
385                 390                 395                 400

Glu Lys Tyr Val Glu Asp Thr Lys Ile Asp Leu Trp Ser Tyr Asn Ala
                405                 410                 415

Glu Leu Leu Val Ala Leu Glu Asn Gln His Thr Ile Asp Leu Thr Asp
            420                 425                 430

Ser Glu Met Asn Lys Leu Phe Glu Lys Thr Lys Lys Gln Leu Arg Glu
            435                 440                 445

Asn Ala Glu Asp Met Gly Asn Gly Cys Phe Lys Ile Tyr His Lys Cys
450                 455                 460

Asp Asn Ala Cys Ile Gly Ser Ile Arg Gln Gly Thr Tyr Asp His Asn
465                 470                 475                 480

Val Tyr Arg Asp Glu Ala Leu Asn Asn Arg Phe Gln Ile Lys Ser Gly
                485                 490                 495

Arg Leu Val Pro Arg Gly Ser Pro Gly Ser Gly Tyr Ile Pro Glu Ala
            500                 505                 510

Pro Arg Asp Gly Gln Ala Tyr Val Arg Lys Asp Gly Glu Trp Val Leu
            515                 520                 525

Leu Ser Thr Phe Leu Gly His His His His
        530                 535                 540

<210> SEQ ID NO 9
<211> LENGTH: 38
<212> TYPE: PRT
<213> ORGANISM: Artificial Sequence
<220> FEATURE:
<223> OTHER INFORMATION: signal peptide

<400> SEQUENCE: 9

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala
        35

<210> SEQ ID NO 10
<211> LENGTH: 40
```

<212> TYPE: PRT
<213> ORGANISM: Artificial Sequence
<220> FEATURE:
<223> OTHER INFORMATION: folding motif

<400> SEQUENCE: 10

Ser Gly Arg Leu Val Pro Arg Gly Ser Pro Gly Ser Gly Tyr Ile Pro
1               5                   10                  15

Glu Ala Pro Arg Asp Gly Gln Ala Tyr Val Arg Lys Asp Gly Glu Trp
            20                  25                  30

Val Leu Leu Ser Thr Phe Leu Gly
        35                  40

<210> SEQ ID NO 11
<211> LENGTH: 6
<212> TYPE: PRT
<213> ORGANISM: Artificial Sequence
<220> FEATURE:
<223> OTHER INFORMATION: His tag

<400> SEQUENCE: 11

His His His His His His
1               5

<210> SEQ ID NO 12
<211> LENGTH: 493
<212> TYPE: PRT
<213> ORGANISM: Artificial Sequence
<220> FEATURE:
<223> OTHER INFORMATION: mutant of HA protein of A/WISCONSIN/67/2005
      (H3N2)

<400> SEQUENCE: 12

Ala Thr

```
Ser Arg Pro Arg Ile Arg Asn Ile Pro Ser Arg Ile Ser Ile Tyr Trp
    210             215                 220
Thr Ile Val Lys Pro Gly Asp Ile Leu Leu Ile Ala Ser Thr Gly Asn
225             230                 235                 240
Leu Ile Ala Pro Arg Gly Tyr Phe Lys Ile Arg Ser Gly Lys Ser Ser
                245                 250                 255
Ile Met Arg Ser Asp Ala Pro Ile Gly Lys Cys Asn Ser Glu Cys Ile
                260                 265                 270
Thr Pro Ala Gly Ser Ile Pro Asn Asp Lys Pro Phe Gln Asn Val Asn
                275                 280                 285
Arg Ile Thr Tyr Gly Ala Cys Pro Arg Tyr Val Lys Gln Asn Thr Leu
    290                 295                 300
Lys Leu Ala Thr Gly Met Arg Asn Val Pro Glu Lys Gln Thr Arg Gly
305                 310                 315                 320
Ile Phe Gly Ala Ile Ala Gly Phe Ile Glu Asn Gly Trp Glu Gly Met
                325                 330                 335
Val Asp Gly Trp Tyr Gly Phe Arg His Gln Asn Ser Glu Gly Ile Gly
                340                 345                 350
Gln Ala Ala Asp Leu Lys Ser Thr Gln Ala Ala Ile Asn Gln Ile Asn
                355                 360                 365
Gly Lys Leu Asn Arg Leu Ile Gly Lys Thr Asn Glu Lys Phe His Gln
370                 375                 380
Ile Glu Lys Glu Phe Ser Glu Val Glu Gly Arg Ile Gln Asp Leu Glu
385                 390                 395                 400
Lys Tyr Val Glu Asp Thr Lys Ile Asp Leu Trp Ser Tyr Asn Ala Glu
                405                 410                 415
Leu Leu Val Ala Leu Glu Asn Gln His Thr Ile Asp Leu Thr Asp Ser
                420                 425                 430
Glu Met Asn Lys Leu Phe Glu Arg Thr Lys Lys Gln Leu Arg Glu Asn
    435                 440                 445
Ala Glu Asp Met Gly Asn Gly Cys Phe Lys Ile Tyr His Lys Cys Asp
                450                 455                 460
Asn Ala Cys Ile Gly Ser Ile Arg Ala Gly Thr Tyr Asp His Asp Val
465                 470                 475                 480
Tyr Arg Asp Glu Ala Leu Asn Asn Arg Phe Gln Ile Lys
                485                 490

<210> SEQ ID NO 13
<211> LENGTH: 493
<212> TYPE: PRT
<213> ORGANISM: Artificial Sequence
<220> FEATURE:
<223> OTHER INFORMATION: mutant of HA protein of A/HONG_KONG/4801/2014
      (H3N2)

<400> SEQUENCE: 13

Ala Thr Leu Cys Leu Gly His His Ala Val Pro Gln Gly Thr Ile Val
1               5                   10                  15
Lys Thr Ile Thr Asn Asp Arg Ile Glu Val Thr Gln Ala Thr Glu Leu
                20                  25                  30
Val Gln Gln Ser Ser Ile Gly Glu Ile Cys Asp Ser Pro His Gln Ile
            35                  40                  45
Leu Asp Gly Glu Gln Cys Thr Leu Ile Asp Ala Leu Leu Gly Asp Pro
        50                  55                  60
Gln Cys Asp Gly Phe Gln Asn Lys Lys Trp Asp Leu Phe Val Glu Arg
65                  70                  75                  80
```

-continued

Ser Lys Ala Tyr Ser Asn Cys Tyr Pro Tyr Asp Val Pro Asp Tyr Ala
            85                  90                  95

Ser Leu Arg Ser Leu Val Ala Ser Ser Gly Thr Leu Glu Phe Asn Gln
            100                 105                 110

Glu Ser Phe Gln Trp Thr Gly Val Thr Gln Gln Gly Thr Ser Ser Ala
            115                 120                 125

Cys Ile Arg Arg Ser Ser Ser Ser Phe Phe Ser Arg Leu Asn Trp Leu
            130                 135                 140

Thr His Leu Asn Tyr Lys Tyr Pro Ala Leu Gln Val Thr Met Pro Asn
145                 150                 155                 160

Asn Glu Gln Phe Asp Lys Leu Tyr Ile Trp Gly Val His His Pro Gly
            165                 170                 175

Thr Asp Lys Asp Gln Ile Phe Pro Tyr Ala Gln Ser Ser Gly Arg Ile
            180                 185                 190

Ile Val Ser Thr Lys Arg Ser Gln Gln Ala Val Ile Pro Asn Ile Gly
            195                 200                 205

Ser Arg Pro Arg Ile Arg Asp Ile Pro Ser Arg Ile Ser Ile Tyr Trp
            210                 215                 220

Thr Ile Val Lys Pro Gly Asp Ile Leu Leu Ile Gln Ser Thr Gly Asn
225                 230                 235                 240

Leu Ile Ala Pro Arg Gly Tyr Phe Lys Leu Arg Ser Gly Lys Ser Ser
            245                 250                 255

Ile Met Arg Ser Asp Ala Pro Ile Gly Lys Cys Lys Ser Glu Cys Ile
            260                 265                 270

Thr Pro Gln Gly Ser Ile Pro Asn Asp Lys Pro Phe Gln Asn Val Asn
            275                 280                 285

Arg Ile Thr Tyr Gly Ala Cys Pro Arg Tyr Val Lys His Ser Thr Leu
            290                 295                 300

Lys Leu Ala Thr Gly Met Arg Asn Val Pro Glu Lys Gln Thr Arg Gly
305                 310                 315                 320

Ile Phe Gly Ala Ile Ala Gly Phe Ile Glu Asn Gly Trp Glu Gly Met
            325                 330                 335

Val Asp Gly Trp Tyr Gly Phe Arg His Gln Asn Ser Glu Gly Arg Gly
            340                 345                 350

Gln Ala Ala Asp Leu Lys Ser Thr Gln Ala Ala Ile Asp Gln Ile Asn
            355                 360                 365

Gly Lys Leu Asn Arg Leu Ile Gly Lys Thr Asn Glu Lys Phe His Gln
            370                 375                 380

Ile Glu Lys Glu Phe Ser Glu Val Glu Gly Arg Ile Gln Asp Leu Glu
385                 390                 395                 400

Lys Tyr Val Glu Asp Thr Lys Ile Asp Leu Trp Ser Tyr Asn Ala Glu
            405                 410                 415

Leu Leu Val Ala Leu Glu Asn Gln His Thr Ile Asp Leu Thr Asp Ser
            420                 425                 430

Glu Met Asn Lys Leu Phe Glu Lys Thr Lys Gln Leu Arg Glu Asn
            435                 440                 445

Ala Glu Asp Met Gly Asn Gly Cys Phe Lys Ile Tyr His Lys Cys Asp
450                 455                 460

Asn Ala Cys Ile Gly Ser Ile Arg Gln Gly Thr Tyr Asp His Asn Val
465                 470                 475                 480

Tyr Arg Asp Glu Ala Leu Asn Asn Arg Phe Gln Ile Lys
            485                 490

MUTANT OF HEMAGGLUTININ PROTEIN OF H3N2 SUBTYPE INFLUENZA VIRUS AND USE THEREOF

RELATED APPLICATIONS

This application is a national stage filing under 35 U.S.C. § 371 of International PCT Application, PCT/CN2018/109589, filed Oct. 10, 2018, which claims priority to Chinese Application No. 201710969146.0, filed on Oct. 18, 2017, the entire contents of each of which are incorporated herein by reference.

TECHNICAL FIELD

The present application relates to the fields of virology and immunology. In particular, the present application relates to a mutant of hemagglutinin protein of H3N2 subtype influenza virus and uses thereof. In addition, the present application also relates to a pharmaceutical composition (such as a vaccine) comprising the mutant, a method for preparing the mutant, and a method of using the mutant for prevention and/or treatment of an infection of influenza virus and/or a disease (such as influenza) caused by the infection.

BACKGROUND

Influenza virus is a major threat to human health, and its continuous and rapid antigenic drift makes seasonal influenza widely spread among people. Common human seasonal influenza viruses include seasonal H1N1, seasonal H3N2, and influenza B viruses. According to WHO statistics, seasonal influenza causes at least 250,000 to 500,000 deaths each year (Peter D. C. et al., J Clin Invest. 2008, 118: 3273-3275). In addition, the flu pandemic is still a major threat to humanity. Since the discovery of the influenza virus, there have been five worldwide influenza pandemics in the human history, which have killed tens of millions of people, wherein the Spanish flu outbreak of 1918 killed approximately 20 to 50 million people worldwide. Other major influenza outbreaks in the 20th century include the Asian Flu (H2N2) outbreak in 1957 and the Hong Kong Flu (H3N2) outbreak in 1968, both of which caused serious public health threats and a great human panic (Xu R. et al. Science. 2010, 328: 357-360). In the 21st century, the flu pandemic has not stopped. The pandemic of the new influenza A virus (H1N1), which outbroke in Mexico in 2009 and rapidly spread across the world, once again sounded the alarm to the human society. According to WHO statistics, as of Aug. 6, 2010, a total of 18,449 confirmed deaths were reported in more than 200 countries and regions worldwide (WHO Pandemic (h1n1) 2009-update 112. 6 Aug. 2010). When the influenza virus pandemic ends, the influenza virus often evolves into seasonal influenza and continues to spread, and continues to endanger human health through antigenic drift during the epidemic process. In addition, humans face the threat of highly pathogenic avian influenza. Since 2003, a total of 600 human cases of infection with H5N1 avian influenza virus have been reported worldwide, including 353 deaths and showing a mortality rate of nearly 60% (WHO: http://www.who.int/influenza/human_animal_interface/H5N1_cumulative_table_archives/en/index.html). Since 2013, a total of 1554 cases of human infection with H5N1 avian influenza virus have been reported worldwide, showing a mortality rate of over 25% (WHO: http://www.who.int/influenza/human_animal_interface/H5N1_cumulative_table_archives/en/index.html).

People are worried that once the flu virus spreads among people, it will bring a fatal blow to human society. In short, influenza caused by influenza viruses is a major infectious disease facing human beings.

Influenza virus belongs to Orthomyxoviridae family, influenza virus genus, and is an enveloped virus with single-stranded negative-sense RNA. The genome of an influenza virus encodes more than ten viral proteins. According to the differences in the antigenicity and genetic characteristics of viral nucleoprotein (NP) and matrix protein (M), influenza viruses are classified into 3 types, i.e., type A (A), type B (B) and type C (C) (Horimoto T. et al., Nat Rev Microbiol, 2005, 3 (8): 591-600). Among them, Influenza A Virus (Flu A for short) mutates quickly, has strong pathogenicity, and can cause pandemics worldwide. Influenza B Virus (Flu B for short) mutates slowly and can only cause a local pandemic. Influenza C Virus (Flu C for short) has the slowest mutation and weak pathogenicity, and usually can only infect pregnant women and children with low resistance. Flu A has a wide range of hosts in the nature, besides natural hosts such as waterfowl, it can further cause infections in a variety of animals such as human, horse and pig. Flu A has many subtypes with great variation, and draws great attention in prevention and control of influenza and vaccine research.

Flu A viruses can be classified into a plurality of subtypes according to antigenicity and genetic characteristics of the surface antigen hemagglutinin (HA) and neuraminidase (NA). At present, 18 HA subtypes (H1-H18) and 11 NA subtypes (N1-N11) have been discovered (Tong S. et al., PLoS Pathog. 2013; 9 (10): e1003657). Flu A viruses prevalent in the population mainly involve 2 HA subtypes (H1, H3) and 2 NA subtypes (N1, N2). At the same time, highly pathogenic avian influenza viruses H5N1 and H7N9 also occasionally cause infection in humans and have attracted much attention due to their higher mortality.

Influenza vaccines are the most effective way to fight influenza viruses. Currently, the main target of influenza vaccine-induced antiviral antibodies is hemagglutinin (HA) protein located on viral surface. The HA protein has a trimer structure on viral surface, in which each HA monomer consists of two domains, HA1 and HA2. HA1 is located at the head of the trimer, constitutes a globular structure, contains a receptor binding site, and is a key area for the viral infection in host cells. At present, HA1 is a key target for vaccine design because it contains an important antigenic site that can induce the body to produce a protective neutralizing antibody (Wang T. T. et al., Nat Struct Mol Biol. 2009, 16: 233-234). HA2 is located at the base of the trimer, has a stalk-like structure and contains a fusion peptide, which can mediate the fusion of viral envelope and host cell membrane. It has been reported that some monoclonal antibodies against HA2 can neutralize virus by inhibiting the viral membrane fusion (Wang T. T. et al., Nat Struct Mol Biol. 2009, 16: 233-234).

Influenza viruses have a high variability, among which, especially, HA mutates most rapidly. At present, traditional vaccines mainly target HA protein. Due to the high variability of the HA gene, the vaccine is likely to be ineffective due to antigenic drift. In order to overcome the antigenic variation of the influenza viruses, according to the monitoring of mutations of epidemic virus strains in the previous year, WHO has to make a choice of using the old or establishing a new vaccine strain as a vaccine candidate strain for the epidemic season of the next year, and a new vaccine has to be inoculated every year to ensure the effective protection against the present pandemic strains. In other words, the current influenza vaccines need to be adjusted every year according to the antigenic variation of the virus strains prevalent in the previous year, which is time-consuming and laborious. Therefore, the development of a "broad-spectrum vaccine" that is not affected by virus mutations has gradually become a hotspot of new vaccine research.

Since unmodified natural HA protein as vaccine can only induce a narrow spectrum of immuno-protective effect, it has been proposed to modify the natural HA protein to obtain a vaccine that can induce a broad-spectrum immune response to avoid rapid vaccine failure caused by rapid mutation of HA. However, the HA protein of the influenza virus has many subtypes and has complex post-translational glycosyl modifications, so the research in this area has not made significant progress. There is still a need in the art to develop an HA mutant capable of inducing broad-spectrum anti-influenza-virus protective antibodies in vivo and providing broad-spectrum anti-influenza-virus protection in vivo.

Contents of the Present Invention

HA is a glycoprotein, of which HA1 and HA2 domains both contain glycosylation sites and carry N-linked glycosyl chains (Keil W et al. (1985) EMBO J 4: 2711-2720). In the case of eukaryotic expression (e.g., eukaryotic expression using an insect-baculovirus expression system), the produced HA protein carries N-linked glycosyl chains in both the HA1 and HA2 domains; accordingly, the resulting HA trimer carries N-linked glycosyl chains in its head region and stem region (FIG. 2A). After intensive research, the inventors of the present application found that by modifying the HA protein of H3N2 subtype influenza virus to completely remove the N-linked glycosyl chains carried thereby, the modified HA protein showed an enhanced ability of inducing broad-spectrum protective antibodies, and the protective antibodies induced thereby could recognize more subtypes of influenza viruses and had a broader spectrum protective effect. Based on this, the inventors of the present application have developed a mutant of hemagglutinin protein of H3N2 subtype influenza virus, which does not contain a N-linked glycosylation site (for example, does not contain a characteristic sequence N-X-(S or T)), can induce a broad-spectrum anti-influenza-virus protective antibody in vivo, and can provide a broad-spectrum anti-influenza-virus protective effect in vivo. In particular, the mutant disclosed herein is capable of inducing protective antibodies against different subtypes of influenza viruses, achieves protection against different subtypes of influenza viruses, and therefore can be used as a broad-spectrum vaccine capable of combating multiple subtypes (e.g., at least 2, at least 3 or more subtypes) of influenza viruses, for the prevention and/or treatment of an infection of multiple subtypes (e.g., at least 2, at least 3 or more subtypes) of influenza viruses and a disease (e.g., influenza) associated with the infection.

In particular, the mutant derived from the HA protein of H3N2 subtype influenza virus disclosed in this application not only can induce protective antibodies against multiple strains of H3N2 subtype influenza virus (especially multiple strains of H3N2 subtype influenza virus prevalent in different ages) to achieve protection against multiple strains of H3N2 subtype influenza virus, but also can induce protective antibodies against H7N9 and/or H1N1 subtype influenza virus to achieve protection against H7N9 and/or H1N1 subtype influenza virus. Therefore, such mutant derived from the HA protein of H3N2 subtype influenza virus is particularly suitable to be used as a broad-spectrum vaccine for the prevention and/or treatment of an infection of H3N2, H7N9 and/or H1N1 subtype influenza virus and a disease associated therewith.

As to Mutant

Thus, in one aspect, the present application relates to a mutant of hemagglutinin protein of H3N2 subtype influenza virus, which does not contain an N-linked glycosylation site. Due to the absence of N-linked glycosylation site, such a mutant does not contain a N-linked glycosylation chain. In certain preferred embodiments, the present application provides a mutant of hemagglutinin protein of H3N2 subtype influenza virus, in which as compared with a wild-type hemagglutinin protein of H3N2 subtype influenza virus, the mutant does not contain an N-linked glycosylation site, and, optionally, the mutant does not contain an N-terminal signal peptide and/or a transmembrane region of the wild-type hemagglutinin protein.

N-linked glycosylation is a post-translational modification of a polypeptide, which means that a glycosyl chain is linked to a free —$NH_2$ group on a specific asparagine residue in the polypeptide chain. N-linked glycosylation is usually performed in the endoplasmic reticulum (ER) and Golgi apparatus (GA). Therefore, in certain preferred embodiments, the mutant differs from the wild-type hemagglutinin protein of H3N2 subtype influenza virus at least in that the asparagine residues on each of the N-linked glycosylation sites of the wild-type hemagglutinin protein are independently deleted or substituted with one or more other amino acid residues (e.g., a non-N amino acid residue).

The N-linked glycosylation sites in the influenza virus HA protein can be determined by various known methods (see, Tate M D. Et al., Viruses. 6(3): 1294-316). For example, computer programs or softwares (e.g., the protein sequence analysis software package Antheprot 5.0) can be used to predict and determine N-linked glycosylation sites. In the natural HA protein of influenza virus, the amino acid that undergoes N-linked glycosylation is usually asparagine (N) in a characteristic sequence N-X-(S or T), wherein N represents asparagine, X represents any one amino acid other than proline, S represents serine, and T represents threonine. Therefore, in certain preferred embodiments, the mutant differs from the wild-type hemagglutinin protein of H3N2 subtype influenza virus at least in that the mutant does not contain a characteristic sequence N-X-(S or T); wherein N represents asparagine, X represents any one amino acid other than proline, S represents serine, and T represents threonine. In certain preferred embodiments, the mutant differs from the wild-type hemagglutinin protein of H3N2 subtype influenza virus at least in that each characteristic sequence N-X-(S or T) of the wild-type hemagglutinin protein independently has one or more mutations selected from the group consisting of:

(1) the N residue is deleted or replaced with one or more other amino acid residues (for example, a non-N amino acid residue);

(2) the (S or T) residue is deleted or replaced with one or more other amino acid residues (for example, a non-S and non-T amino acid residue);

(3) the X residue is deleted or replaced with a proline residue;

(4) one or more amino acid residues (for example, a non-N amino acid residue) are added between the N residue and the X residue; and (5) one or more amino acid residues (for example, a non-S and non-T amino acid residue) are added between the X residue and the (S or T) residue;

wherein, N represents asparagine, X represents any one amino acid other than proline, S represents serine, and T represents threonine, thus, the mutant does not contain any characteristic sequence N-X-(S or T).

Each characteristic sequence N-X-(S or T) in the wild-type hemagglutinin protein can be modified independently in various known ways so that the resulting mutant does not contain any characteristic sequence N-X-(S or T).

In certain preferred embodiments, a characteristic sequence N-X-(S or T) in the wild-type hemagglutinin protein can be modified by deleting the N residue or replacing the N residue with one or more other amino acid residues, thereby removing N-glycosylation site. In certain preferred embodiments, a characteristic sequence N-X-(S or T) in the wild-type hemagglutinin protein can be modified by deleting the N residue, thereby removing N-glycosylation site. In certain preferred embodiments, a characteristic sequence N-X-(S or T) in the wild-type hemagglutinin protein can be modified by replacing the N residue with a non-N amino acid residue, thereby removing N-glycosylation site. In certain preferred embodiments, a characteristic sequence N-X-(S or T) in the wild-type hemagglutinin protein can be modified by replacing the N residue with at least two or more (e.g., 2, 3, or 4) amino acid residues, thereby removing N-glycosylation site, provided that the last amino acid residue of the at least two or more amino acid residues is a non-N amino acid residue.

In certain preferred embodiments, a characteristic sequence N-X-(S or T) in the wild-type hemagglutinin protein can be modified by deleting the (S or T) residue or replacing the (S or T) residue with one or more other amino acid residues, thereby removing N-glycosylation site. In certain preferred embodiments, a characteristic sequence N-X-(S or T) in the wild-type hemagglutinin protein can be modified by deleting the (S or T) residue, thereby removing N-glycosylation site. In certain preferred embodiments, the characteristic sequence N-X-(S or T) in the wild-type hemagglutinin protein can be modified by replacing the (S or T) residue with a non-S and non-T amino acid residue, thereby removing N-glycosylation site. In certain preferred embodiments, a characteristic sequence N-X-(S or T) in the wild-type hemagglutinin protein can be modified by replacing the (S or T) residue with at least two or more (e.g., 2, 3, or 4) amino acid residues, thereby removing N-glycosylation site, provided that the first amino acid residue of the at least two or more amino acid residues is non-S and non-T amino acid residue.

In certain preferred embodiments, a characteristic sequence N-X-(S or T) in the wild-type hemagglutinin protein can be modified by deleting the X residue or replacing the X residue with a proline residue, thereby removing N-glycosylation site. In certain preferred embodiments, a characteristic sequence N-X-(S or T) in the wild-type hemagglutinin protein can be modified by deleting the X residue, thereby removing N-glycosylation site. In certain preferred embodiments, a characteristic sequence N-X-(S or T) in the wild-type hemagglutinin protein can be modified by replacing the X residue with a proline residue, thereby removing N-glycosylation site point.

In certain preferred embodiments, a characteristic sequence N-X-(S or T) in the wild-type hemagglutinin protein can be modified by adding one or more amino acid residues between the N residue and the X residue, thereby removing N-glycosylation site. In certain preferred embodiments, a characteristic sequence N-X-(S or T) in the wild-type hemagglutinin protein can be modified by adding a non-N amino acid residue between the N residue and the X residue, thereby removing N-glycosylation site. In certain preferred embodiments, a characteristic sequence N-X-(S or T) in the wild-type hemagglutinin protein can be modified by adding at least two or more (e.g., 2, 3, or 4) amino acid residues between the N residue and the X residue, thereby removing N-glycosylation site, provided that the last amino acid residue of the at least two or more amino acid residues is a non-N amino acid residue.

In certain preferred embodiments, a characteristic sequence N-X-(S or S) in the wild-type hemagglutinin protein can be modified by adding one or more amino acid residues between the X residue and the (S or T) residue, thereby removing N-glycosylation site. In certain preferred embodiments, a characteristic sequence N-X-(S or S) in the wild-type hemagglutinin protein can be modified by adding a non-S and non-T amino acid residue between the X residue and the (S or T) residue, thereby removing N-glycosylation site. In certain preferred embodiments, a characteristic sequence N-X-(S or S) in the wild-type hemagglutinin protein can be modified by adding at least two or more (e.g., 2, 3, or 4) amino acid residues between the N residue and the X residue, thereby removing N-glycosylation site, provided that the first amino acid residue of the at least two or more amino acid residues is non-S and non-T amino acid residue.

In certain preferred embodiments, the mutant differs from the wild-type hemagglutinin protein of influenza virus at least in that the N residue and/or the (S or T) residue of each characteristic sequence N-X-(S or T) in the wild-type hemagglutinin protein is independently deleted or replaced with one or more other amino acid residues (for example, another amino acid residue); wherein N represents asparagine, X represents any one amino acid other than proline, S represents serine, and T represents threonine, so that the mutant does not contain any characteristic sequence N-X-(S or T).

In certain preferred embodiments, the mutant differs from the wild-type hemagglutinin protein of influenza virus at least in that the N residue of each characteristic sequence N-X-(S or T) in the wild-type hemagglutinin protein is independently deleted or replaced with one or more other amino acid residues (for example, a non-N amino acid residue).

In certain preferred embodiments, the wild-type hemagglutinin protein can be modified by deleting the asparagine residue at each N-linked glycosylation site (especially in a characteristic sequence N-X-(S or T)), so that the resulting mutant no longer contains any N-linked glycosylation site and no longer carries any N-linked glycosylation chain. Therefore, in certain preferred embodiments, the mutant differs from the wild-type hemagglutinin protein of influenza virus at least in that the asparagine residue of each characteristic sequence N-X-(S or T) in the wild-type hemagglutinin protein is deleted.

In certain preferred embodiments, the asparagine residue at each N-linked glycosylation site (especially in each characteristic sequence N-X-(S or T)) can be independently replaced with one or more other amino acid residues (for example, a non-N amino acid residue) to modify the wild-type hemagglutinin protein; so that the resulting mutant no longer contains any N-linked glycosylation site and no longer carries any N-linked glycosyl chain. Therefore, in certain preferred embodiments, the mutant differs from the wild-type hemagglutinin protein of influenza virus at least in that each asparagine residue in each characteristic sequence N-X-(S or T) in the wild-type hemagglutinin protein is independently replaced with one or more other amino acid residues (for example, a non-N amino acid residue).

In certain preferred embodiments, the asparagine residues at some N-linked glycosylation sites (especially in a characteristic sequence N-X-(S or T)) can be deleted and the asparagine residues at the remaining N-linked glycosylation sites (especially in a characteristic sequence N-X-(S or T)) are each independently replaced with one or more other amino acid residues (for example, a non-N amino acid residue) to modify the wild-type hemagglutinin protein; so that the resulting mutant no longer contains any N-linked glycosylation site and no longer carries any N-linked glycosylation chain. Therefore, in certain preferred embodiments, the mutant differs from the wild-type hemagglutinin protein of influenza virus at least in that the asparagine residues in some characteristic sequences N-X-(S or T) in the wild-type hemagglutinin protein are deleted, and the asparagine residues in the remaining characteristic sequences N-X-(S or T) are each independently replaced with one or more other amino acid residues (for example, a non-N amino acid residue).

In certain preferred embodiments, the mutant differs from the wild-type hemagglutinin protein of influenza virus at least in that the (S or T) residue in each characteristic sequence N-X-(S or T) in the wild-type hemagglutinin protein is each independently deleted or replaced with one or more other amino acid residues (for example, a non-S and non-T amino acid residue).

In certain preferred embodiments, the (S or T) residue in each characteristic sequence N-X-(S or T) can be deleted to modify the wild-type hemagglutinin protein; so that the resulting mutant no longer contains any N-linked glycosylation site and no longer carries any N-linked glycosylation chain. Therefore, in certain preferred embodiments, the mutant differs from the wild-type hemagglutinin protein of influenza virus at least in that the (S or T) residue in each characteristic sequence N-X-(S or T) in the wild-type hemagglutinin protein is deleted.

In certain preferred embodiments, the (S or T) residue in each characteristic sequence N-X-(S or T) can be each independently replaced with one or more other amino acid residues (for example, a non-S and non-T amino acid residue) to modify the wild-type hemagglutinin protein; so that the resulting mutant no longer contains any N-linked glycosylation site and no longer carries any N-linked glycosyl chain. Therefore, in certain preferred embodiments, the mutant differs from the wild-type hemagglutinin protein of influenza virus at least in that the (S or T) residue in each characteristic sequence N-X-(S or T) in the wild-type hemagglutinin protein is each independently replaced with one or more other amino acid residues (for example, a non-S and non-T amino acid residue).

In certain preferred embodiments, the (S or T) residues in some characteristic sequences N-X-(S or T) can be deleted, and the (S or T) residues in the remaining characteristic sequences N-X-(S or T) are each independently replaced with one or more other amino acid residues (for example, a non-S and non-T amino acid residue) to modify the wild-type hemagglutinin protein; so that the resulting mutant no longer contains any N-linked glycosylation site and no longer carries any N-linked glycosyl chain. Therefore, in certain preferred embodiments, the mutant differs from the wild-type hemagglutinin protein of influenza virus at least in that the (S or T) residues in some characteristic sequences N-X-(S or T) in the wild-type hemagglutinin protein are deleted, and the (S or T) residues in the remaining characteristic sequences N-X-(S or T) are each independently replaced with one or more other amino acid residues (for example, a non-S and non-T amino acid residue).

In certain preferred embodiments, the mutant differs from the wild-type hemagglutinin protein of influenza virus at least in that the N residues in some characteristic sequences N-X-(S or T) in the wild-type hemagglutinin protein are each independently deleted or replaced with one or more other amino acid residues (for example, a non-N amino acid residue); and the (S or T) residues in the remaining characteristic sequences N-X-(S or T) are each independently deleted or replaced with one or more other amino acid residues (for example, a non-S and non-T amino acid residue).

In certain preferred embodiments, the mutant differs from the wild-type hemagglutinin protein of influenza virus at least in that each characteristic sequence N-X-(S or T) of the wild-type hemagglutinin protein independently has a mutation selected from the group consisting of:

(1) the N residue is deleted or replaced with another amino acid residue (for example, a non-N amino acid residue);

(2) the (S or T) residue is deleted or replaced with another amino acid residue (for example, a non-S and non-T amino acid residue);

(3) the X residue is deleted or replaced with a proline residue;

(4) one or more amino acid residues (for example, a non-N amino acid residue) are added between the N residue and the X residue; and (5) one or more amino acid residues (for example, a non-S and non-T amino acid residue) are added between the X residue and the (S or T) residue; and (6) any combination of (1) to (5).

Methods for deleting or replacing a certain amino acid residue in a polypeptide chain with another amino acid residue are well known to those skilled in the art. For example, any amino acid residue in a polypeptide chain can be modified (e.g., deleted or replaced) by standard techniques known in the art, such as site-directed mutagenesis and PCR-mediated mutagenesis.

In certain preferred embodiments, the amino acid residue for replacing an asparagine residue at N-linked glycosylation site (especially in a characteristic sequence N-X-(S or T)) may be one or more amino acid residues selected from the group consisting of: alanine, glycine, valine, leucine, isoleucine, phenylalanine, proline, tryptophan, serine, tyrosine, cysteine, methionine, glutamine, threonine, aspartic acid, glutamic acid, lysine, arginine and histidine. In certain preferred embodiments, the amino acid residue for replacing an asparagine residue at N-linked glycosylation site (especially in a characteristic sequence N-X-(S or T)) may be one or more amino acid residues selected from the group consisting of: alanine, glycine, valine, leucine, isoleucine, phenylalanine, proline, tryptophan, serine, tyrosine, cysteine, methionine, glutamine, threonine, aspartic acid, glutamic acid, lysine, arginine and histidine. In certain preferred embodiments, the amino acid residue for replacing an asparagine residue at N-linked glycosylation site (especially in a characteristic sequence N-X-(S or T)) may be alanine residue. In certain preferred embodiments, the asparagine residue at each N-linked glycosylation site (especially in a characteristic sequence N-X-(S or T)) is replaced with alanine. In certain preferred embodiments, the amino acid residue for replacing an asparagine residue at N-linked glycosylation site (especially in a characteristic sequence N-X-(S or T)) may be glutamine residue. In certain preferred embodiments, the asparagine residue at each N-linked glycosylation site (especially in a characteristic sequence N-X-(S or T)) is replaced with glutamine.

In certain preferred embodiments, the amino acid residue for replacing a (S or T) residue in a characteristic sequence N-X-(S or T) may be one or more amino acid residues selected from the group consisting of: alanine, glycine, valine, leucine, isoleucine, phenylalanine, proline, tryptophan, tyrosine, cysteine, methionine, glutamine, aspartic acid, glutamic acid, lysine, arginine and histidine. In certain preferred embodiments, the amino acid residue for replacing a (S or T) residue in a characteristic sequence N-X-(S or T) may be an amino acid residue selected from the group consisting of: alanine, glycine, valine, leucine, isoleucine, phenylalanine, proline, tryptophan, tyrosine, cysteine, methionine, glutamine, aspartic acid, glutamic acid, lysine, arginine and histidine.

In addition, with the development of protein crystallization and structure analysis technology, the research and understanding of the function and properties of HA protein have become more and more in-depth. Therefore, with the aid of a computer program or software (e.g., PyMol), the positions and conformations of the asparagine residue and (S or T) residue at each N-linked glycosylation site (especially in a characteristic sequence N-X-(S or T)) in the HA trimer can be determined. Based on this, combining the physicochemical properties of amino acid residues (for example, size, shape, charge, ability to form covalent or hydrogen bonds, etc.), suitable amino acid residues can be selected for replacing the asparagine residue and (S or T) residue. For example, it is known in the art that conservative substitutions can be made to a protein or polypeptide without significantly affecting or altering the function and properties of the protein or polypeptide.

Therefore, in certain preferred embodiments, the mutant differs from the wild-type hemagglutinin protein of influenza virus at least in that the asparagine residue at each N-linked glycosylation site (especially in a characteristic sequence N-X-(S or T)) in the wild-type hemagglutinin protein is each independently conservatively replaced. In certain preferred embodiments, the mutant differs from the wild-type hemagglutinin protein of influenza virus at least in that the asparagine residue at each N-linked glycosylation site (especially in a characteristic sequence N-X-(S or T)) in the wild-type hemagglutinin protein is each independently conservatively replaced with an amino acid residue selected from the group consisting of: alanine, glycine, glutamine, serine, threonine, tyrosine, cysteine, tryptophan.

In certain preferred embodiments, the mutant differs from the wild-type hemagglutinin protein of influenza virus at least in that the (S or T) residue in each characteristic sequence N-X-(S or T) in the wild-type hemagglutinin protein is each independently conservatively replaced by a non-S and non-T amino acid residue. In certain preferred embodiments, the mutant differs from the wild-type hemagglutinin protein of influenza virus at least in that the (S or T) residue in each characteristic sequence N-X-(S or T) in the wild-type hemagglutinin protein is each independently conservatively replaced with an amino acid residue selected from the group consisting of: alanine, glycine, asparagine, glutamine, tyrosine, cysteine, and tryptophan.

In certain preferred embodiments, the mutant differs from the wild-type hemagglutinin protein of influenza virus at least in that each characteristic sequence N-X-(S or T) of the wild-type hemagglutinin protein independently has a mutation selected from the group consisting of:

(1) the N residue is deleted or conservatively replaced;
(2) the (S or T) residue is deleted or conservatively replaced;
(3) the X residue is deleted or replaced with a proline residue;
(4) a non-N amino acid residue is added between the N residue and the X residue;
(5) a non-S and non-T amino acid residue is added between the X residue and the (S or T) residue; and
(6) any combination of (1) to (5).

In certain preferred embodiments, the mutant differs from the wild-type hemagglutinin protein of influenza virus at least in that the N residues in some characteristic sequences N-X-(S or T) in the wild-type hemagglutinin protein are each independently conservatively replaced; and the (S or T) residues in the remaining characteristic sequences N-X-(S or T) are each independently conservatively replaced with a non-S and non-T amino acid residue. In certain preferred embodiments, the mutant differs from the wild-type hemagglutinin protein of influenza virus at least in that the N residues in some characteristic sequences N-X-(S or T) in the wild-type hemagglutinin protein are each independently conservatively replaced with an amino acid residue selected from the group consisting of: alanine, glycine, glutamine, serine, threonine, tyrosine, cysteine, and tryptophan; and, the (S or T) residues in the remaining characteristic sequences N-X-(S or T) are each independently conservatively replaced with an amino acid residue selected from the group consisting of: alanine, glycine, asparagine, glutamine, tyrosine, cysteine, tryptophan.

It is easy to understand that a signal peptide of protein (usually located at the N-terminus of the protein) can guide/promote the secretion of the protein, and the signal peptide can be removed during or after the secretion without affecting the function of the protein. Therefore, in certain preferred embodiments, as compared with the wild-type hemagglutinin protein of H3N2 subtype influenza virus, the mutant does not contain an N-linked glycosylation site and does not contain a signal peptide (for example, a N-terminal signal peptide) of the wild-type hemagglutinin protein.

It is also easy to understand that a transmembrane region of protein generally directs/promotes the anchoring of the protein to a membrane (for example, a cell membrane or a viral envelope). In some cases, the deletion of a transmembrane region of protein will not adversely affect the biological activities (for example, immunogenicity and immunoprotective properties) of the protein. Therefore, in certain preferred embodiments, as compared with the wild-type hemagglutinin protein of H3N2 subtype influenza virus, the mutant does not contain an N-linked glycosylation site and does not contain a transmembrane region of the wild-type hemagglutinin protein.

Many known methods can be used to determine the position and sequence of the signal peptide and the position and sequence of the transmembrane region in influenza virus HA protein (see, for example, T M Tumpey et al., Proc. Natl. Acad. Sci. USA 99, 13849 (2002)). In addition, the signal peptides and transmembrane regions of various HA proteins have been reported (see, for example, James Stevens et al. Science 312, 404 (2006)). Therefore, the positions and sequences of signal peptides and transmembrane regions of various HA proteins can be easily determined and modified (for example, deleted).

In certain preferred embodiments, as compared with the wild-type hemagglutinin protein of H3N2 subtype influenza virus, the mutant does not contain an N-linked glycosylation site and does not contain a signal peptide (for example, a N-terminal signal peptide) and a transmembrane region of the wild-type hemagglutinin protein.

In certain preferred embodiments, the wild-type hemagglutinin protein is from an influenza A virus H3N2 subtype, such as an H3N2 subtype influenza virus that has been prevalent after 2005, such as A/WISCONSIN/67/2005 (H3N2) and A/HONG_KONG/4801/2014 (H3N2). In certain preferred embodiments, the wild-type hemagglutinin protein has a sequence selected from the group consisting of: SEQ ID NOs: 1 and 6.

In certain preferred embodiments, the amino acid sequence of the wild-type hemagglutinin protein is shown in SEQ ID NO: 1; and the mutant differs from SEQ ID NO: 1 at least in that the mutant does not contain a characteristic sequence N-X-(S or T); in which N represents asparagine, X represents any one amino acid other than proline, S represents serine, and T represents threonine. In certain preferred embodiments, the amino acid sequence of the wild-type hemagglutinin protein is shown in SEQ ID NO: 1; and the mutant differs from SEQ ID NO: 1 at least in that each characteristic sequence N-X-(S or T) in SEQ ID NO: 1 independently has a mutation selected from the group consisting of: (1) the N residue is deleted or replaced with one or more other amino acid residues (for example, a non-N Amino acid residue); (2) the (S or T) residue is deleted or replaced with one or more other amino acid residues (for example, a non-S and non-T amino acid residue); (3) the X residue is deleted or replaced with proline residue; (4) a non-N amino acid residue is added between the N residue and the X residue; (5) a non-S and non-T amino acid residue is added between the X residue and the (S or T) residue; and, (6) any combination of (1) to (5). In certain preferred embodiments, the mutant further differs from SEQ ID NO: 1 in that the mutant does not contain a signal peptide (for example, the amino acids 1-10 of SEQ ID NO: 1). In certain preferred embodiments, the mutant further differs from SEQ ID NO: 1 in that the mutant does not contain a transmembrane region (for example, the amino acids 504-550 of SEQ ID NO: 1). In certain preferred embodiments, the mutant further differs from SEQ ID NO: 1 in that the mutant does not contain a signal peptide (for example, the amino acids 1-10 of SEQ ID NO: 1) and a transmembrane region (for example, the amino acids 504-550 of SEQ ID NO: 1).

In certain preferred embodiments, the amino acid sequence of the wild-type hemagglutinin protein is shown in SEQ ID NO: 1; and the mutant differs from SEQ ID NO: 1 at least in that the amino acids 1-10 and 504-550 of SEQ ID NO: 1 are deleted, and the asparagine residues at sites 22, 38, 63, 126, 133, 144, 165, 246, 285 and 483 of SEQ ID NO: 1 are each independently deleted or replaced with one or more other amino acid residues (for example, a non-N amino acid residue, such as alanine residue or glutamine residue).

In certain preferred embodiments, the amino acid sequence of the wild-type hemagglutinin protein is shown in SEQ ID NO: 6; and the mutant differs from SEQ ID NO: 6 at least in that the mutant does not contain a characteristic sequence N-X-(S or T); wherein N represents asparagine, X represents any one amino acid other than proline, S represents serine, and T represents threonine. In certain preferred embodiments, the amino acid sequence of the wild-type hemagglutinin protein is shown in SEQ ID NO: 6; and the mutant differs from SEQ ID NO: 6 at least in that each characteristic sequence N-X-(S or T) in SEQ ID NO: 6 independently has a mutation selected from the group consisting of: (1) the N residue is deleted or replaced with one or more other amino acid residues (for example, a non-N amino acid residue); (2) the (S or T) residue is deleted or replaced with one or more other amino acid residues (for example, a non-S and non-T amino acid residue); (3) the X residue is deleted or replaced with proline residue; (4) a non-N amino acid residue is added between the N residue and the X residue; (5) a non-S and non-T amino acid residue is added between the X residue and the (S or T) residue; and, (6) any combination of (1) to (5). In certain preferred embodiments, the mutant further differs from SEQ ID NO: 6 in that the mutant does not contain a signal peptide (for example, amino acids 1-25 of SEQ ID NO: 6). In certain preferred embodiments, the mutant further differs from SEQ ID NO: 6 in that the mutant does not contain a transmembrane region (for example, amino acids 518-565 of SEQ ID NO: 6). In certain preferred embodiments, the mutant further differs from SEQ ID NO: 1 in that the mutant does not contain a signal peptide (for example, amino acids 1-25 of SEQ ID NO: 6) and a transmembrane region (for example, amino acids 518-565 of SEQ ID NO: 6).

In certain preferred embodiments, the amino acid sequence of the wild-type hemagglutinin protein is shown in SEQ ID NO: 6; and the mutant differs from SEQ ID NO: 6 at least in that the amino acids 1-25 and 518-565 of SEQ ID NO: 6 are deleted, and the asparagine residues at sites 37, 53, 60, 78, 137, 141, 148, 180, 261, 300 and 498 of SEQ ID NO: 6 are each independently deleted or replaced with one or more other amino acid residues (for example, a non-N amino acid residue, such as alanine residue or glutamine residue).

In certain preferred embodiments, the mutant has an amino acid sequence selected from the group consisting of: SEQ ID NOs: 12-13.

Those skilled in the art know that the amino acid sequence of a protein or polypeptide can be appropriately modified (for example, by addition, deletion, and/or substitution of amino acid residues) without significantly affecting the function and properties of the protein or polypeptide. Therefore, in some cases, by further modifying the amino acid sequence of the above mutant, additional mutants can be obtained that retain the ability of inducing protective antibodies against different subtypes of influenza viruses and have protection effect against different subtypes of influenza viruses.

Therefore, in certain preferred embodiments, the mutant of the present invention has an identity of at least 85%, at least 90%, at least 91%, at least 92%, at least 93%, at least 94%, at least 95%, at least 96%, at least 97%, at least 98%, at least 99% or 100% to an amino acid sequence selected from the group consisting of: SEQ ID NOs: 12-13; provided that the mutant does not contain any N-linked glycosylation site (for example, does not contain any characteristic sequence N-X-(S or T)).

In certain preferred embodiments, the mutant of the present invention has an addition, deletion or substitution of one or more amino acid residues as compared to an amino acid sequence selected from the group consisting of: SEQ ID NOs: 12-13; provided that the mutant does not contain any N-linked glycosylation site (for example, does not contain any characteristic sequence N-X-(S or T)). In certain preferred embodiments, the mutant of the present invention has an addition, deletion or substitution of one or several (for example, 1, 2, 3, 4, 5, 6, 7, 8, 9) amino acid residues as compared to an amino acid sequence selected from the group consisting of: SEQ ID NOs: 12-13; provided that the mutant does not contain any N-linked glycosylation sites (for example, does not contain any characteristic sequence N-X-(S or T)). In certain preferred embodiments, the mutant of the present invention has a substitution (especially conservative substitution) of one or several (for example, 1, 2, 3, 4, 5, 6, 7, 8, 9) amino acid residues as compared to an amino acid sequence selected from the group consisting of: SEQ ID NOs: 12-13; provided that the mutant does not contain any N-linked glycosylation site (for example, does not contain any characteristic sequence N-X-(S or T)).

The mutant derived from the HA protein of H3N2 subtype influenza virus as disclosed in the present application does not contain a glycosylation site (for example, does not contain a characteristic sequence N-X-(S or T)), and can induce broad-spectrum protective antibodies against influenza viruses in vivo, and can provide broad-spectrum protection against influenza viruses in vivo. In particular, the mutant disclosed herein is capable of inducing protective antibodies against influenza viruses of different subtypes (for example, H3N2, H7N9, and/or H1N1 subtypes) and achieving protection against influenza viruses of different subtypes (for example, H3N2, H7N9, and/or H1N1 subtypes), and therefore can be used as a broad-spectrum vaccine capable of combating a variety of subtypes (e.g., at least two, at least three or more subtypes; for example, H3N2, H7N9, and/or H1N1 subtypes) of influenza viruses for the prevention and/or treatment of an infection of a variety of subtypes (e.g., at least two, at least three or more subtypes; for example, H3N2, H7N9, and/or H1N1 subtypes) of influenza viruses and a disease (e.g., influenza) associated with the infection. Therefore, the mutant disclosed herein is particularly advantageous.

As to Recombinant Protein

In one aspect, the present application relates to a recombinant protein, comprising a mutant of hemagglutinin protein of H3N2 subtype influenza virus according to the present invention, and an additional peptide segment linked to the mutant.

In the recombinant protein of the present application, the additional peptide segment may be linked to the mutant in various ways. For example, in certain preferred embodiments, the additional peptide segment is directly linked to the mutant. In other words, the additional peptide segment is directly linked to the mutant via a peptide bond. In certain preferred embodiments, the additional peptide segment is linked to the mutant via a linker. A suitable linker in the prior art may consist of repeated GGGGS amino acid sequences or a variant thereof. For example, a linker having an amino acid sequence (GGGGS)$_4$ may be used, but a variant thereof may also be used (Holliger et al. (1993), Proc. Natl. Acad. Sci. USA 90: 6444-6448). In addition, other linkers can be used, such as linkers described by Alfthan et al. (1995), Protein Eng. 8: 725-731; Choi et al. (2001), Eur. J. Immunol. 31: 94-106; Hu et al. (1996), Cancer Res. 56: 3055-3061; Kipriyanov et al. (1999), J. Mol. Biol. 293: 41-56 and Roovers et al. (2001), Cancer Immunol.

In the recombinant protein of the present application, the additional peptide segment may be linked to either terminus of the mutant. For example, in certain preferred embodiments, the additional peptide segment is linked to the N-terminus of the mutant. In certain preferred embodiments, the additional peptide segment is linked to the C-terminus of the mutant.

The recombinant protein according to the present invention may comprise one or more additional peptide segments. For example, in certain preferred embodiments, the recombinant protein according to the present invention may comprise at least 1, at least 2, at least 3, at least 5 or more additional peptide segments. It is easy to understand that each of these peptide segments can be independently linked to either terminus (N-terminus or C-terminus) of the mutant in various ways. For example, in certain preferred embodiments, the recombinant protein of the present invention may comprise two additional peptide segments, wherein one additional peptide segment is linked to the N-terminus of the mutant with or without a linker, and, another additional peptide segment is linked to the C-terminus of the mutant with or without a linker. In certain preferred embodiments, the recombinant protein of the present invention may comprise two or more additional peptide segments, wherein the two or more additional peptide segments each independently is linked to the N-terminus or C-terminus of the mutant with or without a linker. In certain preferred embodiments, when two or more additional peptide segments are linked to the N-terminus of the mutant, the two or more additional peptide segments may be tandem in any order, and then linked to the N-terminus of the mutant with or without a linker. Similarly, in certain preferred embodiments, when two or more additional peptide segments are linked to the C-terminus of the mutant, the two or more additional peptide segments may be tandem in any order, and then linked to the C-terminus of the mutant with or without a linker.

Appropriate additional peptide segments can be selected according to actual needs. For example, in certain preferred embodiments, the additional peptide segment may be a signal peptide (e.g., a signal peptide as shown in SEQ ID NO: 9). Without being bound by any theory, it is generally believed that the use of a signal peptide can promote the secretion of recombinant protein and thus facilitate the recovery of the recombinant protein. Generally, such signal peptide can be linked to the N-terminus of the mutant. In addition, during or after the secretion, the signal peptide can be removed to produce the desired mutant or recombinant protein. In certain preferred embodiments, the additional peptide segment may be a tag peptide, for example, a 6*His tag as shown in SEQ ID NO: 11. Without being bound by any theory, it is generally believed that the use of a tag peptide can facilitate the detection, recovery and purification of recombinant protein. For example, nickel ions can be used to purify a 6*His-tagged protein. In certain preferred embodiments, the additional peptide segment may be a folding motif that promotes the trimer formation of the mutant. Such folding motif includes, but is not limited to, a folding motif as shown in SEQ ID NO: 10. In certain preferred embodiments, the additional peptide segment may be a detectable label, such as a fluorescent protein.

Thus, in certain preferred embodiments, the additional peptide segment is selected from a signal peptide, a tag peptide, a folding motif, a detectable label, and any combination thereof. In certain preferred embodiments, the signal peptide has an amino acid sequence as shown in SEQ ID NO: 9. In certain preferred embodiments, the signal peptide is linked to the N-terminus of the mutant. In certain preferred embodiments, the folding motif has an amino acid sequence as shown in SEQ ID NO: 10. In certain preferred embodiments, the folding motif is linked to the C-terminus of the mutant. In certain preferred embodiments, the tag peptide has an amino acid sequence as shown in SEQ ID NO: 11. In certain preferred embodiments, the tag peptide is linked to the N-terminus or C-terminus of the mutant.

In certain preferred embodiments, the recombinant protein may have an amino acid sequence selected from the group consisting of: SEQ ID NOs: 3 and 8.

Those skilled in the art know that the amino acid sequence of a protein or polypeptide can be appropriately modified (e.g., by addition, deletion, and/or substitution of amino acid residues) without significantly affecting the function and properties of the protein or polypeptide. Therefore, in some cases, by further modifying the amino acid sequence of the above-mentioned recombinant protein, an additional recombinant protein can be obtained, which retains the ability of inducing protective antibodies against different subtypes of influenza viruses and has protection effect against different subtypes of influenza viruses.

Therefore, in certain preferred embodiments, the recombinant protein of the present invention has an identity of at least 85%, at least 90%, at least 91%, at least 92%, at least 93%, at least 94%, at least 95%, at least 96%, at least 97%, at least 98%, at least 99% or 100% to an amino acid sequence selected from the group consisting of: SEQ ID NOs: 3 and 8; provided that the recombinant protein or mutant does not contain any N-linked glycosylation site (for example, does not contain any characteristic sequence N-X-(S or T)).

In certain preferred embodiments, the recombinant protein of the present invention has an addition, deletion or substitution of one or more amino acid residues as compared to an amino acid sequence selected from the group consisting of: SEQ ID NOs: 3 and 8; provided that the recombinant protein or the mutant does not contain any N-linked glycosylation site (for example, does not contain any characteristic sequence N-X-(S or T)). In certain preferred embodiments, the recombinant protein of the present invention has an addition, deletion or substitution of one or several (e.g., 1, 2, 3, 4, 5, 6, 7, 8, 9) amino acid residues as compared to an amino acid sequence selected from the group consisting of: SEQ ID NOs: 3 and 8; provided that the recombinant protein or the mutant does not contain any N-linked glycosylation site (for example, does not contain any characteristic sequence N-X-(S or T)). In certain preferred embodiments, the recombinant protein of the present invention has a substitution (especially a conservative substitution) of one or several (e.g., 1, 2, 3, 4, 5, 6, 7, 8, 9) amino acid residues as compared to an amino acid sequence selected from the group consisting of: SEQ ID NOs: 3 and 8; provided that the recombinant protein or the mutant does not contain any N-linked glycosylation site (for example, does not contain any characteristic sequence N-X-(S or T)).

As to Nucleic Acid Molecule, Vector, Virus and Host Cell

In another aspect, the present application relates to a nucleic acid molecule, comprising or consisting of a nucleotide sequence encoding a mutant of the present invention or a recombinant protein of the present invention. In certain preferred embodiments, the nucleic acid molecule of the present invention is isolated or purified.

In another aspect, the present application relates to a vector, comprising a nucleic acid molecule as described above. The vector of the present invention may be a cloning vector, a transfer vector, or an expression vector. In a preferred embodiment, the vector of the present invention is, for example, a plasmid, a cosmid, a phage, and the like. In a preferred embodiment, the vector is capable of expressing a mutant of the present invention or a recombinant protein of the present invention in a eukaryotic cell (e.g., an insect cell). In a preferred embodiment, the vector is a baculovirus transfer vector that can be used with baculovirus genomic DNA to achieve the expression of a mutant of the present invention or a recombinant protein of the present invention in an insect cell. In a preferred embodiment, the baculovirus is an *Autographa californica* multicapsid nucleopolyhedrovirus (AcMNPV).

In another aspect, the present invention also relates to a host cell, comprising a nucleic acid molecule or a vector as described above. Such host cell includes, but is not limited to, a prokaryotic cell such as *E. coli* cell, and an eukaryotic cell such as yeast cell, an insect cell, a plant cell, and an animal cell (e.g., a mammalian cell, such as a mouse cell, a human cell, etc.). The host cell of the present invention may also be a cell line, such as a 293T cell. Without being bound by any theory, it is generally believed that the use of a eukaryotic cell helps maintain the correct conformation of the protein and promotes protein folding. Thus, in certain preferred embodiments, the host cell of the present invention is a eukaryotic cell such as an insect cell. In certain preferred embodiments, the host cell of the present invention is an insect cell, which comprises a baculovirus transfer vector containing the aforementioned nucleic acid molecule, and a baculovirus genomic DNA. In a preferred embodiment, the baculovirus is an *Autographa californica* multicapsid nucleopolyhedrovirus (AcMNPV).

In another aspect, the present invention also relates to a virus (for example, a baculovirus), comprising a nucleic acid molecule or vector as described above. In certain preferred embodiments, the virus is a baculovirus, such as an *Autographa californica* multicapsid nucleopolyhedrovirus (AcMNPV).

As to Multimer

In one aspect, the present application relates to a multimer, comprising or consisting of a plurality of mutants of the present invention or a plurality of recombinant proteins of the present invention. In certain preferred embodiments, the multimer is a trimer. In other words, the multimer comprises or consists of three mutants or recombinant proteins of the present invention. In certain preferred embodiments, the trimer has the same or similar conformation as a trimer formed from the natural HA protein.

As to Composition

In another aspect, the present application also relates to a composition, comprising the aforementioned mutant, or the aforementioned recombinant protein, or the aforementioned nucleic acid molecule, or the aforementioned vector, or the aforementioned host cell, or the aforementioned virus, or the aforementioned multimer. In certain preferred embodiments, the composition comprises a mutant or recombinant protein of the present invention. In certain preferred embodiments, the composition comprises a multimer of the present invention.

As to Pharmaceutical Composition, Treatment Method and Use

In another aspect, the present invention also relates to a pharmaceutical composition (for example, a vaccine), comprising a mutant or recombinant protein or multimer of the present invention, optionally further comprising a pharmaceutically acceptable carrier and/or excipient. The pharmaceutical composition (for example, a vaccine) of the present invention can be used to prevent or treat an infection of influenza virus or a disease caused by an infection of influenza virus, such as influenza and the like.

In certain preferred embodiments, the mutant or recombinant protein or multimer of the present invention is present in an effective amount to prevent or treat an infection of influenza virus or a disease caused by an infection of influenza virus. In certain preferred embodiments, the pharmaceutical composition (for example, a vaccine) of the present invention further comprises an additional active ingredient. Preferably, the additional active ingredient is capable of preventing or treating an infection of influenza virus or a disease caused by an infection of influenza virus. In certain preferred embodiments, the pharmaceutical composition (for example, a vaccine) of the present invention further comprises an adjuvant, such as an aluminum adjuvant.

In certain preferred embodiments, the pharmaceutical composition further comprises a pharmaceutically acceptable carrier, excipient, stabilizer or other reagent capable of providing advantageous properties for administration of the pharmaceutical composition (for example, administration to a human subject). A suitable pharmaceutical carrier includes, for example, sterile water, saline, glucose, condensation product of castor oil and ethylene oxide, liquid acid, lower alcohol (e.g., $C_{1-4}$ alcohol), oil (e.g., corn oil, peanut oil, sesame oil; which optionally further comprises an emulsifier such as mono- or di-glyceride of fatty acid or phospholipid such as lecithin), ethylene glycol, polyalkylene glycol, sodium alginate, poly(vinylpyrrolidone), and the like. The carrier optionally further comprises an adjuvant, a preservative, a stabilizer, a wetting agent, an emulsifier, a penetration enhancer, and the like. In certain preferred embodiments, the pharmaceutical composition is sterilized. In addition, the viscosity of the pharmaceutical composition can be controlled and maintained by selecting a suitable solvent or excipient. In certain preferred embodiments, the pharmaceutical composition is formulated to have a pH of 4.5-9.0, 5.0-8.0, 6.5-7.5, or 6.5-7.0.

The pharmaceutical composition (for example, a vaccine) of the present invention can be administered by a method known in the art, such as, but not limited to, oral administration or injection. In certain preferred embodiments, the pharmaceutical composition (for example, a vaccine) of the present invention is administered in unit dosage form.

The amount of the pharmaceutical composition (for example, a vaccine) of the present invention required to prevent or treat a particular condition depends on the route of administration, the severity of condition to be treated, the patient's gender, age, weight, and general health, etc., and can be reasonably determined by a physician according to the actual situation.

In certain preferred embodiments, the pharmaceutical composition (for example, a vaccine) of the present invention comprises a mutant derived from the HA protein of H3N2 subtype influenza virus or a recombinant protein or multimer comprising the mutant, which is capable of inducing protective antibodies against H3N2, H7N9 and/or H1N1 subtype influenza viruses and achieving protection against H3N2, H7N9 and/or H1N1 subtype influenza viruses, and therefore, can be used to prevent and/or treat an infection of H3N2, H7N9 and/or H1N1 subtype influenza viruses and a disease (for example, an influenza) associated therewith.

In another aspect, the present invention relates to a method for preventing or treating an influenza virus infection or a disease caused by an influenza virus infection in a subject, which comprises administrating a prophylactically or therapeutically effective amount of a mutant or recombinant protein or multimer according to the present invention or a pharmaceutical composition of the present invention to the subject. In certain preferred embodiments, the disease caused by an influenza virus infection is an influenza. In certain preferred embodiments, the subject is a mammal, such as a mouse and a human.

In certain preferred embodiments, the method of the present invention can be used for prevention and/or treatment of an infection of H3N2, H7N9 and/or H1N1 subtype influenza virus and a disease (for example, an influenza) associated therewith.

In another aspect, the present invention also relates to a use of the mutant or recombinant protein or multimer of the present invention in manufacture of a pharmaceutical composition (for example, a vaccine), wherein the pharmaceutical composition (for example, a vaccine) is used for prevention or treatment of an influenza virus infection or a disease caused by an influenza virus infection in a subject. In certain preferred embodiments, the disease caused by an influenza virus infection is an influenza. In certain preferred embodiments, the subject is a mammal, such as a mouse and a human.

In certain preferred embodiments, the pharmaceutical composition (for example, a vaccine) comprises a mutant derived from the HA protein of H3N2 subtype influenza virus or a recombinant protein or multimer comprising the mutant, and is used for prevention and/or treatment of an infection of H3N2, H7N9 and/or H1N1 subtype influenza viruses and a disease (for example, an influenza) associated therewith.

In another aspect, the present invention also relates to a mutant or recombinant protein or multimer as described above, for use in prevention or treatment of an influenza virus infection or a disease caused by an influenza virus infection in a subject. In certain preferred embodiments, the disease caused by an influenza virus infection is an influenza. In certain preferred embodiments, the subject is a mammal, such as a mouse and a human. In certain preferred embodiments, the mutant or recombinant protein or multimer is used for prevention and/or treatment of an infection of H3N2, H7N9 and/or H1N1 subtype influenza viruses and a disease (for example, influenza) associated therewith.

As to the Preparation Method

In another aspect, the present invention relates to a method for preparing the above-mentioned mutant or recombinant protein, which comprises culturing a host cell or virus of the present invention under a condition allowing the expression of the mutant or recombinant protein; and, recovering the expressed mutant or recombinant protein.

In certain preferred embodiments, the method comprises: introducing a vector (for example, an expression vector) of the present invention into a host cell (for example, an eukaryotic cell) to express the mutant or recombinant protein in the host cell; and, recovering the expressed mutant or recombinant protein. In certain preferred embodiments, the method comprises: introducing a baculovirus transfer vector containing the aforementioned nucleic acid molecule and a baculovirus genomic DNA into an insect cell, thereby expressing the mutant or recombinant protein in the insect cell; and recovering the expressed mutant or recombinant protein. In a preferred embodiment, the baculovirus is *Autographa californica* multicapsid nucleopolyhedrovirus (AcMNPV).

In another aspect, the present invention also relates to a method of preparing a vaccine, comprising mixing a mutant or recombinant protein or multimer of the present invention with a pharmaceutically acceptable carrier and/or excipient, and optionally further mixing with an adjuvant such as aluminum adjuvant, and/or an additional active ingredient such as an additional active ingredient capable of preventing or treating an influenza virus infection or a disease caused by an influenza virus infection. In certain preferred embodiments, the method for preparing a vaccine comprises the following step: mixing a mutant or recombinant protein or multimer of the present invention with an adjuvant, such as an aluminum adjuvant.

As discussed above, the obtained vaccine can be used for the prevention or treatment of an influenza virus infection or a disease (for example, an influenza) caused by an influenza virus infection.

Illustration and Explanation of Relevant Terms in the Present Application

In the present application, unless otherwise stated, scientific and technical terms used herein have the meanings commonly understood by those skilled in the art. In addition, the laboratory operation steps of cell culture, molecular genetics, nucleic acid chemistry and immunology used herein are all routine procedures widely used in the corresponding fields. Meanwhile, in order to better understand the present invention, definitions and explanations of relevant terms are provided below.

As used herein, the term "identity" refers to a sequence match between two polypeptides or between two nucleic acids. When a certain position in two compared sequences is occupied by the same base or amino acid monomer subunit (for example, a position in each of the two DNA molecules is occupied by adenine, or a position in each of the two polypeptides is occupied by lysine), then the molecules are identical at that position. The "percent identity" between two sequences is a function of the number of matching positions shared by the two sequences divided by the number of compared positions×100. For example, if there are 6 matches in 10 positions of two sequences, the two sequences are 60% identical. For example, the DNA sequences CTGACT and CAGGTT have an identity of 50% (3 of the 6 positions match). In general, the comparison is made when two sequences are aligned to produce maximum identity. Such alignment can be achieved by using, for example, the method of Needleman et al. (1970) J. Mol. Biol. 48: 443-453, which can be conveniently performed by a computer program such as the Align program (DNAstar, Inc.). The algorithm of E. Meyers and W. Miller (Comput. Appl Biosci., 4: 11-17 (1988)) integrated into the ALIGN program (version 2.0) can also be used, in which a PAM120 weight residue table, a gap length penalty of 12, and a gap penalty of 4 are used to determine the percent identity between two amino acid sequences. Additionally, the Needleman and Wunsch (J Mol Biol. 48: 444-453 (1970)) algorithm integrated into the GAP program of the GCG software package (available at www.gcg.com) can be used, in which Blossom 62 matrix or PAM250 matrix, gap weights of 16, 14, 12, 10, 8, 6, or 4 and length weights of 1, 2, 3, 4, 5, or 6 are used to determine the percent identity between two amino acid sequences.

As used herein, the term "conservative substitution" or "conservative replacement" refers to an amino acid substitution or replacement that does not adversely affect or alter the biological activity of a protein/polypeptide comprising an amino acid sequence. For example, a conservative substitution can be introduced by a standard technique known in the art, such as site-directed mutagenesis and PCR-mediated mutagenesis. Conservative amino acid substitution includes a substitution of amino acid residue with an amino acid residue having similar side chain, such as a substitution with a residue that is physically or functionally similar to the corresponding amino acid residue (for example, having similar size, shape, charge, chemical properties, including the ability of forming a covalent or hydrogen bond, etc.). A family of amino acid residues with similar side chains has been defined in the art. These families include amino acids with basic side chains (e.g., lysine, arginine, and histidine), acidic side chains (e.g., aspartic acid, glutamic acid), uncharged polar side chains (e.g., glycine, asparagine, glutamine, serine, threonine, tyrosine, cysteine, tryptophan), non-polar side chains (e.g., alanine, valine, leucine, isoleucine, proline, phenylalanine, methionine), β branched side chains (e.g., threonine, valine, isoleucine), and aromatic side chains (e.g., tyrosine, phenylalanine, tryptophan, histidine). Therefore, it is preferred to replace the corresponding amino acid residue with another amino acid residue from the same side chain family. Methods for identifying conservative substitution of amino acids are well known in the art (see, e.g., Brummell et al., Biochem. 32: 1180-1187 (1993); Kobayashi et al. Protein Eng. 12 (10): 879-884 (1999); and Burks et al. Proc. Natl Acad. Set USA 94: 412-417 (1997), which are incorporated herein by reference).

As used herein, the term "vector" refers to a nucleic acid vehicle into which a polynucleotide can be inserted. When a vector enables the expression of a protein encoded by an inserted polynucleotide, the vector is referred to as an expression vector. A vector can be introduced into a host cell by transformation, transduction, or transfection, so that the genetic material elements carried by the vector can be expressed in the host cell. Vectors are well known to those skilled in the art and include but are not limited to: plasmids; phagemids; cosmids; artificial chromosomes, such as yeast artificial chromosomes (YAC), bacterial artificial chromosomes (BAC) or P1-derived artificial chromosomes (PAC); phages such as λ phages or M13 phages and animal viruses. Animal viruses that can be used as vectors include, but are not limited to, retroviruses (including lentiviruses), adenoviruses, adeno-associated viruses, herpes viruses (such as herpes simplex virus), poxviruses, baculoviruses, papillomaviruses, and papovaviruses (such as SV40). A vector can contain a variety of elements that control expression, including, but not limited to, promoter sequence, transcription initiation sequence, enhancer sequence, selection element, and reporter gene. In addition, the vector may contain a replication initiation site.

As used herein, the term "host cell" refers to a cell that can be used to introduce a vector, which includes, but is not limited to, prokaryotic cell such as E. coli or Bacillus subtilis, fungal cell such as yeast cell or Aspergillus, insect cell such as S2 Drosophila cell or Sf9, or animal cell such as fibroblast cell, CHO cell, COS cell, NSO cell, HeLa cell, BHK cell, HEK 293 cell, or human cell.

As used herein, the expression "corresponding sequence fragment" or "corresponding fragment" refers to, when sequences are optimally aligned, that is, when the sequences are aligned to obtain the highest percent identity, a segment at an equivalent position in the sequences being compared. According to the present invention, the expression "corresponding amino acid position" refers to, when sequences are optimally aligned, that is, when the sequences are aligned to obtain the highest percentage identity, the amino acid sites/residues at an equivalent position in the compared sequences.

As used herein, the term "epitope" refers to a part on an antigen that is specifically bound by an immunoglobulin or antibody. "Epitope" is also known in the art as "antigenic determinant". An epitope or antigenic determinant usually consists of a chemically active surface group such as an amino acid or a carbohydrate or a sugar side chain of a molecule and usually has specific three-dimensional structural characteristics and specific charge characteristics. For example, an epitope typically includes at least 3, 4, 5, 6, 7, 8, 9, 10, 11, 12, 13, 14, or 15 consecutive or non-contiguous amino acids in a unique spatial conformation, which can be "linear" or "conformational". See, for example, Epitope Mapping Protocols in Methods in Molecular Biology, Vol. 66, G. E. Morris, Ed. (1996). In a linear epitope, all points of interaction between a protein and an interacting molecule (such as an antibody) exist linearly along the primary amino acid sequence of the protein. In a conformational epitope, the points of interaction exist across protein amino acid residues that are separated from each other.

As used herein, the term "multimer" refers to a polymer formed with of a polypeptide molecule (for example, a mutant or recombinant protein of the present invention) as monomer, which may generally comprise at least 2 (for example, 3, 4, 5 or more) polypeptide monomers (for example, mutants or recombinant proteins of the present invention). In such multimer, monomer molecules are polymerized to form multimer through an intermolecular interaction (such as hydrogen bonding, van der Waals force, and hydrophobic interaction). In certain embodiments of the present invention, the multimer is a trimer comprising 3 monomers.

As used herein, the term "isolated" or "being isolated" refer to being obtained from a source of natural state via artificial means. If a certain "isolated" substance or component appears in nature, the substance is isolated due to the change of the natural environment in which it exists, or the separation from the natural environment, or both. For example, if a non-isolated polynucleotide or polypeptide naturally exists in a living animal, the same polynucleotide or polypeptide with high-purity isolated from such natural state is referred to as isolated. The term "isolated" or "being isolated" does not exclude the mixing with an artificial or synthetic substance, nor exclude the presence of other impurities which do not affect the activity of the substance.

As used herein, "characteristic sequence N-X-(S or T)" refers to a characteristic motif capable of occurring N-linked glycosylation, where N represents asparagine, X represents any one amino acid other than proline, S represents serine, and T represents threonine.

As used herein, the term "protective antibody" refers to an antibody that has a protective effect against a virus. Protective antibody includes, but is not limited to, an antibody capable of neutralizing virus virulence, an antibody capable of inhibiting a virus from recognizing and binding to a host cell, and an antibody capable of inhibiting fusion of a virus and a host cell.

As used herein, the term "pharmaceutically acceptable carrier and/or excipient" refers to a carrier and/or excipient that is pharmacologically and/or physiologically compatible with a subject and an active ingredient, which are well known in the art (see, for example, Remington's Pharmaceutical Sciences. Edited by Gennaro A R, 19th ed. Pennsylvania: Mack Publishing Company, 1995), and include, but are not limited to: pH adjuster, surfactant, adjuvant, ionic strength enhancer. For example, the pH adjusting agent includes, but is not limited to, phosphate buffer; the surfactant includes, but is not limited to, cationic, anionic, or non-ionic surfactant, such as Tween-80; the adjuvant includes, but is not limited to, aluminum adjuvant (such as hydroxide aluminum), Freund's adjuvant (e.g., complete Freund's adjuvant); ionic strength enhancer includes, but is not limited to, sodium chloride.

As used herein, the term "adjuvant" refers to a non-specific immune enhancer that, when delivered into the body with or in advance of an antigen, can enhance the body's immune response to the antigen or change the type of immune response. There are many types of adjuvants, including but not limited to aluminum adjuvants (e.g., aluminum hydroxide), Freund's adjuvants (e.g., complete Freund's adjuvant and incomplete Freund's adjuvant), *Corynebacterium* parvum, lipopolysaccharide, cytokines, etc. Freund's adjuvant is the most commonly used adjuvant in animal experiments. Aluminum hydroxide adjuvant is used more in clinical trials. In the present invention, it is particularly preferred that the adjuvant is an aluminum adjuvant.

As used herein, the term "effective amount" refers to an amount effective to achieve the intended purpose. For example, an effective amount for preventing or treating a disease (such as an influenza virus infection) means that it is effective in preventing, stopping or delaying the occurrence of a disease (such as an influenza virus infection), or relieving, reducing or treating a severity of an existing disease (such as a disease caused by infection of influenza virus). Determining such an effective amount is well within the capabilities of those skilled in the art. For example, an effective amount for therapeutic use will depend on the severity of the disease to be treated, the overall state of the patient's own immune system, the general condition of the patient such as age, weight and gender, the administration mode of drug, and other treatments applied concurrently, etc.

As used herein, the term "immunogenicity" refers to an ability to stimulate the body to generate a specific antibody or sensitized lymphocyte. It refers to not only the antigen's characteristics of stimulating a specific immune cell to activate, proliferate and differentiate the immune cell, and ultimately produce an immune effector such as an antibody and sensitized lymphocyte, but also a specific immune response that after the antigen stimulates the body, the body's immune system generates an antibody or sensitized T lymphocyte. Immunogenicity is the most important property of an antigen. Whether an antigen can successfully induce a host to produce an immune response depends on three factors: the nature of the antigen, the reactivity of the host, and the mode of immunization.

As used herein, the terms "polypeptide" and "protein" have the same meaning and are used interchangeably. And in the present invention, amino acids are generally represented by single-letter and three-letter abbreviations known in the art. For example, alanine can be represented by A or Ala.

As used herein, "subject" refers to an animal, such as a vertebrate. Preferably, the subject is a mammal, such as a human, bovine, equine, feline, canine, rodent or primate. Particularly preferably, the subject is a human. This term is used interchangeably with "patient" herein.

Beneficial Effects of the Present Invention

The present application provides a mutant of hemagglutinin protein of H3N2 subtype influenza virus, which is capable of inducing protective antibodies against influenza viruses of different subtypes (for example, H3N2, H7N9, and/or H1N1 subtypes), achieving protection against influenza viruses of different subtypes, and thus can be used as a broad-spectrum vaccine against multiple subtypes (e.g. at least 2, at least 3 or more subtypes) of influenza viruses for prevention and/or treatment of an infection of multiple subtypes (e.g. at least 2, at least 3 or more subtypes) of influenza viruses and a disease (e.g. influenza) associated with the infection.

In particular, the mutant derived from the HA protein of H3N2 subtype influenza virus disclosed in this application not only can induce protective antibodies against multiple strains of H3N2 subtype influenza virus (especially multiple strains of H3N2 subtype influenza virus prevalent in different ages) to achieve protection against multiple strains of H3N2 subtype influenza virus, but also can induce protective antibodies against H7N9 and/or H1N1 subtype influenza viruses to achieve protection against H7N9 and/or H1N1 subtype influenza viruses.

Therefore, the present application provides a broad-spectrum influenza vaccine, which can provide cross-protection against influenza viruses of multiple subtypes (for example, H3N2, H7N9, and/or H1N1 subtypes), and its immune effect is ideal, and it does not easily fail quickly due to the variation of influenza virus, so that the shortcomings of the existing influenza vaccines, such as the loss of immune efficacy and unsatisfactory immune effects caused by frequent variation of influenza viruses, are overcome. In particular, the broad-spectrum influenza vaccine of the present application solves the disadvantages that the existing influenza vaccines need to be changed every year and injected every year. In addition, the broad-spectrum influenza vaccine of the present application can effectively prevent the spread of multiple subtypes of influenza viruses and reduce economic losses and social panic caused by the influenza viruses. Therefore, the broad-spectrum influenza vaccine of the present application has a particularly significant advantage over the existing influenza vaccines.

The embodiments of the present invention will be described in detail below with reference to the drawings and examples, but those skilled in the art will understand that the following drawings and examples are only used to illustrate the present invention, rather than to limit the scope of the present invention. Various objects and advantageous aspects of the present invention will become apparent to those skilled in the art from the accompanying drawings and the following detailed description of the preferred embodiments.

BRIEF DESCRIPTION OF THE DRAWINGS

FIG. 1 schematically illustrates the sequence mutations and N-linked glycosylation of natural HA protein (W12005-WT-HA), HA-mut1 protein, HA-mut2 protein and HA-mut3 protein used in Example 1.

FIG. 2 schematically illustrates the schematic structure diagrams of the trimers formed with natural HA protein (FIG. 2A), HA-mut1 protein (FIG. 2B), HA-mut2 protein (FIG. 2C), and HA-mut3 protein (FIG. 2D) used in Example 1, respectively; in which FIG. 2A shows that the trimer formed by natural HA protein contains N-linked glycosyl chains in both the head and stem regions; FIG. 2B shows that the trimer formed by HA-mut1 protein does not contain N-linked glycosyl chain in both the head and stem regions; FIG. 2C shows that the trimer formed by HA-mut2 protein does not contain N-linked glycosyl chain in the head region, but still contains N-linked glycosyl chain in the stem region; FIG. 2D shows that the trimer formed by HA-mut3 protein does not contain N-linked glycosyl chain in the stem region, but still contains N-linked glycosyl chain in the head region.

FIG. 3 shows the results of SDS-PAGE analysis of six proteins prepared in Example 1, in which FIG. 3A shows the results of SDS-PAGE analysis of natural HA protein, HA-mut3, HA-mut2 and HA-mut1 proteins; FIG. 3B shows the results of SDS-PAGE analysis of natural HA protein, HAmg protein and HAug protein.

FIG. 6 shows the changes in body weight and survival of mice immunized with natural HA protein, HA-mut1 protein, HA-mut2 protein, HA-mut3 protein or PBS (negative control) after infection with the H3N2 subtype influenza viruses A/Beijing/32/1992 (H3N2) (FIGS. 6A-6B) and A/Aichi/2/1968 (H3N2) (FIGS. 6C-6D) which are prevalent at early ages, in which FIG. 6A and FIG. 6C show the changes in body weight of each group of experimental mice, and FIGS. 6B and 6D show the survival rate of each group of experimental mice.

FIG. 7 shows the changes in body weight and survival of mice immunized with natural HA protein, HA-mut1 protein, HAmg protein, HAug protein or PBS (negative control) after infection with H3N2 subtype influenza viruses A/Beijing/32/1992 (H3N2) (FIGS. 7A-7B) and A/Aichi/2/1968 (H3N2) (FIGS. 7C-7D) which are prevalent at early ages, in which FIG. 7A and FIG. 7C show the changes in body weight of each group of experimental mice, and FIG. 7B and FIG. 7D show the survival rate of each group of experimental mice.

FIG. 8 shows the changes in body weight and survival of mice immunized with natural HA protein, HA-mut1 protein, HA-mut2 protein, HA-mut3 protein or PBS (negative control) after infection with non-H3N2 subtype influenza viruses A/Shanghai/02/2013 (H7N9) (FIGS. 8A-8B) and A/California/04/2009 (H1N1) (FIGS. 8C-8D), in which FIG. 8A and FIG. 8C show the changes in body weight of each group of experimental mice, and FIG. 8B and FIG. 8D show the survival rate of each group of experimental mice.

FIG. 9 shows the changes in body weight and survival of mice immunized with natural HA protein, HA-mut1 protein, HAmg protein, HAug protein or PBS (negative control) after infection with non-H3N2 subtype influenza viruses A/Shanghai/02/2013 (H7N9) (FIGS. 9A-9B) and A/California/04/2009 (H1N1) (FIGS. 9C-9D), in which FIG. 9A and FIG. 9C show the changes in body weight of each group of experimental mice, and FIG. 9B and FIG. 9D shows the survival rate of each group of experimental mice.

FIG. 10 shows the results of SDS-PAGE analysis (left panel) and Western blot analysis (right panel) of HK2014-WT-HA protein; in which lane M: molecular weight marker; lane 1: sample without being purified by Ni-NTA nickel ion chromatography column; lane 2: fraction flowing through Ni-NTA nickel ion chromatography column; lane 3: fraction being eluted with 50 mM imidazole; lane 4: fraction being eluted with 50 mM imidazole; lane 5: fraction being eluted with 250 mM imidazole; the arrow indicates the position of the protein HK2014-WT-HA of interest.

SEQUENCE INFORMATION

Figure 2:
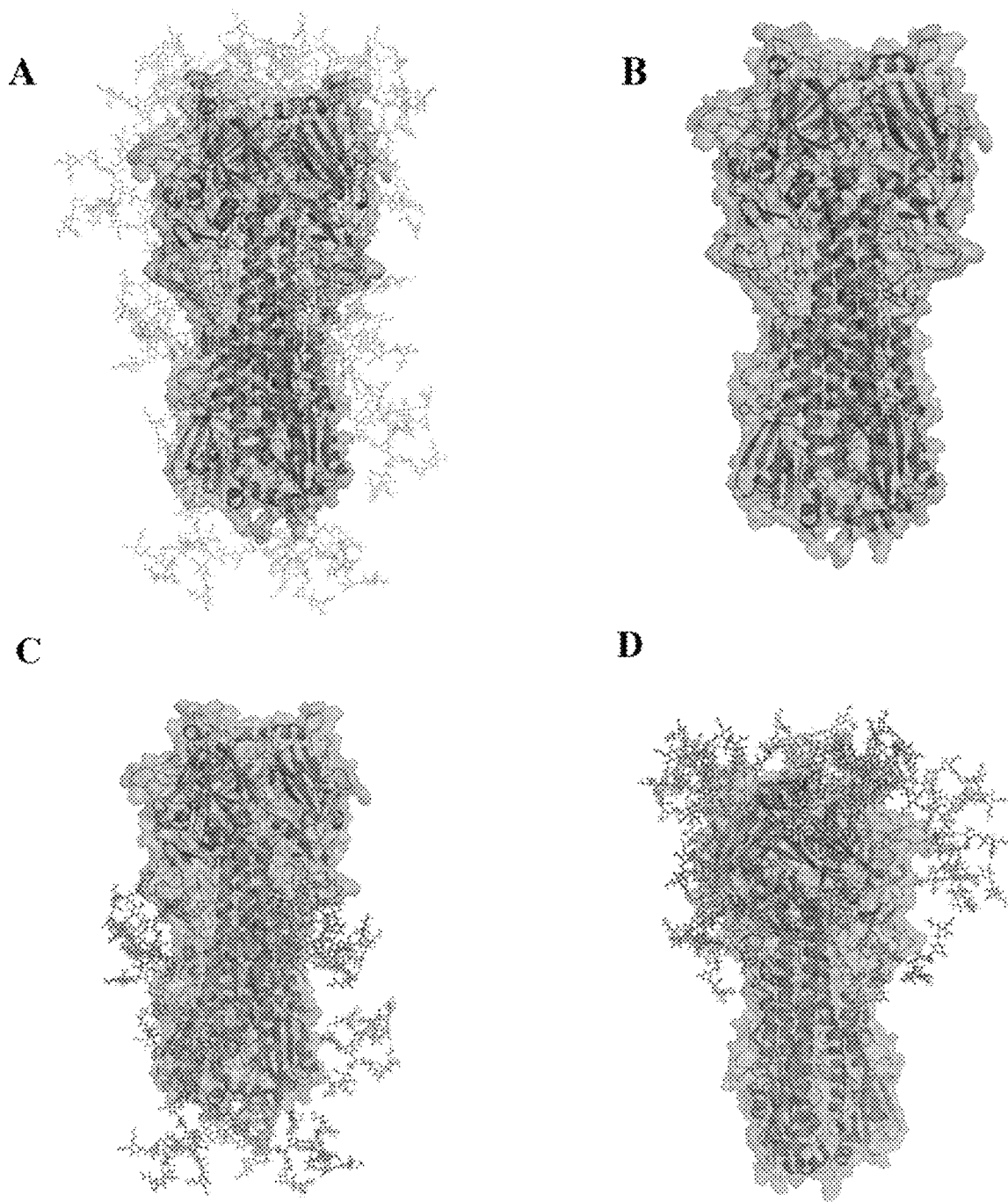
Figure 3:
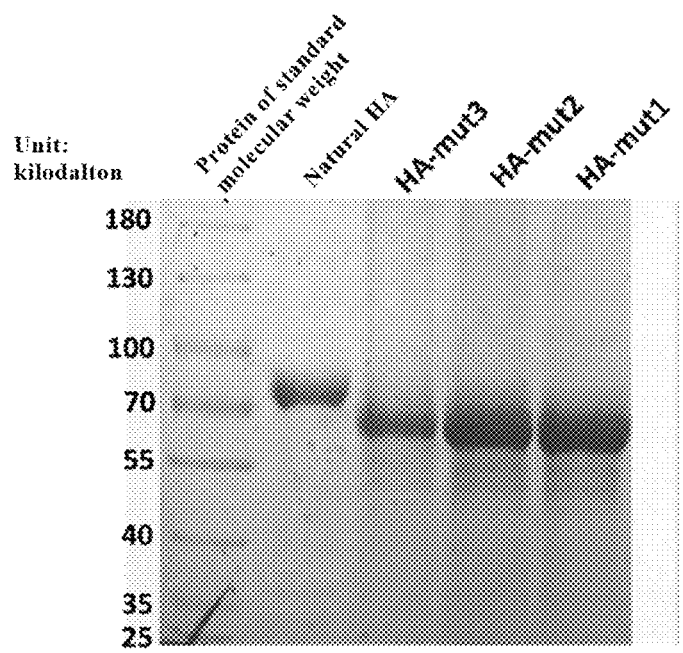
Figure 3:
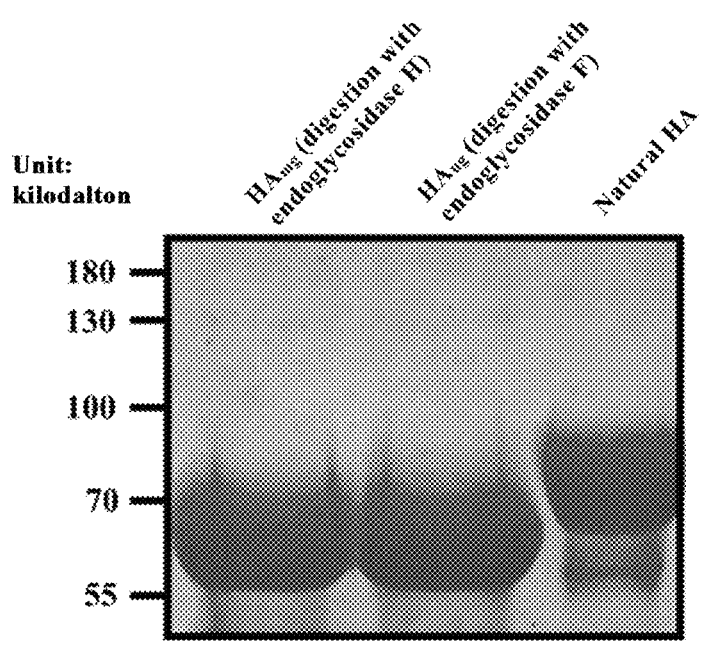

Information of the sequences involved in the invention is provided in Table 1 below.

TABLE 1

Sequence information

| SEQ ID NO: | Description of sequence |
|---|---|
| 1 | Full-length amino acid sequence of HA protein of influenza strain A/WISCONSIN/67/2005 (H3N2)<br><br>QKLPGNDNST ATLC LGHHAVPNGT IVKTITNDQI EVTNATELVQ SSSTGGICDS PHQILDGENC TLIDALLGDP QCDGFQNKKW DLFVERSKAY SNCYPYDVPD YASLRSLVAS SGTLEFNDES FNWTGVTQNG TSSSCKRRSN NSFFSRLNWL TQLKFKYPAL NVTMPNNEKF DKLYIWGVHH PVTDNDQIFL YAQASGRITV STKRSQQTVI PNIGSRPRIR NIPSRISIYW TIVKPGDILL INSTGNLIAP RGYFKIRSGK SSIMRSDAPI GKDNSECITP NGSIPNDKPF QNVNRITYGA CPRYVKQNTL KLATGMRNVP EKQTRGIFGA IAGFIENGWE GMVDGWYGFR HQNSEGIGQA ADLKSTQAAI NQINGKLNRL IGKTNEKFHQ IEKEFSEVEG RIQDLEKYVE DTKIDLWSYN AELLVALENQ HTIDLTDSEM NKLFERTKKQ LRENAEDMGN GCFKIYHKCD NACIGSIRNG TYDHDVYRDE ALNNRFQIKG VELKSGYKDW ILWISFAISC FLLCVALLGF IMWACQKGNI RCNICI |
| 2 | Amino acid sequence of WI2005-WT-HA protein<br><br>MATLC LGHHAVPNGT IVKTITNDQI EVTNATELVQ SSSTGGICDS PHQILDGENC TLIDALLGDP QCDGFQNKKW DLFVERSKAY SNCYPYDVPD YASLRSLVAS SGTLEFNDES FNWTGVTQNG TSSSCKRRSN NSFFSRLNWL TQLKFKYPAL NVTMPNNEKF DKLYIWGVHH PVTDNDQIFL YAQASGRITV STKRSQQTVI PNIGSRPRIR NIPSRISIYW TIVKPGDILL INSTGNLIAP RGYFKIRSGK SSIMRSDAPI GKDNSECITP NGSIPNDKPF QNVNRITYGA CPRYVKQNTL KLATGMRNVP EKQTRGIFGA IAGFIENGWE GMVDGWYGFR HQNSEGIGQA ADLKSTQAAI NQINGKLNRL IGKTNEKFHQ IEKEFSEVEG RIQDLEKYVE DTKIDLWSYN AELLVALENQ HTIDLTDSEM NKLFERTKKQ LRENAEDMGN GCFKIYHKCD NACIGSIRNG TYDHDVYRFE ALNNRFQIK SGRLVPRGSPGSGYIPEAPRDGQAYVRKDGEWVLLSTFLG HHHHHH |
| 3 | Amino acid sequence of HA-mut1 protein<br><br>MATLC LGHHAVPAGT IVKTITNDQI EVTAATELVQ SSSTGGICDS PHQILDGEAC TLIDALLGDP QCDGFQNKKW DLFVERSKAY SNCYPYDVPD YASLRSLVAS SGTLEFNDES FAWTGVTQAG TSSSCKRRSA NSFFSRLNWL TQLKFKYPAL AVTMPNNEKF DKLYIWGVHH PVTDNDQIFL YAQASGRITV STKRSQQTVI PNIGSRPRIR NIPSRISIYW TIVKPGDILL IASTGNLIAP RGYFKIRSGK SSIMRSDAPI GKDNSECITP AGSIPNDKPF QNVNRITYGA CPRYVKQNTL KLATGMRNVP EKQTRGIFGA IAGFIENGWE GMVDGWYGFR HQNSEGIGQA ADLKSTQAAI NQINGKLNRL IGKTNEKFHQ IEKEFSEVEG RIQDLEKYVE DTKIDLWSYN AELLVALENQ HTIDLTDSEM NKLFERTKKQ LRENAEDMGN GCFKIYHKCD NACIGSIRAG TYDHDVYRDE ALNNRFQIK SGRLVPRGSPGSGYIPEAPRDGQAYVRKDGEWVLLSTFLG HHHHHH |
| 4 | Amino acid sequence of HA-mut2 protein<br><br>MATLC LGHHAVPNGT IVKTITNDQI EVTNATELVQ SSSTGGICDS PHQILDGEAC TLIDALLGDP QCDGFQNKKW DLFVERSKAY SNCYPYDVPD YASLRSLVAS SGTLEFNDES FAWTGVTQAG TSSSCKRRSA NSFFSRLNWL TQLKFKYPAL AVTMPNNEKF DKLYIWGVHH PVTDNDQIFL YAQASGRITV STKRSQQTVI PNIGSRPRIR NIPSRISIYW TIVKPGDILL IASTGNLIAP RGYFKIRSGK SSIMRSDAPI GKCNSECITP NGSIPNDKPF QNVNRITYGA CPRYVKQNTL KLATGMRNVP EKQTRGIFGA IAGFIENGWE GMVDGWYGFR HQNSEGIGQA ADLKSTQAAI NQINGKLNRL IGKTNEKFHQ IEKEFSEVEG RIQDLEKYVE DTKIDLWSYN AELLVALENQ HTIDLTDSEM NKLFERTKKQ LRENAEDMGN GCFKIYHKCD NACIGSIRNG TYDHDVYRDE ALNNRFQIK SGRLVPRGSPGSGYIPEAPRDGQAYVRKDGEWVLLSTFLG HHHHHH |

TABLE 1-continued

| Sequence information | |
|---|---|
| SEQ ID NO: | Description of sequence |
| 5 | Amino acid sequence of HA-mut3 protein<br>MATLC LGHHAVPAGT IVKTITNDQI EVTAATELVQ SSSTGGICDS PHQILDGENC TLIDALLGDP<br>QCDGFQNKKW DLFVERSKAY SNCYPYDVPD YASLRSLVAS SGTLEFNDES FNWTGVTQNG TSSSCKRRSN<br>NSFFSRLNWL TQLKFKYPAL NVTMPNNEKF DKLYIWGVHH PVTDNDQIFL YAQASGRITV STKRSQQTVI<br>PNIGSRPRIR NIPSRISIYW TIVKPGDILL INSTGNLIAP RGYFKIRSGK SSIMRSDAPI GKDNSECITP<br>AGSIPNDKPF QNVNRITYGA CPRYVKQNTL KLATGMRNVP EKQTRGIFGA IAGFIENGWE GMVDGWYGFR<br>HQNSEGIGQA ADLKSTQAAI NQINGKLNRL IGKTNEKFHQ IEKEFSEVEG RIQDLEKYVE DTKIDLWSYN<br>AELLVALENQ HTIDLTDSEM NKLFERTKKQ LRENAEDMGN GCFKIYHKCD NACIGSIRAG TYDHDVYRDE<br>ALNNRFQIK SGRLVPRGSPGSGYIPEAPRDGQAYVRKDGEWVLLSTFLG HHHHHH |
| 6 | Full-length amino acid sequence of HA protein of influenza strain<br>A/HONG_KONG/4801/2014 (H3N2)<br>KTIIALSYILCLVFAQKIPGNDNSTATLCLGHHA VPNGTIVKTI TNDRIEVTNA TELVQNSSIG EICDSPHQIL<br>DGENCTLIDA LLGDPQCDGF QNKKWDLFVE RSKAYSNCYP YDVPDYASLR SLVASSGTLE FNNESFNWTG<br>VTQNGTSSAC IRRSSSSFFS RLNWLTHLNY KYPALNVTMP NNEQFDKLYI WGVHHPGTDK DQIFPYAWSS<br>GRIIVSTKRS QQAVIPNIGS RPRIRDIPSR ISIYWTIVKP GDILLINSTG NLIAPRGYFK LRSGKSSIMR<br>SDAPIGKCKS ECIPTNGSIP NDKPFQNVNR ITYGACPRYV KHSTLKLATG MRNVPEKQTR GIFGAIAGFI<br>ENGWEGMVDG WYGFRHQNSE GRGQAADLKS TQAAIDQING KLNRLIGKTN EKFHQIEKEF SEVEGRIQDL<br>EKYVEDTKID LWSYNAELLV ALENQHTIDL TDSEMNKLFE KTKKQLRENA EDMGNGCFKI YHKCDNACIG<br>SIRNGTYDHN VYRDEALNNR FQIKGVELDS GYKDWILWIS FAISCFLLCV ALLGFIMWAC QKGNIRCNIC I |
| 7 | Amino acid sequence of HK2014-WT-HA protein<br>MATLCLGHHA VPNGTIVKTI TNDRIEVTNA TELVQNSSIG EICDSPHQIL DGENCTLIDA LLGDPQCDGF<br>QNKKWDLFVE RSKAYSNCYP YDVPDYASLR SLVASSGTLE FNNESFNWTG VTQNGTSSAC IRRSSSSFFS<br>RLNWLTHLNY KYPALNVTMP NNEQFDKLYI WGVHHPGTDK DQIFPYAWSS GRIIVSTKRS QQAVIPNIGS<br>RPRIRDIPSR ISIYWTIVKP GDILLINSTG NLIAPRGYFK LRSGKSSIMR SDAPIGKCKS ECITPNGSIP<br>NDKPFQNVNR ITYGACPRYV KHSTLKLATG MRNVPEKQTR GIFGAIAGFI ENGWEGMVDG WYGFRHQNSE<br>GRGQAADLKS TQAAIDQING KLNRLIGKTN EKFHQIEKEF SEVEGRIQDL EKYVEDTKID LWSYNAELLV<br>ALENQHTIDL TDSEMNKLFE KTKKQLRENA EDMGNGCFKI YHKCDNACIG SIRNGTYDHN VYRDEALNNR<br>FQIK SGRLVPRGSPGSGYIPEAPRDGQAYVRKDGEWVLLSTFLGHHHHHH |
| 8 | Amino acid sequence of HK2014-DG-HA protein<br>MATLCLGHHA VPQGTIVKTI TNDRIEVTQA TELVQQSSIG EICDSPHQIL DGEQCTLIDA LLGDPQCDGF<br>QNKKWDLFVE RSKAYSNCYP YDVPDYASLR SLVASSGTLE FNQESFQWTG VTQQGTSSAC IRRSSSSFFS<br>RLNWLTHLNY KYPALQVTMP NNEQFDKLYI WGVHHPGTDK DQIFPYAQSS GRIIVSTKRS QQAVIPNIGS<br>RPRIRDIPSR ISIYWTIVKP GDILLIQSTG NLIAPRGYFK LRSGKSSIMR SDAPIGKCKS ECITPQGSIP<br>NDKPFQNVNR ITYGACPRYV KHSTLKLATG MRNVPEKQTR GIFGAIAGFI ENGWEGMVDG WYGFRHQNSE<br>GRGQAADLKS TQAAIDQING KLNRLIGKTN EKFHQIEKEF SEVEGRIQDL EKYVEDTKID LWSYNAELLV<br>ALENQHTIDL TDSEMNKLFE KTKKQLRENA EDMGNGCFKI YHKCDNACIG SIRQGTYDHN VYRDEALNNR<br>FQIK SGRLVPRGSPGSGYIPEAPRDGQAYVRKDGEWVLLSTFLGHHHHHH |
| 9 | Amino acid sequence of N-terminal signal peptide<br>MLLVNQSHQGFNKEHTSKMVAIVLYVLLAAAAHSAFA |
| 10 | Amino acid sequence of C-terminal folding motif<br>SGRLVPRGSPGSGYIPEAPRDGQAYVRKDGEWVLLSTFLG |
| 11 | Amino acid sequence of 6*His tag: HHHHHH |
| 12 | Amino acid sequence of mutant of HA protein of influenza strain<br>A/WISONSIN/67/2005 (H3N2)<br>ATLC LGHHAVPAGT IVKTITNDQI EVTAATELVQ SSSTGGICDS PHQILDGEAC TLIDALLGDP QCDGFQNKKW<br>DLFVERSKAY SNCYPYDVPD YASLRSLVAS SGTLEFNDES FAWTGVTQAG TSSSCKRRSA NSFFSRLNWL<br>TQLKFKYPAL AVTMPNNEKF DKLYIWGVHH PVTDNDQIFL YAQASGRITV STKRSQQTVI PNIGSRPRIR<br>NIPSRISIYW TIVKPGDILL IASTGNLIAP RGYFKIRSGK SSIMRSDAPI GKCNSECITP AGSIPNDKPF<br>QNVNRITYGA CPRYVKQNTL KLATGMRNVP EKQTRGIFGA IAGFIENGWE GMVDGWYGFR HQNSEGIGQA<br>ADLKSTQAAI NQINGKLNRL IGKTNEKFHQ IEKEFSEVEG RIQDLEKYVE DTKIDLWSYN AELLVALENQ<br>HTIDLTDSEM NKLFERTKKQ LRENAEDMGN GCFKIYHKCD NACIGSIRAG TYDHDVYRDE ALNNRFQIK |
| 13 | Amino acid sequence of mutant of HA protein of influenza strain<br>A/HONG_KONG/4801/2014 (H3N2)<br>ATLCLGHHA VPQGTIVKTI TNDRIEVTQA TELVQQSSIG EICDSPHQIL DGEQCTLIDA LLGDPQCDGF<br>QNKKWDLFVE RSKAYSNCYP YDVPDYASLR SLVASSGTLE FNQESFQWTG VTQQFTSSAC IRRSSSSFFS<br>RLNWLTHLNY KYPALQVTMP NNEQFDKLYI WGVHHPGTDK DQIFPYAQSS GRIIVSTKRS QQAVIPNIGS<br>RPRIRDIPSR ISIYWTIVKP GDILLIQSTG NLIAPRGYFK LRSGKSSIMR SDAPIGKCKS ECITPQGSIP<br>NDKPFQNVNR ITYGACPRYV KHSTLKLATG MRNVPEKQTR GIFGAIAGFI ENGWEGMVDG WYGFRHQNSE<br>GRGQAADLKS TQAAIDQING KLNRLIGKTN EKFHQIEKEF SEVEGRIQDL EKYVEDTDID LWSYNAELLV<br>ALENQHTIDL TDSEMNKLFE KTKKQLRENA EDMGNGCFKI YHKCDNACTG SIRQGTYDHN VYRDEALNNR<br>FQIK |

SPECIFIC MODELS FOR CARRYING OUT THE PRESENT INVENTION

The present invention will now be described with reference to the following examples which are intended to illustrate the present invention without limiting it.

Unless otherwise specified, the molecular biology experimental methods and immunoassays used in this application were performed by substantially referring to J. Sambrook et al., Molecular Cloning: A Laboratory Manual, 2nd Edition, Cold Spring Harbor Laboratory Press, 1989, and F M Ausubel et al., Short Protocols in Molecular Biology, 3rd Edition, John Wiley & Sons, Inc., 1995. Restriction enzymes were used in accordance with conditions recommended by the product manufacturers. If the specific conditions were not indicated in the examples, the conventional conditions or the conditions recommended by the manufacturers were used. If the reagents or instruments used were not specified by the manufacturer, they were all conventional products that were commercially available. Those skilled in the art know that the examples are used to illustratively describe the present invention, and are not intended to limit the scope of the present invention as claimed.

Example 1

Preparation of HA Protein of H3N2 Influenza Virus and Mutant Thereof (A) Design and Structure of HA Protein Mutant In the natural HA protein of influenza virus, the amino acid undergoing N-linked glycosylation is usually asparagine (N) in the characteristic sequence N-X-(S or T), in which N represents asparagine, X represents any one amino acid other than proline, S represents serine, and T represents threonine. In this example, the N-linked glycosylation site of HA protein was removed by mutating asparagine (N) in a characteristic sequence N-X-(S or T) in the natural HA protein to alanine (A).

The natural HA protein (WI2005-WT-HA) used in this example was the HA protein of H3N2 subtype influenza virus strain A/Wisconsin/67/2005. The HA protein of this strain contained the amino acid sequence as shown in SEQ ID NO: 1, wherein the amino acids 1 to 10 of SEQ ID NO: 1 were of a signal peptide, the amino acids 504 to 550 were of a transmembrane region, and, there were 10 potential N-linked glycosylation sites, namely asparagines (N) at positions 22, 38, 63, 126, 133, 144, 165, 246, 285 and 483. Among these N-linked glycosylation sites, with the exception of the asparagine at position 483 that was located in the HA2 subunit of HA protein, all asparagines at other positions were located in the HA1 subunit of HA protein. In addition, in terms of spatial structure, the asparagines at positions 22, 38, 285 and 483 were located in the stem region of the HA protein trimer; while the asparagines at positions 63, 126, 133, 144, 165 and 246 were located in the head region of the HA protein trimer.

Figure 1:
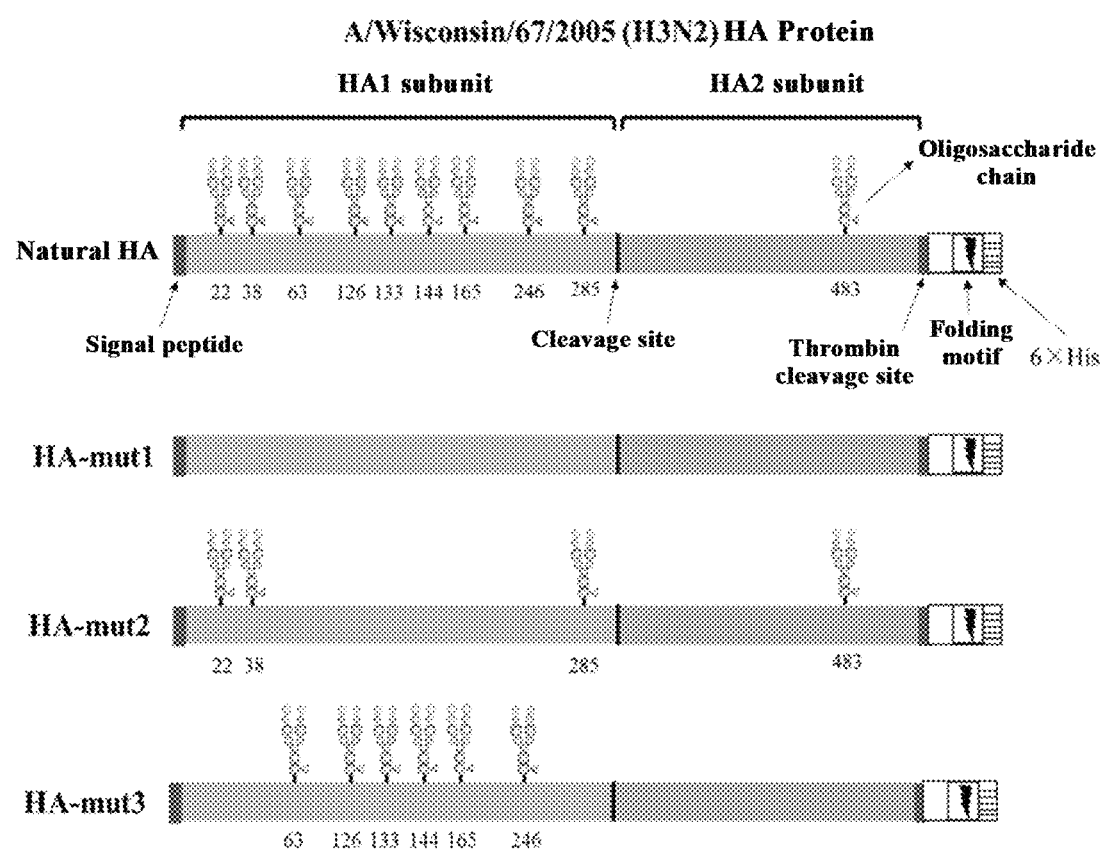

Based on the above structural information, the following natural HA protein and three HA protein mutants were designed in this example (FIG. 1):

(1) Natural HA protein (WI2005-WT-HA), which contained the amino acid sequence as shown in SEQ ID NO: 2, and differed from SEQ ID NO: 1 in that the amino acids 1 to 10 and 504 to 550 of SEQ ID NO: 1 were deleted, and a peptide segment (which contained sequences of SEQ ID NOs: 10 and 11, to facilitate the protein purification and trimer formation) containing a thrombin cleavage site, a folding motif, and a 6*His tag was introduced in the C-terminus of SEQ ID NO: 1. Accordingly, the trimer formed from the natural HA protein (WI2005-WT-HA) contained N-linked glycosyl chains in both the head and stem regions (FIG. 2A).

(2) HA-mut1, which contained the amino acid sequence shown in SEQ ID NO: 3, and differed from the natural HA protein (WI2005-WT-HA; SEQ ID NO: 2) in that the asparagine at each of the aforementioned 10 N-linked glycosylation sites was mutated to alanine. Accordingly, the trimer formed by HA-mut1 did not contain N-linked glycosyl chain in the head and stem regions (FIG. 2B).

(3) HA-mut2, which contained the amino acid sequence shown in SEQ ID NO: 4, and differed from the natural HA protein (WI2005-WT-HA; SEQ ID NO: 2) in that each of the asparagines located in the head region (i.e., at positions 63, 126, 133, 144, 165, and 246 of SEQ ID NO: 1) was mutated to alanine. Accordingly, the trimer formed by HA-mut2 did not contain N-linked glycosyl chain in the head region, but still contained N-linked glycosyl chains in the stem region (FIG. 2C).

(4) HA-mut3, which contained the amino acid sequence shown in SEQ ID NO: 5, and differed from the natural HA protein (WI2005-WT-HA; SEQ ID NO: 2) in that each of the asparagines located in the stem region (i.e., at positions 22, 38, 285, and 483 of SEQ ID NO: 1) was mutated to alanine. Accordingly, the trimer formed by HA-mut3 did not contain N-linked glycosyl chain in the stem region, but still contained N-linked glycosyl chains in the head region (FIG. 2D).

In addition, in order to facilitate the secretion of the protein, a nucleotide sequence encoding a signal peptide (SEQ ID NO: 9) was introduced at the 5' end of the nucleotide sequences encoding the natural HA protein, HA-mut1 protein, HA-mut2 protein and HA-mut3 protein. The expressed signal peptide was excised during protein secretion. Therefore, the finally obtained natural HA protein, HA-mut1 protein, HA-mut2 protein and HA-mut3 protein did not contain the signal peptide, and their amino acid sequences were shown in SEQ ID NOs: 2-5.

FIG. 1 schematically illustrates the sequence mutations and N-linked glycosylation of the natural HA protein, HA-mut1 protein, HA-mut2 protein and HA-mut3 protein used in Example 1 (note: the signal peptide would be excised during protein secretion). Specifically, the natural HA protein had asparagine at positions corresponding to the positions 22, 38, 63, 126, 133, 144, 165, 246, 285 and 483 of SEQ ID NO: 1, and thus could carry N-linked glycosyl chains at these positions. The HA-mut1 protein had alanine at positions corresponding to the positions 22, 38, 63, 126, 133, 144, 165, 246, 285 and 483 of SEQ ID NO: 1, and therefore no longer carried any N-linked glycosyl chains. The HA-mut2 protein had asparagine at positions corresponding to the positions 22, 38, 285 and 483 of SEQ ID NO: 1, and therefore could carry N-linked glycosyl chains at these positions; however, it had alanine at positions corresponding to the positions 63, 126, 133, 144, 165 and 246 of SEQ ID NO: 1, and therefore no longer carried any N-linked glycosyl chains at these positions. The HA-mut3 protein had asparagine at positions corresponding to the positions 63, 126, 133, 144, 165 and 246 of SEQ ID NO: 1, and therefore could carry N-linked glycosyl chains at these positions; however, it had alanine at positions corresponding to the positions 22, 38, 285 and 483 of SEQ ID NO: 1, and therefore no longer carried any N-linked glycosyl chains at these positions. In addition, in order to facilitate the secretion, purification and trimer formation of the protein, a signal peptide (which had an amino acid sequence as shown in SEQ ID NO: 9, and would be excised during protein secretion) was introduced into the N-terminus of the natural HA protein, HA-mut1 protein, HA-mut2 protein and HA-mut3 protein, respectively, and a peptide segment containing a thrombin cleavage site, a folding motif, and a 6*His tag (which contained amino acid sequences as shown in SEQ ID NOs: 10 and 11) was introduced into their C-terminus, respectively.

FIG. 2 schematically illustrates the schematic structure diagrams of the trimers formed with natural HA protein (FIG. 2A), HA-mut1 protein (FIG. 2B), HA-mut2 protein (FIG. 2C), and HA-mut3 protein (FIG. 2D) used in Example 1, respectively; in which FIG. 2A shows that the trimer formed by natural HA protein contained N-linked glycosyl chains in both the head and stem regions; FIG. 2B shows that the trimer formed by HA-mut1 protein contained no N-linked glycosyl chain in both the head and stem regions; FIG. 2C shows that the trimer formed by HA-mut2 protein did not contain N-linked glycosyl chain in the head region, but still contained N-linked glycosyl chain in the stem region; FIG. 2D shows that the trimer formed by HA-mut3 protein did not contain N-linked glycosyl chain in the stem region, but still contained N-linked glycosyl chain in the head region.

(B) Preparation of Transfer Plasmid

The DNA sequences separately encoding natural HA protein, HA-mut1 protein, HA-mut2 protein and HA-mut3 protein (for each of them, a signal peptide (SEQ ID NO: 9) was introduced into the N-terminus, and a peptide segment containing a thrombin cleavage site, a folding motif and a 6*His tag (SEQ ID NOs: 10 and 11) was introduced into the C-terminus) were synthesized by Shanghai Sangon Biotechnology Co., Ltd, and then these DNA sequences were cloned into baculovirus transfer vector pAcGP67-B (BD Company, Catalog Number: 554757), respectively. Subsequently, the transfer vectors carrying the DNA sequences of interest were separately transformed into competent cells of *E. coli* DH5a and amplified. A plasmid miniprep kit (TIANprep Mini Plasmid Kit; TianGen Corporation, Catalog Number: DP103-03) was used to extract the transfer plasmid containing the DNA sequence of interest from the transformed *E. coli* for later use.

(C) Co-Transfection 1 hour before transfection, $1\times10^6$ insect cells (Sf9 cells, Invitrogen) were plated on a 6-well culture plate and cultured in a serum-added medium. 1 μg of the transfer plasmid prepared in step (B), 0.1 μg of baculovirus linear DNA (BD), 1 μl of liposomes (Sigma), and 100 μl of serum-free cell culture medium were mixed and allowed to stand at room temperature for 30 minutes to obtain a transfection mixture. The serum-containing medium was removed from each well and the transfection mixture was added. After 6 hours of incubation at 27° C., the transfection mixture was removed from each well, and 2 ml of CCM3-containing medium was added to each well to continue culturing the cells. As a result, the transfer plasmid carrying the DNA sequence of interest and the baculovirus linear DNA were transfected into insect cells to produce a recombinant baculovirus.

(D) Production and Purification of Target Protein

The obtained recombinant baculovirus was passaged to obtain a second-generation recombinant baculovirus. 15 ml of the second-generation recombinant baculovirus was added to 1200 ml of Sf9 insect cells, and cultured at 27° C. for 48 hours. The cells and culture supernatant were collected and centrifuged at 11,500 rpm for 30 minutes. After centrifugation, the supernatant was collected, which contained the recombinantly produced target protein.

The supernatant containing the protein of interest was concentrated to 35 ml with an ultrafiltration concentration centrifuge tube from Millipore, adjusted to pH 7.4, and then centrifuged at 10,000 rpm for 10 minutes. The supernatant was collected, and Ni-NTA nickel ion chromatography column (NI-sepharose 6 fast flow, GE, Catalog Number: 17-5318-04) was used to enrich and purify the protein of interest in the supernatant, in which the eluent was PBS containing 250 mM imidazole. The eluate containing the protein of interest was concentrated to 1 ml, and dialyzed into PBS buffer, and stored at 4° C. for later use. Thus, the purified natural HA protein, HA-mut1 protein, HA-mut2 protein and HA-mut3 protein were obtained (the N-terminal signal peptide was excised during the secretion process, so the obtained protein retained the folding motif and 6*His tag, but did not contain the N-terminal signal peptide).

(E) Preparation of HAmg and HAug Proteins

In addition, by referring to the method described in Juine-Ruey Chen et al. (Proc Natl Acad Sci, USA. 2014 Feb. 18; 111 (7): 2476-81), the natural HA protein (WI2005-WT-HA) was subjected to enzymatic treatment by using endoglycosidase H and endoglycosidase F to prepare an HA protein carrying a single glycosyl group at N-linked glycosylation site (hereinafter referred to as HAmg) and an HA protein substantially carrying no glycosyl group at N-linked glycosylation site (hereinafter referred to as HAug).

It should be noted that due to the restriction of enzymatic action and the inaccessibility of some glycosylation sites, HAug inevitably still carries a small amount of glycosyl groups at N-linked glycosylation sites, which can also be confirmed by the data provided in Table 51 of Juine-Ruey Chen et al. (Ibid.). In contrast, since asparagine at each of all N-linked glycosylation sites has been replaced with alanine, the HA-mut1 protein no longer carries any N-linked glycosyl groups.

Example 2

Polyacrylamide Gel Electrophoresis (SDS-PAGE) Analysis

Polyacrylamide gel electrophoresis (SDS-PAGE) was used to analyze the six proteins (natural HA protein, HA-mut1, HA-mut2, HA-mut3, HAmg, and HAug) prepared in Example 1. The upper gel used was 5% concentrated gel (prepared as follows: 830 μl of 30% acrylamide, 630 μl of 1M Tris (pH6.8), 50 μl of 10% SDS, 50 μl of 10% ammonium persulfate, and 5 μl of TEMED were added into 3.4 ml of water). The lower gel used was 12% separation gel (prepared as follows: 4 ml of 30% acrylamide, 2.5 ml of 1M Tris (pH8.8), 100 μl of 10% SDS, 100 μl of 10% ammonium persulfate, and 10 μl of TEMED were added to 3.3 ml of water). The electrophoresis condition used was that electrophoresis was performed at 150 V for 2 hours. After electrophoresis, the polyacrylamide gel was stained with Coomassie brilliant blue (Sigma). The experimental results are shown in FIG. 3.

FIG. 3 shows the results of SDS-PAGE analysis of six proteins prepared in Example 1. FIG. 3A shows the results of SDS-PAGE analysis of natural HA protein, HA-mut3, HA-mut2, and HA-mut1 proteins; FIG. 3B shows the results of SDS-PAGE analysis of natural HA protein, HAmg protein and HAug protein. The results in FIG. 3 show that the molecular weight of natural HA protein is above 70 kD, while the molecular weights of HA-mut3, HA-mut2, HA-mut1, HAmg and HAug proteins are all significantly reduced, all below 70 kD, and the HA-mut1 protein has the smallest molecular weight.

Example 3

Evaluation of Neutralizing Activity of Antisera (A) Immune Experiment

6-Week-old, SPF-grade, female Balb/C mice were provided by the Experimental Animal Center of Xiamen University, and had a body weight of approximately 20 g. The six proteins (natural HA protein, HA-mut1, HA-mut2, HA-mut3, HAmg and HAug) prepared in Example 1 and PBS (used as negative control) were separately mixed with aluminum adjuvant in a volume ratio of 1:1, and used to immunize the mice. The immunization schedule was as follows: 6 mice were used in each group; the immunization method was intramuscular injection; the immunization dose was 5 μg protein/mouse; the injection volume was 100 μl/mouse; the immunization was performed twice with an interval of 14 days. Fourteen days after the second immunization, serum was collected from each mouse. The collected serum samples were inactivated at 56° C. for 30 minutes, and then stored at −20° C. for later use.

(B) Evaluation of Neutralizing Titers of Serum Samples

Neutralization titer is an important indicator for evaluating whether a serum sample has the potential to prevent and treat a disease. In this experiment, a plaque reduction neutralization test (PRNT) was used to analyze the neutralizing antibody titers of the collected serum samples. The influenza viruses used were representative strains of influenza viruses isolated at different time, from different regions and representing different subtypes (H3N2, H7N9 and H1N1), in which the specific virus strains were as follows: A/Wisconsin/67/2005 (H3N2 subtype), A/Victoria/361/2011 (H3N2 subtype), A/Beijing/32/1992 (H3N2 subtype), A/Aichi/2/1968 (H3N2 subtype), A/Shanghai/02/2013 (H7N9 subtype) and A/California/04/2009 (H1N1 subtype).

$6 \times 10^5$ MDCK cells were seeded in a 6-well cell culture plate. The influenza viruses used were diluted to 50 PFU/50 μl in MEM medium containing 0.5 μg/ml TPCK trypsin. Then, serially diluted serum samples were mixed with influenza viruses and incubated at 37° C. for 1 hour, and then added to a 6-well cell culture plate seeded with MDCK cells, and the incubation was continued at 37° C. for 1 hour. After incubation, the cell culture fluid was sucked out and the cells were washed twice with PBS. Then, the cell surface was covered with 0.5% agarose-containing MEM medium, and the cells were placed in a constant temperature incubator at 5% $CO_2$ and 37° C. for 2 days. After that, the cells were stained with 2% crystal violet, and the titers of influenza viruses were determined by counting the number of plaques, and then the neutralizing activity of each serum sample was calculated. The results are shown in FIGS. 4-5.

Figure 4:
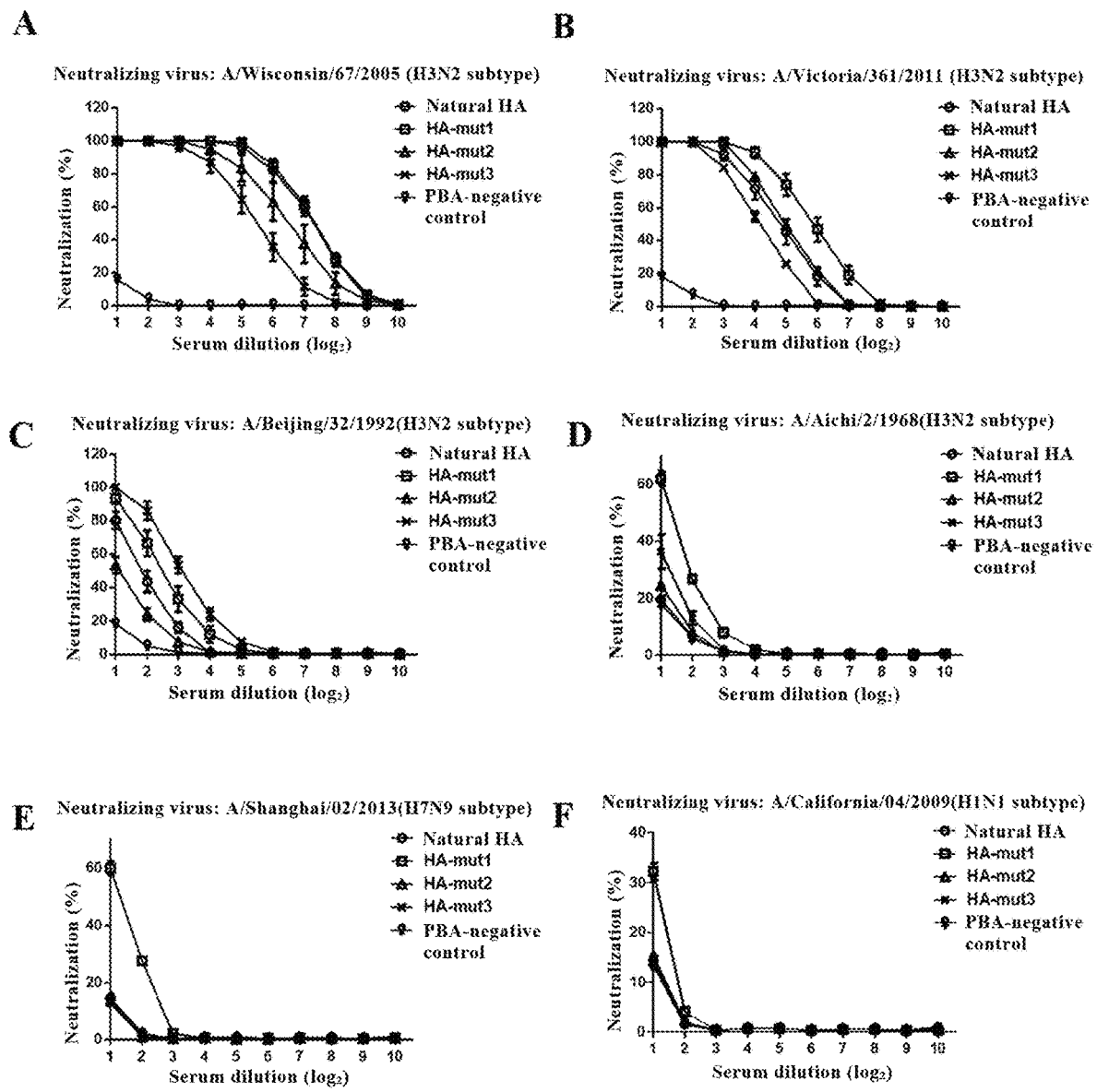
FIG. 4 shows the neutralizing activities against influenza viruses A/Wisconsin/67/2005 (H3N2 subtype) (FIG. 4A), A/Victoria/361/2011 (H3N2 subtype) (FIG. 4B), A/Beijing/32/1992 (H3N2 subtype) (FIG. 4C), A/Aichi/2/1968 (H3N2 subtype) (FIG. 4D), A/Shanghai/02/2013 (H7N9 subtype) (FIG. 4E), and A/California/04/2009 (H1N1 subtype) (FIG. 4F) of mouse sera as obtained by immunizing mice with natural HA protein, HA-mut1, HA-mut2, HA-mut3 and PBS (used as negative control) as an immunogen, respectively.
Figure 5:
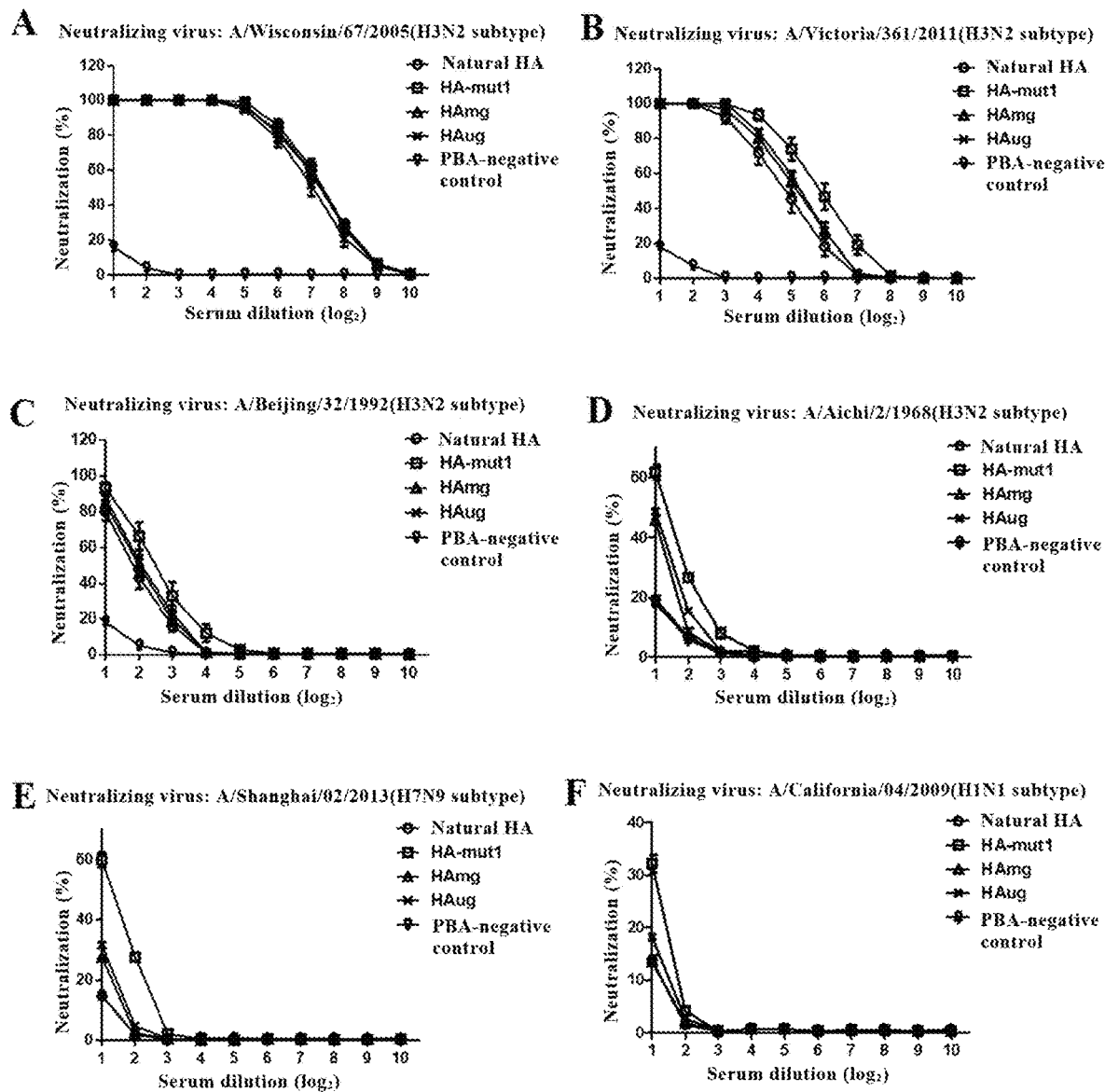
FIG. 5 shows the neutralizing activities against influenza viruses A/Wisconsin/67/2005 (H3N2 subtype) (FIG. 5A), A/Victoria/361/2011 (H3N2 subtype) (FIG. 5B), A/Beijing/32/1992 (H3N2 subtype) (FIG. 5C), A/Aichi/2/1968 (H3N2 subtype) (FIG. 5D), A/Shanghai/02/2013 (H7N9 subtype) (FIG. 5E), and A/California/04/2009 (H1N1 subtype) (FIG. 5F) of mouse sera as obtained by immunizing mice with natural HA protein, HA-mut1, HAmg, HAug and PBS (used as negative controls) as an immunogen, respectively.

FIG. 4 shows the neutralizing activities against influenza viruses A/Wisconsin/67/2005 (H3N2 subtype) (FIG. 4A), A/Victoria/361/2011 (H3N2 subtype) (FIG. 4B), A/Beijing/32/1992 (H3N2 subtype) (FIG. 4C), A/Aichi/2/1968 (H3N2 subtype) (FIG. 4D), A/Shanghai/02/2013 (H7N9 subtype) (FIG. 4E), and A/California/04/2009 (H1N1 subtype) (FIG. 4F) of mouse sera as obtained by immunizing mice with natural HA protein, HA-mut1, HA-mut2, HA-mut3 and PBS (used as negative control) as an immunogen, respectively.

As shown in FIG. 4A, for the influenza virus strain A/Wisconsin/67/2005 from which the HA protein used in this experiment was derived, the mouse sera obtained from mice immunized with natural HA protein, HA-mut1, HA-mut2 or HA-mut3 all had strong neutralizing activities, in which the sera obtained from mice immunized with natural HA protein and HA-mut1 had the highest neutralizing titer, and the serum obtained from mice immunized with HA-mut3 had the lowest neutralizing titer.

As shown in FIG. 4B, for the H3N2 subtype virus strain A/Victoria/361/2011, which had a close evolutionary relationship with the HA protein used in this experiment, the serum obtained from mice immunized with HA-mut1 had the highest neutralizing titer (even higher than the serum obtained from mice immunized with natural HA protein), and the serum obtained from mice immunized with HA-mut3 had the lowest neutralizing titer.

As shown in FIG. 4C, for the H3N2 subtype virus strain A/Beijing/32/1992, which had a farther evolutionary relationship with the HA protein used in this experiment, the serum obtained from mice immunized with HA-mut3 had the highest neutralizing titer, the serum obtained from mice immunized with HA-mut1 had the second high neutralizing titer (both were higher than the serum obtained from mice immunized with natural HA protein), and the serum obtained from mice immunized with HA-mut2 had the lowest neutralizing titer.

As shown in FIG. 4D, for the H3N2 subtype virus strain A/Aichi/2/1968, which had the farthest evolutionary relationship with the HA protein used in this experiment, the serum obtained from mice immunized with HA-mut1 had the highest neutralizing titer, the serum obtained from mice immunized with HA-mut3 had the second high neutralizing titer, and the serum obtained from mice immunized with natural HA protein or HA-mut2 substantially had no neutralizing activity (no significant difference from the negative control).

As shown in FIG. 4E and FIG. 4F, for the virus strains A/Shanghai/02/2013 (H7N9 subtype) and A/California/04/2009 (H1N1 subtype) that belonged to different subtypes from the HA protein used in this experiment, only the serum obtained from mice immunized with HA-mut1 had neutralizing activity, while the sera obtained from mice immunized with other proteins had substantially no neutralizing activity (no significant difference from the negative control).

The results in FIG. 4 show that the serum obtained from mice immunized with HA-mut1 had the broadest spectrum of neutralizing activity, which not only can effectively neutralize multiple virus strains of H3N2 subtype (regardless of the distance of evolutionary relationship), but also can neutralize strains of other subtypes (e.g., stains of H7N9 and H1N1 subtypes). In contrast, the sera obtained from mice immunized with natural HA protein, HA-mut2 and HA-mut3 had neutralizing activity only on some strains of H3N2 subtype, and had no neutralizing activity on strains of other subtypes. Thus, HA-mut1 is particularly suitable as a broad-spectrum vaccine for inducing protective antibodies with broad-spectrum neutralizing activity in vivo.

FIG. 5 shows the neutralizing activities against influenza viruses A/Wisconsin/67/2005 (H3N2 subtype) (FIG. 5A), A/Victoria/361/2011 (H3N2 subtype) (FIG. 5B), A/Beijing/32/1992 (H3N2 subtype) (FIG. 5C), A/Aichi/2/1968 (H3N2 subtype) (FIG. 5D), A/Shanghai/02/2013 (H7N9 subtype) (FIG. 5E), and A/California/04/2009 (H1N1 subtype) (FIG. 5F) of the mouse sera as obtained by immunizing mice with natural HA protein, HA-mut1, HAmg, HAug and PBS (used as negative controls) as an immunogen, respectively.

As shown in FIG. 5A, for the influenza virus strain A/Wisconsin/67/2005 from which the HA protein used in this experiment was derived, the sera obtained from mice immunized with natural HA protein, HA-mut1, HAmg or HAug had strong neutralizing activity with comparable potency.

As shown in FIG. 5B, for the H3N2 subtype virus strain A/Victoria/361/2011, which had a close evolutionary relationship with the HA protein used in this experiment, the serum obtained from mice immunized with HA-mut1 had the highest neutralizing titer, and the serum obtained from mice immunized with natural HA protein had the lowest neutralizing titer.

As shown in FIG. 5C, for the H3N2 subtype virus strain A/Beijing/32/1992, which had a farther evolutionary relationship with the HA protein used in this experiment, the serum obtained from mice immunized with HA-mut1 had the highest neutralizing titer, and the sera obtained from mice immunized with other proteins had lower and comparable neutralizing titers between each other.

As shown in FIG. 5D, for the H3N2 subtype virus strain A/Aichi/2/1968, which had the farthest evolutionary relationship with the HA protein used in this experiment, the serum obtained from mice immunized with HA-mut1 had highest neutralizing titer, the serum obtained from mice immunized with HAmg or HAug had the second high neutralizing titer (the two were comparable), while the serum obtained by mice with natural HA protein substantially had no neutralizing activity (no significant difference from the negative control).

As shown in FIG. 5E, for the virus strain A/Shanghai/02/2013 (H7N9 subtype) that belonged to a different subtype from the HA protein used in this experiment, the serum obtained from mice immunized with HA-mut1 had the highest neutralizing titer, the serum obtained from mice immunized with HAmg or HAug had the second high neutralizing titer (the two were comparable), while the serum obtained by mice with natural HA protein substantially had no neutralizing activity (no significant difference from the negative control).

As shown in FIG. 5F, for the virus strain A/California/04/2009 (H1N1 subtype) that belonged to a different subtype from the HA protein used in this experiment, only the serum obtained from mice immunized with HA-mut1 had neutralizing activity, while the sera obtained from mice immunized with other proteins substantially had no neutralizing activity (no significant difference from the negative control).

The results in FIG. 5 show that the serum obtained from mice immunized with natural HA protein only has neutralizing activity against H3N2 subtype influenza virus; the sera obtained from mice immunized with HAmg and HAug not only can neutralize H3N2 subtype influenza virus, but also show weak neutralizing activity across HA subtypes (capable of neutralizing H7N9 subtype, but not neutralizing H1N1 subtype); the serum obtained from mice immunized with HA-mut1 has the broadest spectrum of neutralizing activity and the highest neutralizing titer, which not only can effectively neutralize multiple virus strains of H3N2 subtypes (regardless of the distance of evolutionary relationship), but also has strong neutralizing activity across HA subtypes (for example, capable of neutralizing the strains of H7N9 and H1N1 subtypes). It can be seen that HA-mut1 is particularly suitable as a broad-spectrum vaccine for inducing protective antibodies with broad-spectrum neutralizing activity in vivo.

Example 4

Evaluation of In Vivo Protective Activity

The PRNT experiment in Example 3 confirmed that the neutralizing titers on the H3N2 subtype, H7N9 subtype, and H1N1 subtype virus strains of the antisera induced by the six proteins prepared in Example 1 were different, among which the antiserum induced by HA-mut1 had the broadest spectrum of neutralizing activity. In order to further verify the effect of these six proteins in inducing immune protection against influenza virus in animals, the present inventors evaluated the in vivo antiviral efficacy of these six proteins in a biosafety laboratory, based on the mouse animal models infected with influenza viruses A/Beijing/32/1992 (H3N2 subtype), A/Aichi/02/1968 (H3N2 subtype), A/Shanghai/02/2013 (H7N9 subtype) and A/California/04/2009 (H1N1 subtype). The specific scheme is as follows.

Materials and Methods

Animals: Balb/C mice, SPF grade, 6-8 weeks old, female, body weigh about 20 g.

Vaccines: Natural HA protein, HA-mut1 protein, HA-mut2 protein, HA-mut3 protein, HAmg protein, HAug protein and PBS (used as negative control).

Immunization scheme: The natural HA protein, HA-mut1 protein, HA-mut2 protein, HA-mut3 protein, HAmg protein, HAug protein and PBS negative control were separately mixed with aluminum adjuvant in a volume ratio of 1:1 and used for immunization of mice. Six mice were used in each group, and immunized by intramuscular injection; the immunization dose was 5 µg protein/mouse, and the injection volume was 100 µl/mouse. The immunization was performed twice with an interval of 14 days between the two immunizations. Fourteen days after the second immunization, the mice were challenged with viruses. The following influenza virus strains were used:

mouse adaptive strain of H3N2 subtype influenza virus: A/Beijing/32/1992;

mouse adaptive strain of H3N2 subtype influenza virus: A/Aichi/02/1968;

mouse adaptive strain of H7N9 subtype influenza virus: A/Shanghai/02/2013;

mouse adaptive strain of H1N1 subtype influenza virus: A/California/04/2009.

Anesthetic: Isoflorane.

Animal grouping: mice were sent to the biosafety laboratory one day in advance, grouped as 6 mice in one cage, and the weight of each mouse was recorded.

Virus infection: The challenge dose of each virus was 25 times the median lethal dose ($LD_{50}$), and the virus inoculation volume was 50 µl/mouse. Before inoculation, the mice were anesthetized with isophorane, and then the mice were inoculated with viruses through nasal cavity.

Observations: The changes in body weight and survival of mice were recorded daily from 1 to 14 days after virus infection. The experimental results are shown in FIGS. 6-9.

FIG. 6 shows the changes in weight and survival of mice immunized with natural HA protein, HA-mut1 protein, HA-mut2 protein, HA-mut3 protein or PBS (negative control) after infection with the H3N2 subtype influenza viruses A/Beijing/32/1992 (H3N2) (FIGS. 6A-6B) and A/Aichi/2/1968 (H3N2) (FIGS. 6C-6D) which are prevalent at early ages, in which FIG. 6A and FIG. 6C show the changes in body weight of each group of experimental mice, and FIG. 6B and FIG. 6D show the survival rate of each group of experimental mice. The results of FIGS. 6A-6B show that the mice immunized with HA-mut1 or HA-mut3, after being infected with a lethal dose of virus A/Beijing/32/1992, began to recover body weight after the day 7, and the mouse survival rate was 100% at the end of experiment; however, the mice immunized with natural HA protein, HA-mut2 or PBS all continuously lost body weight and all died before the end of experiment. This result indicates that HA-mut1 and HA-mut3 have complete protection and can be used as vaccines against A/Beijing/32/1992. The results of FIGS. 6C-6D show that after the mice immunized with HA-mut1 were infected with a lethal dose of virus A/Aichi/2/1968, their body weight began to recover after the day 4, and the mouse survival rate was 100% at the end of the experiment; HA-mut3 has partial protection to the mice infected with a lethal dose of virus A/Aichi/2/1968, and the mouse survival rate was 33.3% at the end of the experiment; however, the mice immunized with natural HA protein, HA-mut2 or PBS all continuously lost body weight and all died before the end of the experiment. This result indicates that HA-mut1 has full protection and can be used as a vaccine against A/Aichi/2/1968.

Figure 7:
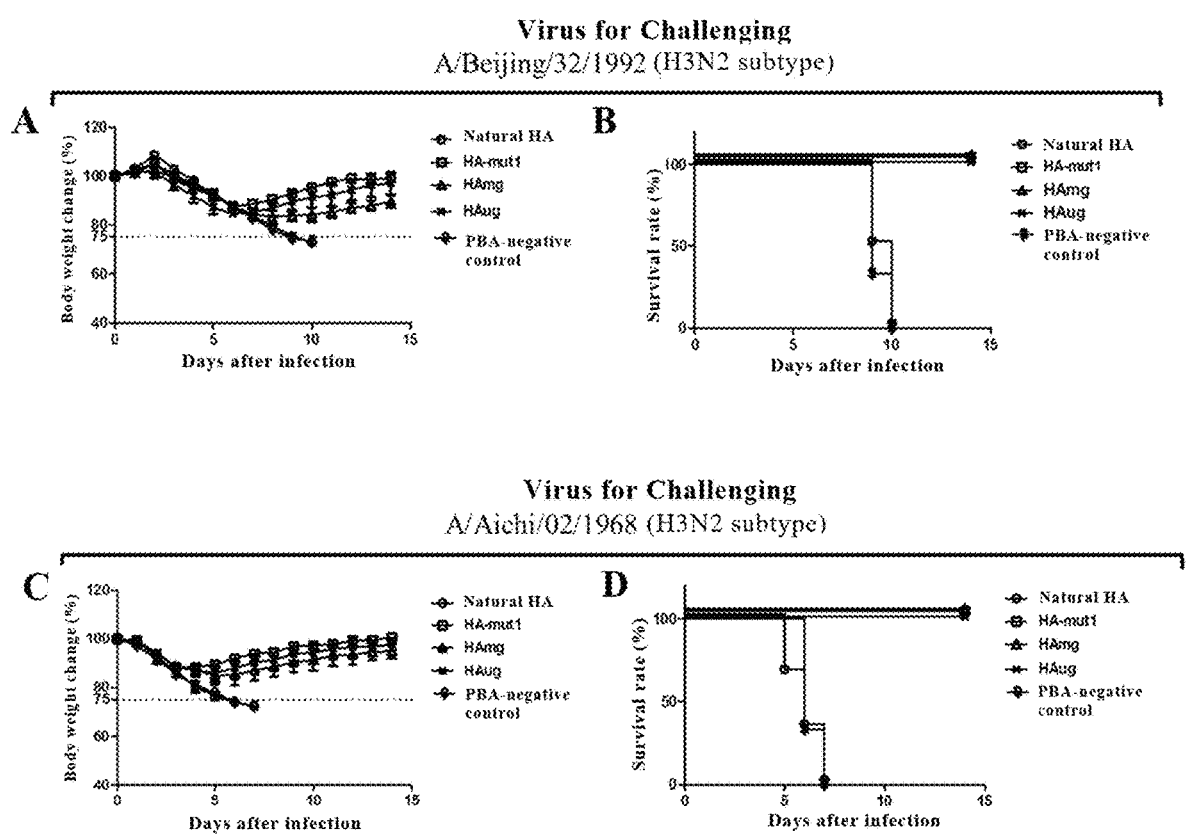

FIG. 7 shows the changes in weight and survival of mice immunized with natural HA protein, HA-mut1 protein, HAmg protein, HAug protein or PBS (negative control) after infection with H3N2 subtype influenza viruses A/Beijing/32/1992 (H3N2) (FIGS. 7A-7B) and A/Aichi/2/1968 (H3N2) (FIGS. 7C-7D), in which FIG. 7A and FIG. 7C show the changes in body weight of each group of experimental mice, and FIG. 7B and FIG. 7D show the survival rate of each group of experimental mice. The results of FIGS. 7A-7B show that after the mice immunized with HA-mut1 protein, HAmg protein or HAug protein were infected with a lethal dose of virus A/Beijing/32/1992, their body weight began to recover after the day 7 (the mice immunized with HA-mut1 showed the best weight recovery effect), and the mouse survival rate was 100% at the end of the experiment; however, the mice immunized with natural HA protein or PBS all continuously lost body weight and all died before the end of the experiment. This result indicates that HA-mut1 protein, HAmg protein and HAug protein have complete protection and can be used as vaccines against A/Beijing/32/1992. The results of FIGS. 7C-7D show that after the mice immunized with HA-mut1, HAmg or HAug were infected with a lethal dose of virus A/Aichi/2/1968, their body weight began to recover after the day 4 or 5 (the mice immunized with HA-mut1 showed the best weight recovery effect), and the mouse survival rate was 100% at the end of the experiment; however, the mice immunized with natural HA protein or PBS all continuously lost body weight and all died before the end of the experiment. This result indicates that HA-mut1 protein, HAmg protein and HAug protein have complete protection and can be used as vaccines against A/Aichi/2/1968.

Figure 8:
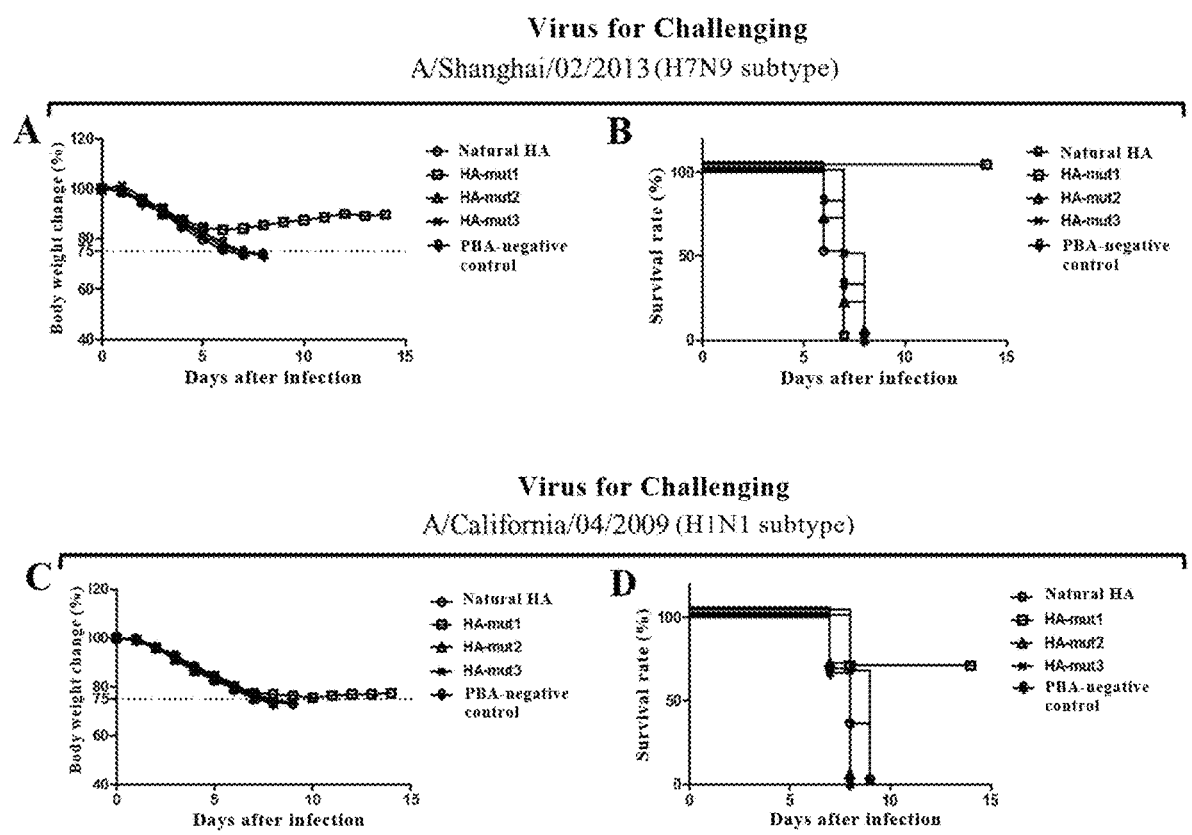

FIG. 8 shows the changes in weight and survival of mice immunized with natural HA protein, HA-mut1 protein, HA-mut2 protein, HA-mut3 protein or PBS (negative control) after infection with non-H3N2 subtype influenza viruses A/Shanghai/02/2013 (H7N9) (FIGS. 8A-8B) and A/California/04/2009 (H1N1) (FIGS. 8C-8D), in which FIG. 8A and FIG. 8C show the changes in body weight of each group of experimental mice, and FIG. 8B and FIG. 8D show the survival rate of each group of experimental mice. The results of FIGS. 8A-8B show that after the mice immunized with HA-mut1 were infected with a lethal dose of virus A/Shanghai/02/2013 (H7N9), their body weight began to recover after the day 6, and the mouse survival rate was 100% at the end of the experiment; however, the mice immunized with natural HA protein, HA-mut2, HA-mut3 or PBS all continuously lost body weight and all died before the end of the experiment. This result indicates that HA-mut1 has complete protection and can be used as a vaccine against A/Shanghai/02/2013. The results of FIGS. 8C-8D show that, after the mice immunized with HA-mut1 were infected with a lethal dose of virus A/California/04/2009 (H1N1), their body weight remained stable after the day 8 and did not decrease anymore, and the mouse survival rate was 66.7% at the end of experiment; however, the mice immunized with natural HA protein, HA-mut2, HA-mut3 or PBS all continuously lost body weight and all died before the end of the experiment. This result indicates that HA-mut1 has a strong in vivo protective effect against influenza virus A/California/04/2009 (H1N1).

Figures 9, 10:
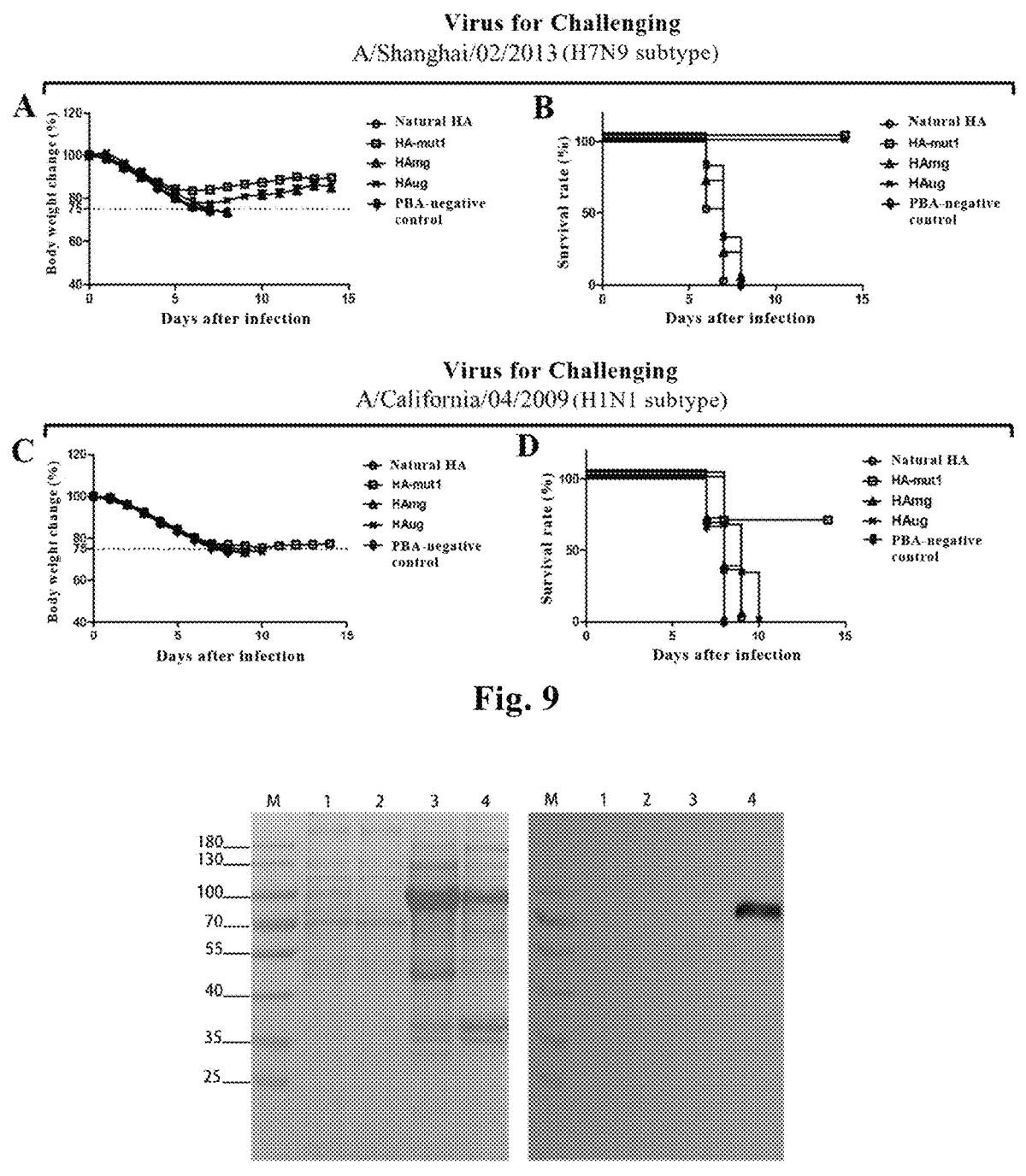

FIG. 9 shows the changes in weight and survival of mice immunized with natural HA protein, HA-mut1 protein, HAmg protein, HAug protein or PBS (negative control) after infection with non-H3N2 subtype influenza viruses A/Shanghai/02/2013 (H7N9) (FIGS. 9A-9B) and A/California/04/2009 (H1N1) (FIGS. 9C-9D), in which FIGS. 9A and 9C show the changes in body weight of each group of experimental mice, and FIG. 9B and FIG. 9D shows the survival rate of each group of experimental mice. The results of FIGS. 9A-9B show that after the mice immunized with HA-mut1 protein or HAug protein were infected with a lethal dose of virus A/Shanghai/02/2013 (H7N9), their body weight began to recover after the day 6 or 7 (the mice immunized with HA-mut1 showed the best weight recovery effect), and the mouse survival rate was 100% at the end of the experiment; however, the mice immunized with natural HA protein, HAmg protein or PBS all continuously lost body weight and all died before the end of the experiment. This result indicates that HA-mut1 protein and HAug protein have complete protection and can be used as vaccines against A/Shanghai/02/2013 (H7N9). The results of FIGS. 9C-9D show that after the mice immunized with HA-mut1 were infected with a lethal dose of the virus A/California/04/2009 (H1N1), their body weight remained stable after the day 8 and did not decrease any more, and the mice survival rate was 66.7% at the end of experiment; however, the mice immunized with natural HA protein, HAmg, HAug or PBS all continuously lost body weight and all died before the end of the experiment. This result indicates that HA-mut1 has a strong in vivo protective effect against influenza virus A/California/04/2009 (H1N1).

The above experimental results show that HA-mut1 protein as a vaccine can effectively prevent influenza virus infections of H3N2 subtypes (regardless of the distance of evolutionary relationship), H7N9 subtypes and H1N1 subtypes, and diseases caused thereby, and thus can be used as an effective, broad-spectrum vaccine against multiple subtypes of influenza viruses.

Example 5

Preparation and Analysis of H3N2 Influenza Virus HA Protein and its Mutants

In this example, the N-linked glycosylation site of HA protein was removed by mutation of asparagine (N) in the characteristic sequence N-X-(S or T) in natural HA protein to glutamine (Q).

The natural HA protein (HK2014-WT-HA) used in this example was the HA protein of H3N2 subtype influenza virus strain A/HONG_KONG/4801/2014 (H3N2). The HA protein of this strain contained the amino acid sequence shown in SEQ ID NO: 6, wherein the amino acids 1 to 25 of SEQ ID NO: 6 were of a signal peptide, and the amino acids 518 to 565 were of a transmembrane region, and it had 11 potential N-linked glycosylation sites, i.e., asparagines (N) at positions 37, 53, 60, 78, 137, 141, 148, 180, 261, 300 and 498.

Based on the above structural information, the natural HA protein HK2014-WT-HA and its mutant HK2014-DG-HA were designed in this example:

(1) Natural HA protein (HK2014-WT-HA), which contained the amino acid sequence shown in SEQ ID NO: 7, and which differed from SEQ ID NO: 6 in that the amino acids 1 to 25 and 518 to 565 of SEQ ID NO: 6 were deleted, and a peptide segment containing a thrombin cleavage site, a folding motif, and a 6*His tag (which contained the sequences of SEQ ID NO: 10 and 11 to facilitate protein purification and trimer formation) was introduced into the C-terminus of SEQ ID NO: 6. Accordingly, the trimer formed by the natural HA protein (HK2014-WT-HA) contained N-linked glycosyl chains in both the head and stem regions.

(2) Mutant HK2014-DG-HA, which contained the amino acid sequence shown in SEQ ID NO: 8, and which differed from the natural HA protein (HK2014-WT-HA; SEQ ID NO: 7) in that the asparagine (N) at each of the aforementioned 11 N-linked glycosylation sites was mutated to glutamine (Q). Accordingly, the trimer formed by the mutant HK2014-DG-HA did not contain N-linked glycosyl chain in both the head and stem regions.

In addition, in order to facilitate the secretion of protein, a nucleoside sequence encoding a signal peptide (SEQ ID NO: 9) was introduced at the 5' end of the nucleotide sequence encoding the natural HA protein HK2014-WT-HA and the mutant protein HK2014-DG-HA. The expressed signal peptide would be excised during protein secretion. Therefore, neither the finally obtained natural HA protein HK2014-WT-HA nor its mutant HK2014-DG-HA contained a signal peptide, and their amino acid sequences were shown in SEQ ID NOs: 7-8.

The DNA sequences separately encoding the natural protein HK2014-WT-HA and mutant protein HK2014-DG-HA (for each of them, a signal peptide (SEQ ID NO: 9) was introduced into the N-terminus, and a peptide segment (SEQ ID NOs: 10 and 11) containing a thrombin cleavage site, a folding motif and a 6*His tag was introduced into the C-terminus) were cloned into a baculovirus transfer vector pAcGP67-B (BD Company, Catalog Number: 554757), respectively. Subsequently, the transfer vectors carrying the DNA sequences of interest were transformed into competent cells of *E. coli* DH5a and amplified. A plasmid miniprep kit (TIANprep Mini Plasmid Kit; TianGen Corporation, Catalog Number: DP103-03) was used to extract the transfer plasmids containing the DNA sequences of interest from the transformed *E. coli* for later use.

Subsequently, as described in Example 1, a recombinant baculovirus containing the DNA sequence of interest was constructed using the transfer plasmid prepared as described above, and cultured in Sf9 insect cells. After the culture, the cells and the culture supernatant were collected and centrifuged at 11,500 rpm for 30 minutes. After centrifugation, the supernatant was collected, which contained the recombinantly produced target protein. Then, as described in Example 1, the proteins of interest, i.e., HK2014-WT-HA and HK2014-DG-HA (the N-terminal signal peptide was excised during the secretion process, so the obtained proteins retained the folding motif and 6*His tag, but did not contain the N-terminal signal peptide), in the supernatant was enriched and purified by Ni-NTA nickel ion chromatography column (NI-sepharose 6 fast flow, GE, Catalog Number: 17-5318-04) using PBS containing imidazole (50 mM or 250 mM) as an eluent.

In addition, by referring to the method described in Juine-Ruey Chen et al. (Proc Natl Acad Sci, USA. 2014 Feb. 18; 111 (7): 2476-81), the natural HA protein (HK2014-WT-HA) obtained as above was subjected to enzymatic treatment by using endoglycosidase F to prepare a deglycosylated HA protein (hereinafter referred to as HK2014-HAug) which did not substantially carry glycosyl group at all N-linked glycosylation sites.

SDS polyacrylamide gel electrophoresis (SDS-PAGE) and Western blot (the used antibody was: HRP-conjugated 6*His, His-Tag Antibody, Proteintech, Catalog Number: HRP-66005) were used to analyze the above prepared 3 proteins (HK2014-WT-HA, HK2014-DG-HA and HK2014-HAug). The experimental results are shown in FIGS. 10-12.

FIG. 10 shows the results of SDS-PAGE analysis (left panel) and Western blot analysis (right panel) of HK2014-WT-HA protein; in which lane M: molecular weight marker; lane 1: sample without being purified by Ni-NTA nickel ion chromatography column; lane 2: fraction flowing through Ni-NTA nickel ion chromatography column; lane 3: fraction being eluted with 50 mM imidazole; lane 4: fraction being eluted with 50 mM imidazole; lane 5: fraction being eluted with 250 mM imidazole; the arrow indicates the position of the protein of interest, HK2014-WT-HA.

Figure 11:
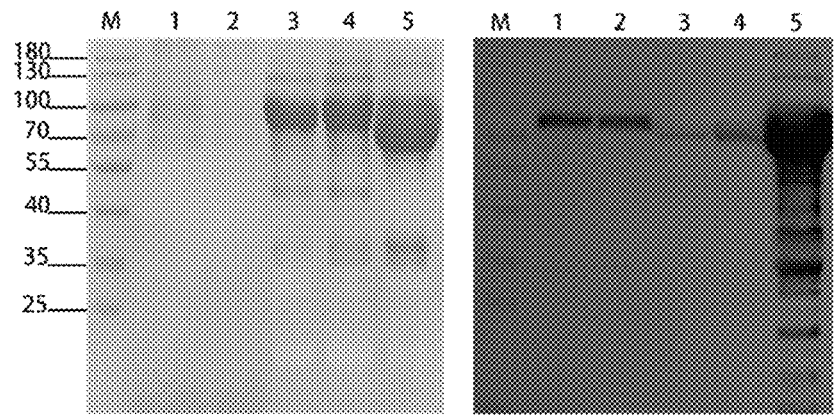
FIG. 11 shows the results of SDS-PAGE analysis (left panel) and Western blot analysis (right panel) of HK2014-DG-HA protein; in which lane M: molecular weight marker; lane 1: sample without being purified with Ni-NTA nickel ion chromatography column; lane 2: fraction flowing through Ni-NTA nickel ion chromatography column; lane 3: fraction being eluted with 50 mM imidazole; lane 4: fraction being eluted with 250 mM imidazole; the arrow indicates the position of the protein HK2014-DG-HA of interest.
Figure 12:
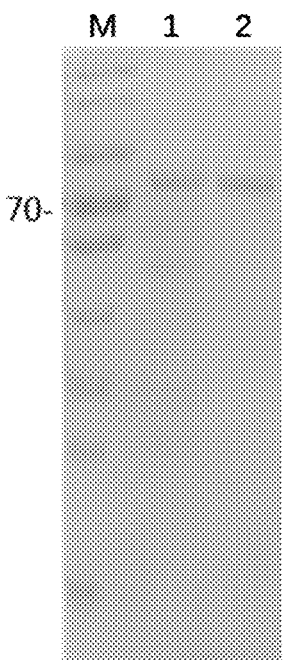
FIG. 12 shows the results of SDS-PAGE analysis of natural HA protein HK2014-WT-HA and deglycosylated protein HK2014-HAug; in which, lane M: molecular weight marker; lane 1: purified HK2014-WT-HA; lane 2: HK2014-HAug (obtained by digesting HK2014-WT-HA with endoglycosidase F for 3 hours).

FIG. 11 shows the results of SDS-PAGE analysis (left panel) and Western blot analysis (right panel) of HK2014-DG-HA protein; in which lane M: molecular weight marker; lane 1: sample without being purified by Ni-NTA nickel ion chromatography column; lane 2: fraction flowing through Ni-NTA nickel ion chromatography column; lane 3: fraction being eluted with 50 mM imidazole; lane 4: fraction being eluted with 250 mM imidazole; the arrow indicates the position of the protein of interest, HK2014-DG-HA.

The results of FIGS. 10-11 show that the proteins HK2014-WT-HA and HK2014-DG-HA were mainly contained in the fraction eluted with 250 mM imidazole; and that the molecular weight of HK2014-WT-HA was above 70KD, the molecular weight of HK2014-DG-HA decreased in some extent. These results indicate that the glycosylation modification in HK2014-DG-HA was effectively removed.

FIG. 12 shows the results of SDS-PAGE analysis of the natural HA protein HK2014-WT-HA and the deglycosylated protein HK2014-HAug; in which, lane M: molecular weight marker; lane 1: purified HK2014-WT-HA; lane 2: HK2014-HAug (obtained by digesting HK2014-WT-HA with endoglycosidase F for 3 hours).

The results of FIG. 12 show that the molecular weight of HK2014-WT-HA was above 70KD, and the molecular weight of HK2014-HAug decreased in some extent. These results indicate that the glycosylation modification in HK2014-HAug was effectively removed.

Example 6

Evaluation of Immunogenicity of H3N2 Influenza Virus HA Protein and its Mutants

The proteins HK2014-WT-HA, HK2014-DG-HA and HK2014-HAug prepared in Example 5 were separately mixed with Freund's adjuvant to prepare immunogens, which were then used to immunize 6-8 week-old Balb/C female mice (body weight about 20 g). The immunization procedure was as follows: subcutaneous immunization 3 times with an interval of 14 days for each immunization. Fourteen days after the third immunization, mouse sera were collected, and the collected serum samples were inactivated at 56° C. for 30 minutes, and then stored at −20° C. for later use.

ELISA assay was used to evaluate whether the mouse serum samples collected above had specific binding activity to the three influenza viruses A/Wisconsin/67/2005 (H3N2), A/Xiamen/N794/2013 (H3N2) and A/Shanghai/02/2013 (H7N9). Briefly, Elisa plates were coated with 100 µl of different types of influenza viruses (128HA), and then gradient-diluted mouse serum was added to the virus-coated plates and incubated at 37° C. for 1 hour. Subsequently, 1:5000 diluted GAM-HRP (provided by the National Engineering Center of Xiamen University) was added and incubated at 37° C. for 30 min. After incubation, the plates were washed, added with chromogenic solution A&B (provided by Beijing Wantai Company) and developed for 15 minutes, and then the chromogenic reaction was stopped with a stop solution. Finally, the absorbance of each well was read using a microplate reader, and the specific binding activity of mouse serum to virus was calculated. The ELISA results are shown in FIGS. 13-14.

Figure 13:
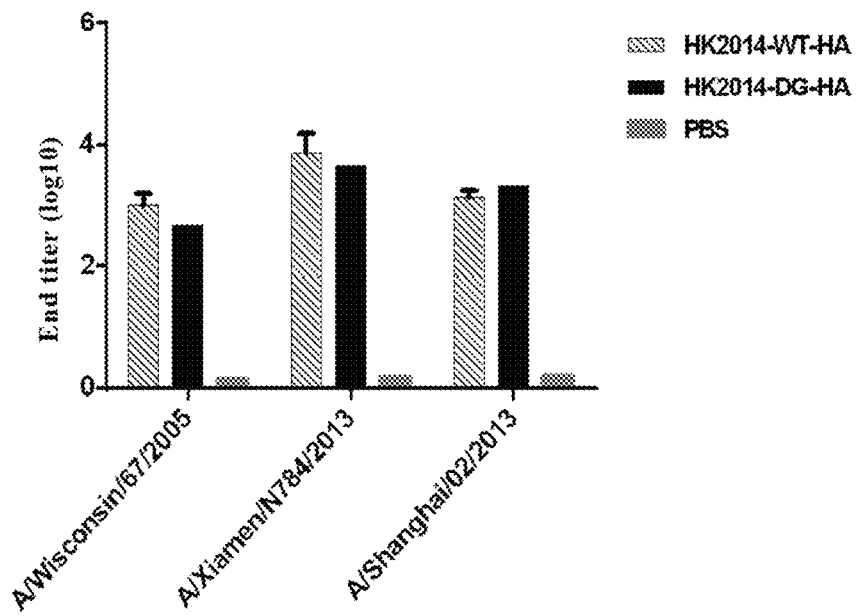
FIG. 13 shows the results of ELISA analysis evaluating binding activities to influenza viruses A/Wisconsin/67/2005 (H3N2), A/Xiamen/N794/2013 (H3N2) and A/Shanghai/02/2013 (H7N9) of mouse sera obtained by immunizing mice with HK2014-WT-HA, HK2014-DG-HA and PBS (used as negative control) as an immunogen, respectively.

FIG. 13 shows the results of ELISA analysis evaluating binding activities to influenza viruses A/Wisconsin/67/2005 (H3N2), A/Xiamen/N794/2013 (H3N2) and A/Shanghai/02/2013 (H7N9) of mouse sera obtained by immunizing mice with HK2014-WT-HA, HK2014-DG-HA and PBS (used as negative control) as an immunogen, respectively.

The results in FIG. 13 show that the mouse sera obtained from mice immunized with HK2014-WT-HA and HK2014-DG-HA all showed comparable levels of reaction titers to the three influenza viruses (A/Wisconsin/67/2005 (H3N2), A/Xiamen/N794/2013 (H3N2), A/Shanghai/02/2013 (H7N9)). The results show that HK2014-WT-HA and HK2014-DG-HA both have good immunogenicity, can trigger normal immune response in mice, induce the body to produce specific antibodies, and these specific antibodies can recognize and bind to a variety of influenza viruses.

Figure 14:
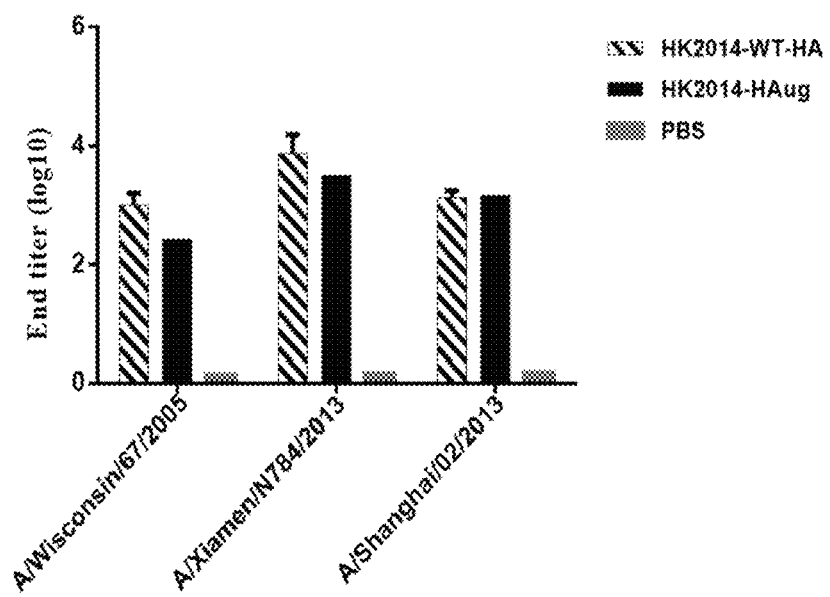
FIG. 14 shows the results of ELISA analysis evaluating binding activities to influenza viruses A/Wisconsin/67/2005 (H3N2), A/Xiamen/N794/2013 (H3N2) and A/Shanghai/02/2013 (H7N9) of mouse sera obtained by immunizing mice with HK2014-WT-HA, HK2014-HAug and PBS (used as negative control) as an immunogen, respectively.

FIG. 14 shows the results of ELISA analysis evaluating binding activities to influenza viruses A/Wisconsin/67/2005 (H3N2), A/Xiamen/N794/2013 (H3N2) and A/Shanghai/02/2013 (H7N9) of mouse sera obtained by immunizing mice with HK2014-WT-HA, HK2014-HAug and PBS (used as negative control) as an immunogen, respectively.

The results in FIG. 14 show that the mouse sera obtained from mice immunized with HK2014-WT-HA and HK2014-HAug all showed comparable levels of reaction titers to the three influenza viruses (A/Wisconsin/67/2005 (H3N2), A/Xiamen/N794/2013 (H3N2), A/Shanghai/02/2013 (H7N9)). The results show that HK2014-WT-HA and HK2014-HAug both have good immunogenicity, can trigger normal immune response in mice, induce the body to produce specific antibodies, and these specific antibodies can recognize and bind a variety of influenza virus.

Example 7

Evaluation of Immuno-Protective Properties of H3N2 Influenza Virus HA Protein and its Mutants To further verify the immuno-protective effect of the proteins prepared in Example 5 against influenza virus in animals, the following experiments were performed.

The proteins HK2014-WT-HA, HK2014-DG-HA and HK2014-HAug prepared in Example 5 were mixed with Freund's adjuvant to prepare the immunogens, which were then used to immunize 6-8 week-old Balb/C female mice (body weight about 20 g). The immunization procedure was as follows: subcutaneous immunization 3 times with an interval of 14 days for each immunization. Fourteen days after the third immunization, the mice of each group were challenged with influenza viruses, and the influenza virus strains used were: H3N2 virus strain A/Aichi/2/1968 (H3N2) which was prevalent at a time far away from the epidemic year of the immunogen, and H7N9 virus strain A/Shanghai/059/2013 (H7N9) prevalent in recent years, and both of them were lethal strains. After challenge, the body weight and survival rate of each group of mice were observed and recorded, and the potencies of the prepared proteins in protecting mice against the infection of lethal viruses were evaluated. The experimental results are shown in FIGS. 15-17.

Figure 15:
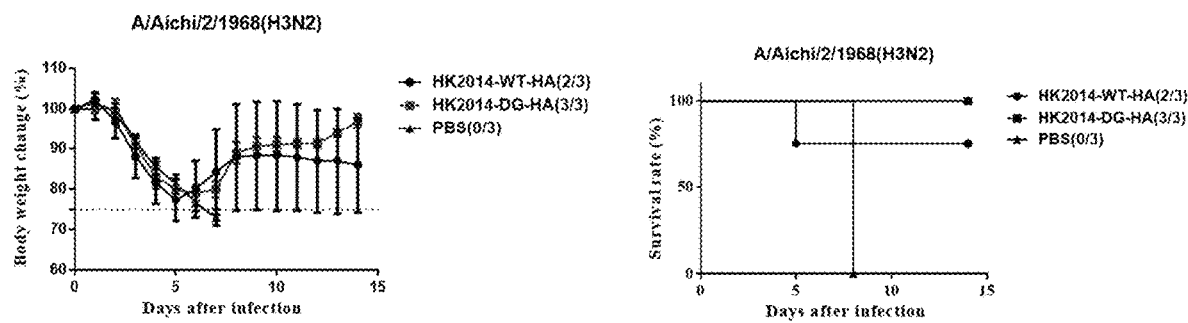
FIG. 15 shows the changes in body weight (left panel) and survival (right panel) of each group of mice (3/group) immunized with HK2014-WT-HA, HK2014-DG-HA or PBS (used as negative control) after infection with A/Aichi/2/1968 (H3N2).

FIG. 15 shows the changes in body weight (left panel) and survival (right panel) of each group of mice (3/group) immunized with HK2014-WT-HA, HK2014-DG-HA or PBS (used as negative control) after infection with A/Aichi/2/1968 (H3N2). The experimental results in FIG. 15 show that after the mice immunized with HK2014-WT-HA were infected with a lethal dose of virus A/Aichi/2/1968 (H3N2), one mouse died on the day 5, and the body weight of the remaining mice began to recover on the day 6, and the mouse survival rate was 66% at the end of the experiment; after the mice immunized with HK2014-DG-HA were infected with a lethal dose of virus A/Aichi/2/1968 (H3N2), the body weight of all mice began to recover on the day 5, and the mouse survival rate was 100% at the end of the experiment; while all mice in the negative control group died on the day 8 after infection with the virus. This result shows that compared with HK2014-WT-HA, HK2014-DG-HA has better protection effect against virus A/Aichi/2/1968 (H3N2).

Figure 16:
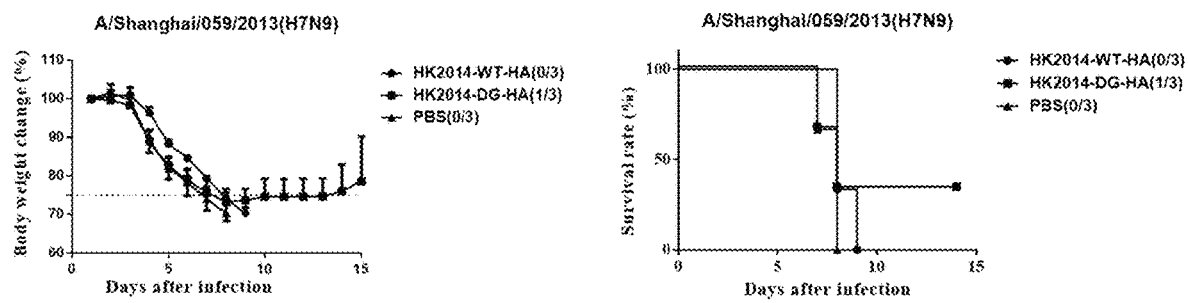
FIG. 16 shows the changes in body weight (left panel) and survival (right panel) of each group of mice (3/group) immunized with HK2014-WT-HA, HK2014-DG-HA or PBS (used as negative control) after infection with A/Shanghai/059/2013 (H7N9).

FIG. 16 shows the changes in body weight (left panel) and survival (right panel) of each group of mice (3/group) immunized with HK2014-WT-HA, HK2014-DG-HA or PBS (used as negative control) after infection with A/Shanghai/059/2013 (H7N9). The experimental results in FIG. 16 show that after the mice immunized with HK2014-WT-HA were infected with a lethal dose of virus A/Shanghai/059/2013 (H7N9), all the mice continuously lost body weight, and the mouse survival rate on the day 9 after challenge was 0%; after the mice immunized with HK2014-DG-HA were infected with a lethal dose of the virus A/Shanghai/059/2013 (H7N9), one mouse began to recover body weight on the day 8, and the mouse survival rate was 33% at the end of the experiment. This result shows that HK2014-WT-HA does not have protection effect against the influenza virus A/Shanghai/059/2013 (H7N9); in contrast, HK2014-DG-HA shows a certain protection effect (broad-spectrum protection across subtypes) against virus A/Shanghai/059/2013 (H7N9).

Figure 17:
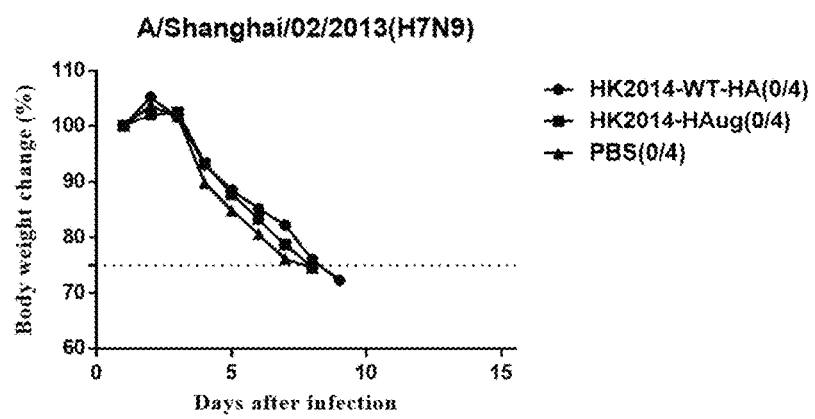
FIG. 17 shows the changes in body weight of each group of mice (4/group) immunized with HK2014-WT-HA, HK2014-HAug or PBS (used as negative control) after infection with A/Shanghai/059/2013 (H7N9).

FIG. 17 shows the changes in body weight of each group of mice (4/group) immunized with HK2014-WT-HA, HK2014-HAug or PBS (used as negative control) after infection with A/Shanghai/059/2013 (H7N9). The experimental results in FIG. 17 show that, after the mice immunized with HK2014-WT-HA, HK2014-HAug or PBS were infected with a lethal dose of virus A/Shanghai/059/2013 (H7N9), the body weight of all mice continuously decreased, and the mouse survival rate was all 0% on the day 9 after challenge. This result shows that neither HK2014-WT-HA nor HK2014-HAug has protective effect against virus A/Shanghai/059/2013 (H7N9).

From the above results, it can be seen that HK2014-DG-HA is more suitable as an influenza vaccine than HK2014-WT-HA and HK2014-HAug, which can resist the infection of influenza viruses of H3N2 subtype (regardless of the distance of evolutionary relationship) and H7N9 subtype, showing a broad-spectrum protection across subtypes and better protection.

Although the specific embodiments of the present invention have been described in detail, those skilled in the art will understand that according to all the teachings that have been disclosed, various modifications and changes can be made to the details, and these changes are all within the protection scope of the present invention. The full scope of the present invention is given by the appended claims and any equivalents thereof.

What is claimed is:

1. A mutant of hemagglutinin protein of H3N2 subtype influenza virus, wherein the mutant differs from a wild-type hemagglutinin protein of the H3N2 subtype influenza virus at least in that the N residue in each characteristic sequence N-X-(S or T) in the wild-type hemagglutinin protein is independently replaced with a non-N amino acid residue, so that the mutant contains no characteristic sequence N-X-(S or T); wherein, N represents asparagine, X represents any one amino acid other than proline, S represents serine, and T represents threonine; and optionally the mutant does not contain a N-terminal signal peptide and/or a transmembrane region of the wild-type hemagglutinin protein.

2. A recombinant protein, comprising the mutant according to claim 1 and an additional peptide segment, and the additional peptide segment is linked to the mutant.

3. A nucleic acid molecule, comprising or consisting of a nucleotide sequence encoding one of the following:
 (i) the mutant according to claim 1; and
 (ii) a recombinant protein comprising the mutant of (i) and an additional peptide segment linked to the mutant.

4. A vector, comprising the nucleic acid molecule according to claim 3.

5. A host cell or virus, comprising
 (i) the nucleic acid molecule according to claim 3; or
 (ii) a vector comprising the nucleic acid molecule of (i).

6. A multimer, comprising or consisting of a plurality of
 (i) the mutants according to claim 1; or
 (ii) a recombinant protein comprising the mutant of (i) and an additional peptide segment linked to the mutant.

7. A pharmaceutical composition, comprising
 a pharmaceutically acceptable carrier and/or excipient, and one or more of the following:
 (i) the mutant according to claim 1;
 (ii) a recombinant protein comprising the mutant of (i) and an additional peptide segment linked to the mutant; and
 (iii) a multimer comprising or consisting of a plurality of the mutant of (i) or a plurality of the recombinant protein of (ii);
 optionally, the pharmaceutical composition is a vaccine.

8. The mutant according to claim 1, wherein the N residue in each characteristic sequence N-X-(S or T) in the wild-type hemagglutinin protein is independently conservatively replaced.

9. The mutant according to claim 1, characterized by one or more of the following items:
 (a) the wild-type hemagglutinin protein is from A/WISCONSIN/67/2005 (H3N2) or A/HONG_KONG/4801/2014 (H3N2);
 (b) the wild-type hemagglutinin protein has a sequence selected from the group consisting of: SEQ ID NOs: 1 and 6;
 (c) the wild-type hemagglutinin protein has an amino acid sequence as shown in SEQ ID NO: 1; and, optionally, the mutant does not contain amino acids 1-10 of SEQ ID NO: 1 and/or amino acids 504-550 of SEQ ID NO: 1;
 (d) the wild-type hemagglutinin protein has an amino acid sequence as shown in SEQ ID NO: 6; and, optionally, the mutant does not contain amino acids 1-25 of SEQ ID NO: 6 and/or amino acids 518-565 of SEQ ID NO: 6; and
 (e) the mutant has an amino acid sequence selected from the group consisting of SEQ ID NOs: 12-13; or, the mutant has an identity of at least 85%, at least 90%, at least 91%, and 92%, at least 93%, at least 94%, at least 95%, at least 96%, at least 97%, at least 98%, at least 99% or 100% to an amino acid sequence selected from the group consisting of: SEQ ID NOs: 12-13; or, the mutant has an addition, deletion or substitution of one or more amino acid residues as compared to an amino acid sequence selected from the group consisting of: SEQ ID NOs: 12-13.

10. The recombinant protein according to claim 2, characterized by one or more of the following items:
 (a) the additional peptide segment is directly linked to the mutant or is linked to the mutant through a linker;
 (b) the additional peptide segment is linked to the N-terminus or C-terminus of the mutant;
 (c) the recombinant protein comprises at least 1, at least 2, at least 3, at least 5 or more additional peptide segments; and
 (d) the additional peptide segment is selected from the group consisting of a signal peptide, a tag peptide, a folding motif, a detectable label, and any combination thereof.

11. The recombinant protein according to claim 10, characterized by one or more of the following items:
 (a) the signal peptide is linked to the N-terminus of the mutant;
 (b) the signal peptide has an amino acid sequence as shown in SEQ ID NO: 9;
 (c) the folding motif is linked to the C-terminus of the mutant; and
 (d) the folding motif has an amino acid sequence as shown in SEQ ID NO: 10.

12. The host cell or virus according to claim 5, wherein the virus is a baculovirus.

13. The multimer according to claim 6, wherein the multimer is a trimer.

* * * * *